(12) United States Patent
Kohno et al.

(10) Patent No.: US 7,763,752 B2
(45) Date of Patent: Jul. 27, 2010

(54) AMINO ALCOHOL DERIVATIVES, SALTS THEREOF AND IMMUNOSUPPRESIVE AGENTS

(75) Inventors: Yasushi Kohno, Tochigi (JP); Kiyoaki Tanaka, Tochigi (JP); Kazuhiko Kuriyama, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/292,609

(22) Filed: Nov. 21, 2008

(65) Prior Publication Data

US 2009/0156653 A1    Jun. 18, 2009

Related U.S. Application Data

(62) Division of application No. 10/528,240, filed as application No. PCT/JP03/11753 on Sep. 16, 2003, now Pat. No. 7,482,491.

(30) Foreign Application Priority Data

Sep. 19, 2002    (JP)    ............... 2002-272834

(51) Int. Cl.
C07C 215/00    (2006.01)
A61K 31/00    (2006.01)

(52) U.S. Cl. .............. 564/355; 564/341; 564/346; 564/348; 564/351; 564/360; 564/366; 564/374; 546/334; 514/357; 514/649; 514/651; 514/653

(58) Field of Classification Search .................. None
See application file for complete search history.

(56) References Cited

U.S. PATENT DOCUMENTS

| | | | |
|---|---|---|---|
| 4,252,951 A * | 2/1981 | Jackson et al. .............. 540/220 |
| 5,447,922 A | 9/1995 | Lawrence et al. |
| 5,543,542 A | 8/1996 | Lawrence et al. |
| 5,604,229 A | 2/1997 | Fujita et al. |
| 5,719,176 A | 2/1998 | Fujita et al. |
| 5,948,820 A | 9/1999 | Fujita et al. |
| 5,952,316 A | 9/1999 | Fujita et al. |
| 6,437,165 B1 | 8/2002 | Mandala et al. |
| 6,723,745 B2 | 4/2004 | Nishi et al. |
| 6,960,692 B2 | 11/2005 | Kohno et al. |
| 6,963,012 B2 | 11/2005 | Kohno et al. |
| 6,964,976 B2 | 11/2005 | Nishi et al. |
| 7,064,217 B2 | 6/2006 | Macdonald et al. |
| 7,179,817 B2 | 2/2007 | Seko et al. |
| 7,199,142 B2 | 4/2007 | Chen et al. |
| 7,241,790 B2 | 7/2007 | Lynch et al. |
| 7,288,558 B2 | 10/2007 | Nakade et al. |
| 7,309,721 B2 | 12/2007 | Budhu et al. |
| 7,326,801 B2 | 2/2008 | Albert et al. |
| 7,351,725 B2 | 4/2008 | Doherty et al. |
| 7,482,491 B2 * | 1/2009 | Kohno et al. .............. 564/355 |
| 2002/0091105 A1 | 7/2002 | Mandala et al. |
| 2003/0236297 A1 | 12/2003 | Nishi et al. |
| 2004/0058894 A1 | 3/2004 | Doherty et al. |
| 2004/0110728 A1 | 6/2004 | Macdonald et al. |
| 2004/0132784 A1 | 7/2004 | Nishi et al. |
| 2004/0235794 A1 | 11/2004 | Nakade et al. |
| 2005/0020837 A1 | 1/2005 | Doherty et al. |
| 2005/0033055 A1 | 2/2005 | Bugianesi et al. |
| 2005/0070506 A1 | 3/2005 | Doherty et al. |
| 2005/0107345 A1 | 5/2005 | Doherty et al. |
| 2006/0148844 A1 | 7/2006 | Nakade et al. |
| 2006/0160771 A1 | 7/2006 | Kohno et al. |
| 2006/0166940 A1 | 7/2006 | Buehlmayer et al. |
| 2007/0088027 A1 | 4/2007 | Seko et al. |
| 2007/0135402 A1 | 6/2007 | Habashita et al. |
| 2007/0219163 A1 | 9/2007 | Lynch et al. |
| 2007/0224263 A1 | 9/2007 | Doherty et al. |

FOREIGN PATENT DOCUMENTS

| | | |
|---|---|---|
| EP | 0 698 609 | 2/1996 |
| EP | 1 092 435 | 4/2001 |
| JP | 2002-53572 | 2/2002 |
| JP | 2002-53575 | 2/2002 |
| JP | 2003-137894 | 5/2003 |
| JP | 2003-267936 | 9/2003 |
| JP | 2004-137208 | 5/2004 |
| WO | 94/08943 | 4/1994 |
| WO | 00/40560 | 7/2000 |
| WO | 01/98301 | 12/2001 |
| WO | 02/06268 | 1/2002 |
| WO | 02/18395 | 3/2002 |
| WO | 02/062389 | 8/2002 |
| WO | 02/064616 | 8/2002 |

(Continued)

OTHER PUBLICATIONS

Chem. Commun. (2005), 29, p. 3635-3645.*

(Continued)

Primary Examiner—Brian J Davis
(74) Attorney, Agent, or Firm—Wenderoth, Lind & Ponack, L.L.P.

(57) ABSTRACT

An amino alcohol derivative represented by the following general formula (1) (for example, (±)-2-amino-5-[4-(3-benzyloxyphenylthio)-2-chlorophenyl]-2-methylpentane-1-ol) exhibits strong immunosuppressive effect while causing less side effects:

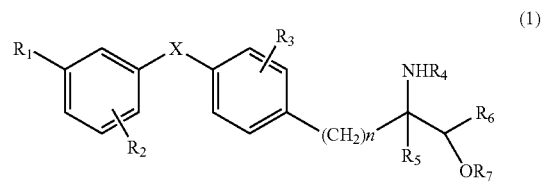

(1)

12 Claims, No Drawings

FOREIGN PATENT DOCUMENTS

| | | |
|---|---|---|
| WO | 02/076995 | 10/2002 |
| WO | 02/092068 | 11/2002 |
| WO | 02/094770 | 11/2002 |
| WO | 03/020313 | 3/2003 |
| WO | 03/029184 | 4/2003 |
| WO | 03/029205 | 4/2003 |
| WO | 03/040097 | 5/2003 |
| WO | 03/051876 | 6/2003 |
| WO | 03/061567 | 7/2003 |
| WO | 03/062248 | 7/2003 |
| WO | 03/062252 | 7/2003 |
| WO | 03/073986 | 9/2003 |
| WO | 03/074008 | 9/2003 |
| WO | 03/105771 | 12/2003 |
| WO | 2004/002531 | 1/2004 |
| WO | 2004/010949 | 2/2004 |
| WO | 2004/024673 | 3/2004 |
| WO | 2004/074297 | 9/2004 |

OTHER PUBLICATIONS

Yoh Takuwa et al., "Subtype-specific, differential activities of the *EDG* family receptors for sphingosine-1-phosphate, a novel lysophospholipid mediator", Molecular and Cellular Endocrinology, 177, pp. 3-11, 2001.

Yasuyuki Igarashi, "Sphingosine-1-Phosphate as an Intercellular Signaling Molecule", Annals New York Academy of Sciences, 845, pp. 19-31, 1998.

Hiroshi Okazaki et al., "Molecular Cloning of a Novel Putative G Protein-Coupled Receptor Expressed in the Cardiovascular System", Biochemical and Biophysical Research Communications, Vol. 190, No. 3, pp. 1104-1109, Feb. 15, 1993.

Volker Brinkmann et al., "The Immune Modulator FTY720 Targets Sphingosine 1-Phosphate Receptors", The Journal of Biological Chemistry, vol. 277, No. 24, pp. 21453-21457, 2002.

Suzanne Mandala et al., "Alteration of Lymphocyte Trafficking by Sphingosine-1-Phosphate Receptor Agonists", Science, Vol. 296, pp. 346-349, Apr. 12, 2002.

M. Germana Sanna et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279, No. 14, pp. 13839-13848, Apr. 2, 2004.

M. Forrest et al., "Immune Cell Regulation and Cardiovascular Effects of Sphingosine 1-Phosphate Receptor Agonists in Rodents are Mediated via Distinct Receptor Subtypes", The Journal of Pharmacology and Experimental Therapeutics, vol. 309, No. 2, pp. 758-768, 2004.

Bodo Levkau et al., "High-Density Lipoprotein Stimulates Myocardial Perfusion in Vivo", Circulation, 110, pp. 3355-3359, 2004.

Salvatore Salomone et al., "$S1P_3$, receptors mediate the potent constriction of cerebral arteries by sphingosine-1-phosphate", European Journal of Pharmacology, 469, pp. 125-134, 2003.

Database CAPLUS on STN, Acc. No. 2000:34744, Shumada et al., WO 2000001388 (Jan. 13, 2000) (abstract).

International Search Report dated Dec. 24, 2003 in the International (PCT) Application PCT/JP2003/11753 corresponding to the parent application of the present divisional application.

International Preliminary Report on Patentability dated Jul. 14, 2004 in the International (PCT) Application PCT/JP2003/11753 corresponding to the parent application of the present divisional application.

* cited by examiner

AMINO ALCOHOL DERIVATIVES, SALTS THEREOF AND IMMUNOSUPPRESIVE AGENTS

The present application is a divisional application of Ser. No. 10/528,240, filed Apr. 22, 2005, now U.S. Pat. No. 7,482,491, which is a 371 application of PCT/JP2003/011753, filed Sep. 16, 2003.

TECHNICAL FIELD

The present invention relates to amino alcohol derivatives, salts and hydrates thereof that are suitable for use as immunosuppressive agents.

BACKGROUND ART (Patent Article 1) International Patent Publication No. WO 9408943

(Patent Article 2) Japanese Patent Laid-Open Publication No. Hei 9-2579602

(Patent Article 3) International Patent Publication No. WO 0206268

(Patent Article 4) Japanese Patent Laid-Open Publication No. Hei 2002-53575

(Patent Article 5) Japanese Patent Laid-Open Publication No. Hei 2002-167382

Immunosuppressive agents are widely used as a treatment for autoimmune diseases such as rheumatoid arthritis, nephritis, osteoarthritis of and systemic lupus erythematosus, chronic inflammatory diseases such as inflammatory bowel disease, and allergic diseases such as asthma and dermatitis. Progress in medicine has led to the rise in the number of tissue and organ transplantations performed each year. In such a situation of modern medicine, having as much control as possible over the rejection following transplantation is a key to a successful transplantation. Immunosuppressive agents also play a significant role in this aspect.

In organ transplantations, antimetabolites, such as azathioprine and mycophenolate mofetil, calcineurin inhibitors, such as cyclosporin A and tacrolimus, and corticosteroid, such as prednisolone are typically used. However, some of these drugs are not effective enough while others require continuous monitoring of the blood drug level to avoid renal failure and other serious side effects. Thus, none of conventional immunosuppressive agents are satisfactory in view of efficacy and potential side effects.

Multiple drug combined-therapy, in which different immunosuppressive drugs with different mechanisms of action are used, is becoming increasingly common for the purposes of alleviating the side effects of the drugs and achieving sufficient immunosuppressive effects. Also, development of new types of immunosuppressive agents that have completely different mechanisms of action is sought.

In an effort to respond to such demands, the present inventors conducted a search for new types of immunosuppressive agents with main interest in 2-amino-1-ethanol derivatives.

While the use of 2-amino-1,3-propanediol derivatives as immunosuppressive agents has been described in Patent Articles No. 1 and No. 2, it has not been previously known that 2-amino-1-ethanol derivatives bearing a diaryl sulfide group or a diaryl ether group, the subject compounds of the present invention, exhibit significant immunosuppressive effects. Although Patent Articles No. 3, No. 4 and No. 5 disclose amino alcohol derivatives that act as immunosuppressive agents, these compounds have different structures from the compounds of the present invention.

DISCLOSURE OF THE INVENTION

Accordingly, it is an objective of the present invention to provide an amino alcohol derivative that has significant immunosuppressive effects but causes less side effects.

In the course of studies on immunosuppressive agents that act by different mechanism of action than antimetabolites and calcineurin inhibitors, the present inventors discovered that novel diaryl sulfide- or diaryl ether-containing amino alcohol derivatives that have a different structure from known immunosuppressors exhibit strong immunosuppressive effects. Specifically, the compounds each include, at the para-position of one of the two aryl groups, a carbon chain with an amino alcohol group and also include a particular substituent at the meta-position of the other of the aryl groups. This discovery led the present inventors to devise the present invention.

The present invention thus is an immunosuppressive agent containing as an active ingredient at least one of an amino alcohol derivative, and an optical isomer, a pharmaceutically acceptable salt and a hydrate thereof, the amino alcohol derivative represented by the following general formula (1):

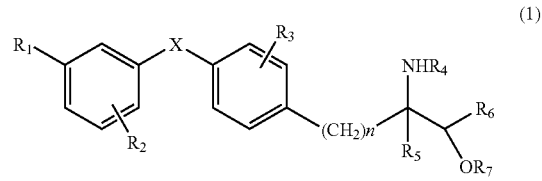

[wherein $R_1$ is a halogen atom, a trihalomethyl group, a lower alkyl group having 1 to 4 carbon atoms, an aralkyl group, a lower alkoxy group having 1 to 4 carbon atoms, a substituted or unsubstituted phenoxy group, a substituted or unsubstituted aralkyloxy group, a lower alkylthio group having 1 to 4 carbon atoms, a lower alkylsulfinyl group having 1 to 4 carbon atoms, or a lower alkylsulfonyl group having 1 to 4 carbon atoms; $R_2$ is a hydrogen atom, a halogen atom, a trihalomethyl group, a lower alkyl group having 1 to 4 carbon atoms, an aralkyl group, a lower alkoxy group having 1 to 4 carbon atoms, or a aralkyloxy group; $R_3$ is a hydrogen atom, a halogen atom, a trifluoromethyl group, a lower alkoxy group having 1 to 4 carbon atoms, a benzyloxy group, a lower alkyl group having 1 to 4 carbon atoms, or a lower alkoxythio group having 1 to 4 carbon atoms; $R_4$ is a hydrogen atom, a lower alkyl group having 1 to 4 carbon atoms, a phenyl group, a substituted or unsubstituted benzyl group, a lower aliphatic acyl group having 1 to 5 carbon atoms, or a substituted or unsubstituted benzoyl group; $R_5$ is a hydrogen atom, a monohalogenated methyl group, a lower alkyl group having 1 to 4 carbon atoms, a lower alkoxymethyl group having 1 to 4 carbon atoms, a lower alkylthiomethyl group having 1 to 4 carbon atoms, a hydroxyethyl group, a hydroxypropyl group, a phenyl group, an aralkyl group, a lower alkenyl group having 2 to 4 carbon atoms, or a lower alkynyl group having 2 to 4 carbon atoms; $R_6$ and $R_7$ are each independently a hydrogen atom, or a lower alkyl group having 1 to 4 carbon atoms; and X is O, S, SO, or SO$_2$; and n is an integer from 1 to 4].

BEST MODE FOR CARRYING OUT THE INVENTION

More specifically, the present invention concerns an immunosuppressive agent containing as an active ingredient at least one of an amino alcohol derivative represented by the following general formulae (1a):

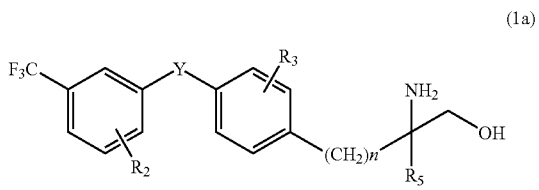

(1a)

[wherein Y represents O or S, and R$_2$, R$_3$, R$_5$ and n are as described above], an optical isomer, and a pharmaceutically acceptable salt thereof, and an amino alcohol derivative represented by the following general formulae (1b):

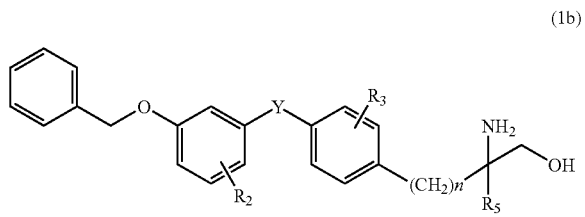

(1b)

[wherein Y represents O or S, and R$_2$, R$_3$, R$_5$ and n are as described above], an optical isomer, a pharmaceutically acceptable salt and a hydrate thereof.

The compounds of the general formulae (1), (1a), and (1b) of the present invention are each a novel compound.

Examples of the pharmaceutically acceptable salts of the compound of the general formula (1) in accordance with the present invention include acid-salts, such as hydrochloride, hydrobromide, acetate, trifluoroacetate, methanesulfonate, citrate, and tartrate.

With regard to the general formula (1), the term "halogen atom" encompasses fluorine, chlorine, bromine, and iodine atoms. The term "trihalomethyl group" encompasses trifluoromethyl and trichloromethyl. The term "lower alkyl" as used in the phrases "lower alkyl group having 1 to 4 carbon atoms," "lower alkoxy group having 1 to 4 carbon atoms," "lower alkylthio group having 1 to 4 carbon atoms," "lower alkylsulfinyl group having 1 to 4 carbon atoms," and "lower alkylsulfonyl group having 1 to 4 carbon atoms" encompasses straight-chained or branched hydrocarbons having 1 to 4 carbon atoms, such as methyl, ethyl, propyl, isopropyl, butyl, and t-butyl. The phrases "substituted or unsubstituted phenoxy group," "substituted or unsubstituted aralkyl group," "substituted or unsubstituted benzoyl group," and "substituted or unsubstituted benzyl group" encompass those that have, at any position of its benzene ring, a halogen atom, such as fluorine, chlorine, bromine and iodine atoms, trifluoromethyl, lower alkyl having 1 to 4 carbon atoms, and lower having 1 to 4 carbon atoms. The term "aralkyl group" as in "aralkyl group" or "aralkyloxy group" encompasses benzyl, diphenylmethyl, phenethyl, and phenylpropyl. As used herein, the phrase "lower aliphatic acyl group having 1 to 5 carbons" encompasses straight-chained or branched lower aliphatic acyl groups having 1 to 5 carbon atoms, such as formyl, acetyl, propionyl, butyryl, isobutyryl, valeryl, isovaleryl, and pivaloyl. The phrase "lower alkenyl group having 2 to 4 carbon atoms" as used herein encompasses hydrocarbons having 2 to 4 carbon atoms and having unsaturated double bonds, such as vinyl, allyl, 1-propenyl, isopropenyl, 1-butenyl, 2-butenyl, 2-methylallyl, and 3-butenyl. The phrase "lower alkynyl group having 2 to 4 carbon atoms" as used herein encompasses hydrocarbons having 2 to 4 carbon atoms and having unsaturated triple bonds, such as ethynyl, 1-propynyl, 2-propynyl, 1-butynyl, 2-butynyl, and 3-butynyl.

Of the compounds of the general formula (1), those in which each of R$_4$, R$_6$, and R$_7$ is a hydrogen atom are represented by the following general formula (1c):

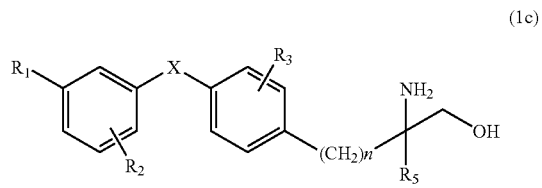

(1c)

[wherein R$_1$, R$_2$, R$_3$, R$_5$, X, and n are as described above]. According to the present invention, these compounds can be produced by the following pathway.

Synthetic pathway 1

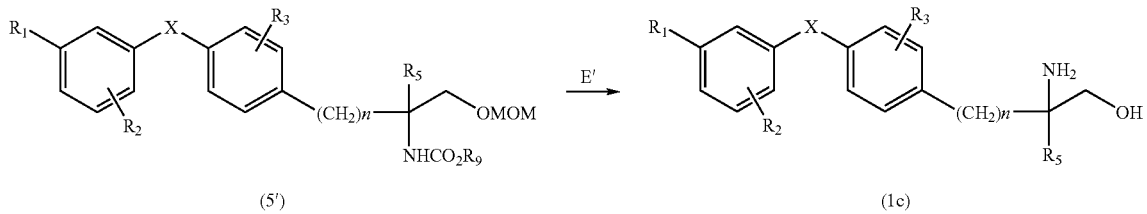

(5')    (1c)

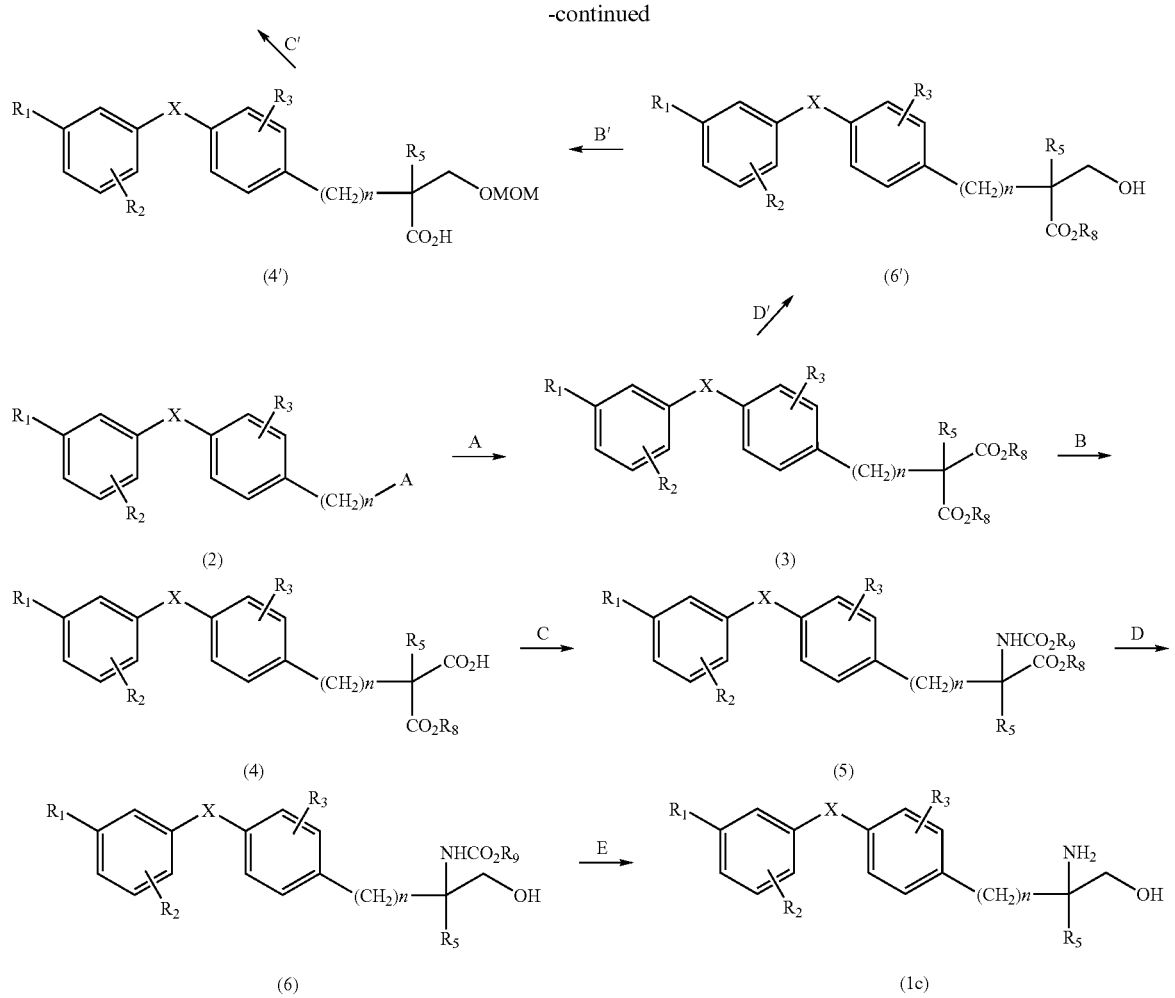

In the synthetic pathway 1, the compound represented by the general formula (3) can be obtained by reacting the compound represented by the general formula (2) with the compound represented by the general formula (7) in the presence of a base (Step A):

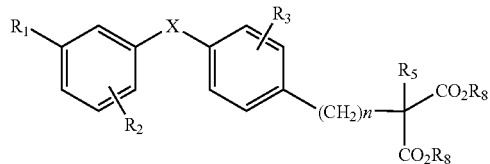

[where $R_8$ represents a lower alkyl group having 1 to 4 carbon atoms, and $R_1$, $R_2$, $R_3$, $R_5$, X, and n are as described above;

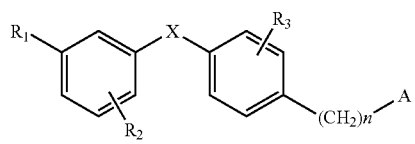

[wherein A represents a chlorine atom, a bromine atom, an iodine atom, or a fluorine atom, and $R_1$, $R_2$, $R_3$, X, and n are as described above]; and

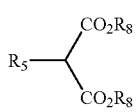

[wherein $R_5$ and $R_8$ are as described above].

This reaction uses a reaction solvent, such as methanol, ethanol, 1,4-dioxane, dimethylsulfoxide (DMSO), N,N-dimethylformamide (DMF), and tetrahydrofuran (THF), and is carried out at a temperature of 0° C. to refluxing temperature, preferably 80° C. to 100° C., in the presence of inorganic base, such as sodium hydride, potassium hydride, sodium alkoxide, potassium alkoxide, potassium carbonate, and sodium carbonate.

In the synthetic pathway 1, the compound represented by the general formula (4) can be obtained by hydrolyzing the compound of the general formula (3) (Step B):

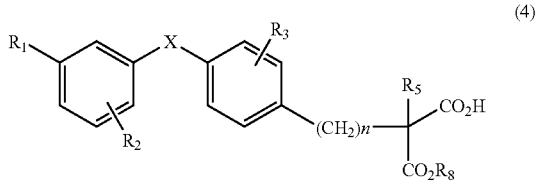

(4)

[wherein $R_1$, $R_2$, $R_3$, $R_5$, $R_8$, X, and n are as described above].

This reaction is carried out at a temperature of 0° C. to refluxing temperature in the presence of a base, such as an aqueous solution of sodium hydroxide, potassium hydroxide, or lithium hydroxide, and in a reaction solvent such as methanol, ethanol, 1,4-dioxane, DMF, or DMSO. Preferably, the reaction is carried out at 50° C. in ethanol solvent and in the presence of potassium hydroxide.

In the synthetic pathway 1, the compound represented by the general formula (5) can be obtained by Curtius rearrangement of the compound of the general formula (4) (Step C):

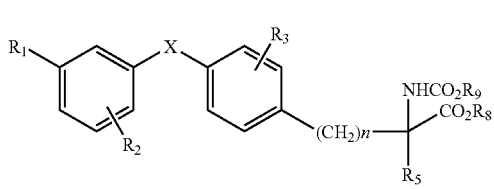

(5)

wherein $R_9$ represents a lower alkyl group having 1 to 4 carbon atoms, and $R_1$, $R_2$, $R_3$, $R_5$, $R_8$, X, and n are as described above.

This reaction can be carried out by a common process to convert a carboxyl group into carbamate. One such process involves ethyl chlorocarbonate and $NaN_3$. In another process, diphenyl phosphorazidate (DPPA) in benzene or toluene is stirred in the presence of a base such as triethylamine while the reaction mixture is heated. Subsequently, a lower alcohol, such as methanol, ethanol, propanol, isopropanol, butanol or t-butanol, is added and the mixture is further stirred while being heated. In still another process, a lower alcohol alone is used as the reaction solvent and the reaction mixture is stirred or refluxed while being heated.

In the synthetic pathway 1, the compound represented by the general formula (6) can be obtained by reducing the compound of the general formula (5) (Step D):

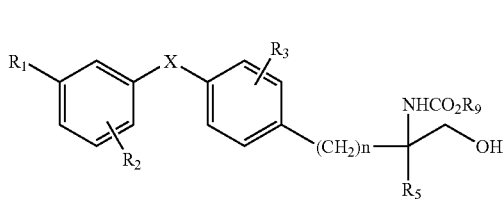

(6)

[wherein $R_1$, $R_2$, $R_3$, $R_5$, $R_9$, X, and n are as described above].

This reaction uses borane ($BH_3$), an alkylborane derivative, such as 9-borabicyclo[3.3.1]nonane (9-BBN), or a metal hydride complex, such as diisobutyl aluminum hydride ($(iBu)_2AlH$), sodium borohydride ($NaBH_4$), and lithium aluminum hydride ($LiAlH_4$), and preferably uses lithium borohydride ($LiBH_4$). The reaction is carried out at a temperature of 0° C. to refluxing temperature, preferably at room temperature, by using THF, 1.4-dioxane, methanol, or ethanol as a reaction solvent.

In the synthetic pathway 1, the compound represented by the general formula (1c) can be obtained by acidolysis or hydrolysis of the compound of the general formula (6) (Step E).

This reaction is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, and ethyl acetate. Alternatively, the reaction may use methanol, ethanol, 1,4-dioxane, DMSO, DMF, or THF as a reaction solvent and is carried out at a temperature of 0° C. to refluxing temperature, preferably 80° C. to 100° C., in the presence of a base, such as an aqueous solution of sodium hydroxide, potassium hydroxide, or lithium hydroxide.

In the synthetic pathway 1, the compound represented by the general formula (6') can be obtained by reducing the compound of the general formula (3) (Step D'):

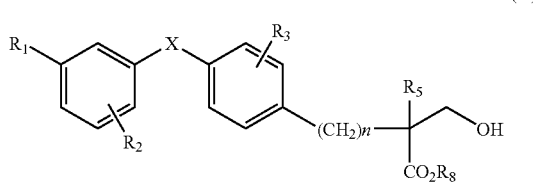

(6')

[wherein $R_1$, $R_2$, $R_3$, $R_5$, $R_8$, X, and n are as described above].

This reaction uses an alkylborane derivative, such as $BH_3$ or 9-BBN, or a metal hydride complex, such as $(iBu)_2AlH$, $NaBH_4$, $LiBH_4$, or $LiAlH_4$, in particular, lithium tributoxy aluminum hydride ($LiAl(t-BuO)_3$), along with a reaction solvent such as 1,4-dioxane, ethanol, or methanol, in particular, THF. The reaction is carried out at a temperature of 0° C. to refluxing temperature and, preferably, at room temperature.

In the synthetic pathway 1, the compound represented by the general formula (4') can be obtained by protecting the hydroxyl group of the compound of the general formula (6') with methoxymethyl (MOM) group and subsequently hydrolyzing the ester (Step B'):

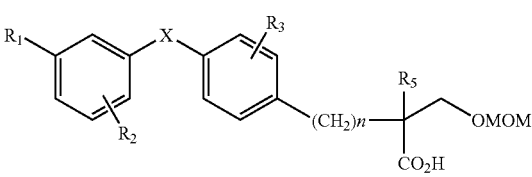

(4')

[wherein MOM represents a methoxymethyl group, and $R_1$, $R_2$, $R_3$, $R_5$, X, and n are as described above.

This reaction uses a base, such as triethylamine, or pyridine, in particular, diisopropylethylamine, along with an organic solvent, such as THF, 1,4-dioxane, methylene chloride, chloroform, or acetonitrile. The compound of the general formula (6') is first reacted with methoxymethyl chloride or methoxymethyl bromide at 0° C. to room temperature to introduce the MOM group. Subsequently, the protected compound is hydrolyzed in a reaction solvent, such as methanol, ethanol, 1,4-dioxane, DMF, or DMSO, at a temperature of 0° C. to refluxing temperature and in the presence of a base, such as an aqueous solution of sodium hydroxide, potassium hydroxide, or lithium hydroxide.

In the synthetic pathway 1, the compound represented by the general formula (5') can be obtained by Curtius rearrangement of the compound of the general formula (4') (Step C'):

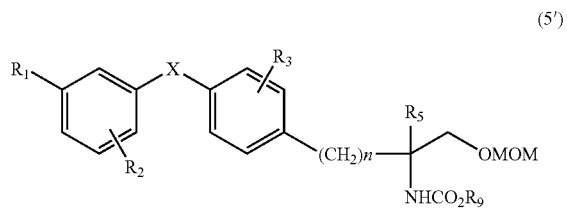

(5')

[wherein $R_1$, $R_2$, $R_3$, $R_5$, $R_9$, MOM, X, and n are as described above].

This reaction can be carried out by a common process to convert a carboxyl group into carbamate. One such process involves ethyl chlorocarbonate and $NaN_3$. In another process, diphenyl phosphorazidate (DPPA) in benzene or toluene is stirred in the presence of a base such as triethylamine while the reaction mixture is heated. Subsequently, a lower alcohol, such as methanol, ethanol, propanol, isopropanol, butanol, or t-butanol, is added and the mixture is further stirred while being heated. In still another process, a lower alcohol alone is used as the reaction solvent and the reaction mixture is stirred or refluxed while being heated.

The compound represented by the general formula (1c) can be obtained by acidolysis or hydrolysis of the compound of the general formula (5') (Step E').

This reaction is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. Alternatively, the carbamate group is first deprotected in a reaction solvent, such as methanol, ethanol, 1,4-dioxane, DMSO, DMF, or THF, at a temperature of 0° C. to refluxing temperature, preferably 80° C. to 100° C., and in the presence of a base, such as an aqueous solution of sodium hydroxide, potassium hydroxide, or lithium hydroxide. Subsequently, the MOM group is eliminated by acidolysis.

Of the compounds of the general formula (1), those in which $R_4$ is a hydrogen atom, a lower alkyl group having 1 to 4 carbon atoms, a phenyl group or a substituted or unsubstituted benzyl group, and $R_5$, $R_6$, and $R_7$ are each a hydrogen atom are represented by the following general formula (1d):

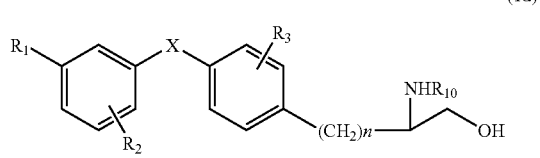

(1d)

[wherein $R_{10}$ is a hydrogen atom, a lower alkyl group having 1 to 4 carbon atoms, a phenyl group, or a substituted or unsubstituted benzyl group; and $R_1$, $R_2$, $R_3$, X, and n are as described above]. These compounds can be produced by the following pathway:

Synthetic pathway 2

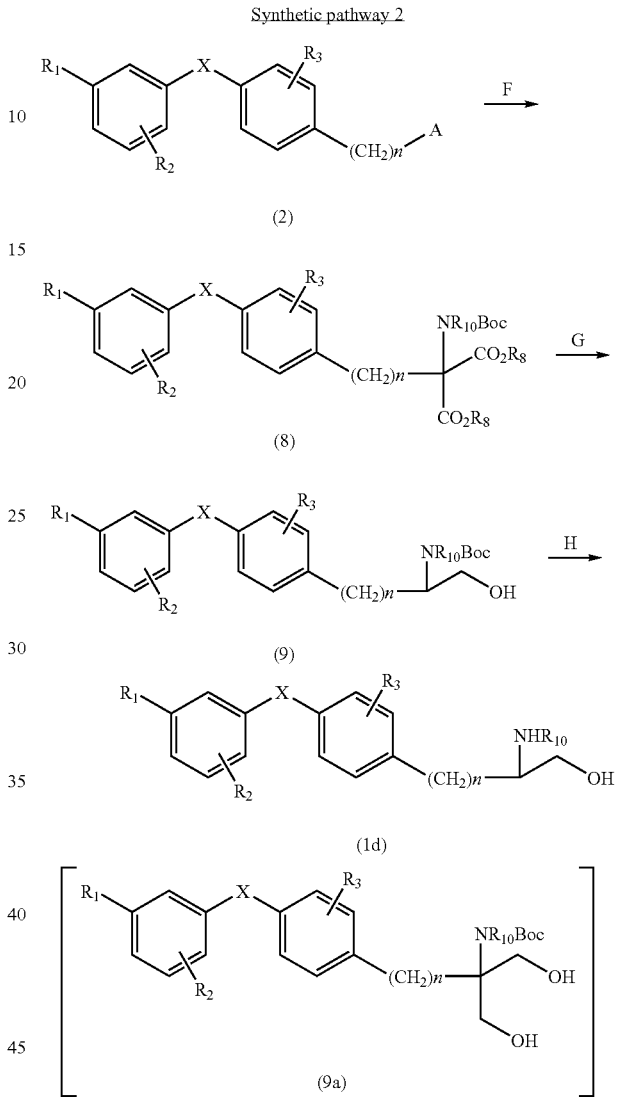

In the synthetic pathway 2, the compound represented by the general formula (8) can be obtained by reacting the compound represented by the general formula (2) with the compound represented by the general formula (10) in the presence of a base (Step F):

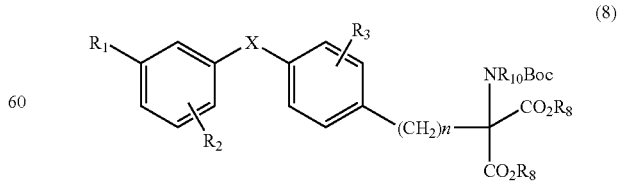

(8)

[wherein Boc represents t-butoxycarbonyl; and $R_1$, $R_2$, $R_3$, $R_8$, $R_{10}$, X, and n are as described above]; and

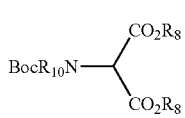  (10)

[wherein $R_8$, $R_{10}$, and Boc are as described above].

This reaction uses a reaction solvent such as methanol, ethanol, 1,4-dioxane, DMSO, DMF, or THF, and is carried out at a temperature of 0° C. to refluxing temperature, preferably 80° C. to 100° C., in the presence of an inorganic base, such as sodium hydride, potassium hydride, sodium alkoxide, potassium alkoxide, potassium carbonate, or sodium carbonate.

In the synthetic pathway 2, the compound represented by the following general formula (9) can be obtained by reducing the compound of the general formula (8) (Step G):

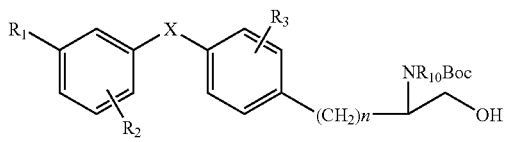  (9)

[wherein $R_1$, $R_2$, $R_3$, $R_{10}$, X, Boc, and n are as described above].

This reaction uses an alkylborane derivative, such as $BH_3$ or 9-BBN, or a metal hydride complex, such as $(iBu)_2AlH$, $NaBH_4$, and $LiAlH_4$, in particular $LiBH_4$, in a reaction solvent, such as THF, 1,4-dioxane, ethanol, or methanol. The reaction is carried out at a temperature of 0° C. to refluxing temperature and, preferably, at room temperature.

In the synthetic pathway 2, the compound represented by the general formula (1d) can be obtained by acidolysis of the compound of the general formula (9) (Step H).

This reaction is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate.

Of the compounds of the general formula (1), those in which $R_4$ is a lower acyl group having 1 to 5 carbon atoms or a substituted or unsubstituted benzoyl group, and $R_5$, $R_6$, and $R_7$ are each a hydrogen atom are represented by the following general formula (1e):

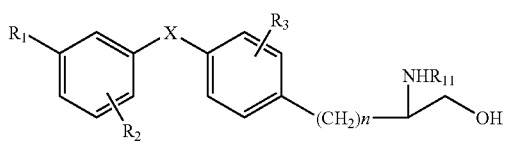  (1e)

[wherein $R_{11}$ is a lower aliphatic acyl group having 1 to 5 carbon atoms or a substituted or unsubstituted benzoyl group; and $R_1$, $R_2$, $R_3$, X, and n are as described above]. These compounds can be produced by the following synthetic pathway 3:

Synthetic pathway 3

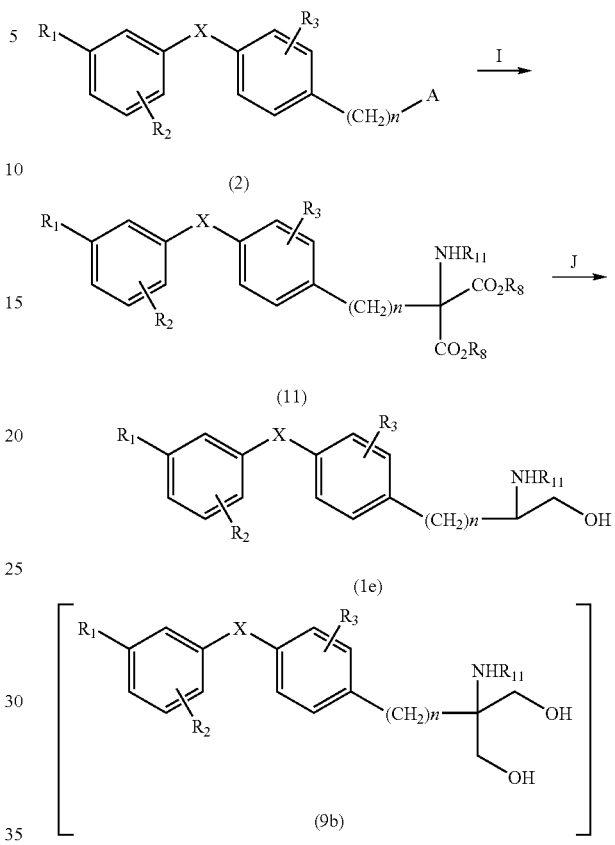

In the synthetic pathway 3, the compound represented by the following general formula (11) can be obtained by reacting the compound represented by the general formula (2) with the compound represented by the general formula (12) in the presence of a base (Step I):

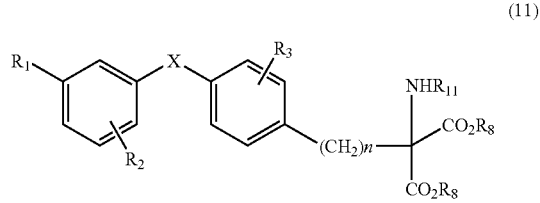  (11)

[wherein $R_1$, $R_2$, $R_3$, $R_8$, $R_{11}$, X, and n are as described above]; and (12)

[wherein $R_8$ and $R_{11}$ are as described above].

This reaction uses a reaction solvent, such as methanol, ethanol, 1,4-dioxane, DMSO, DMF, or THF, and is carried out at a temperature of 0° C. to refluxing temperature, preferably 80° C. to 100° C., in the presence of inorganic base, such as sodium hydride, potassium hydride, sodium alkoxide, potassium alkoxide, potassium carbonate, or sodium carbonate.

In the synthetic pathway 3, the compound represented by the general formula (1e) can be obtained by reducing the compound of the general formula (11) (Step J).

This reaction uses an alkylborane derivative, such as $BH_3$ or 9-BBN, or a metal hydride complex, such as $(iBu)_2AlH$, $NaBH_4$, or $LiAlH_4$, in particular $LiBH_4$, in a reaction solvent, such as THF, 1,4-dioxane, ethanol, or methanol. The reaction is carried out at a temperature of 0° C. to refluxing temperature and, preferably, at room temperature.

Of the compounds of the general formula (1), those in which $R_4$ is a hydrogen atom, a lower aliphatic acyl group having 1 to 5 carbon atoms, or a substituted or unsubstituted benzoyl group, $R_5$ is a lower alkoxymethyl group having 1 to 4 carbon atoms, and $R_6$ is a hydrogen atom are represented by the following general formula (1f):

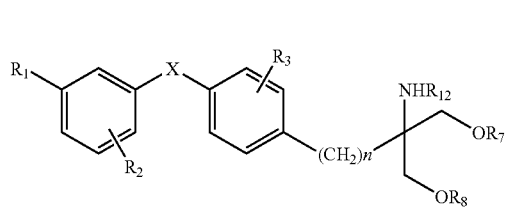

(1f)

[wherein $R_{12}$ is a hydrogen atom, a lower aliphatic acyl group having 1 to 5 carbon atoms, or a substituted or unsubstituted benzoyl group; and $R_1$, $R_2$, $R_3$, $R_7$, $R_8$, X, and n are as described above]. These compounds can be obtained by reacting a diol that results from the synthetic pathway 2 or 3 and is represented by the following general formula (9c), with the compound represented by the following general formula (13), and subsequently subjecting the reaction product to acidolysis, if necessary:

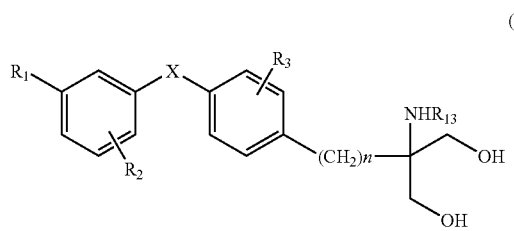

(9c)

[wherein $R_{13}$ is a lower aliphatic acyl group having 1 to 5 carbons, a substituted or unsubstituted benzoyl group or Boc; and $R_1$, $R_2$, $R_3$, X, and n are as described above]; and

$R_8$-A (13)

[wherein $R_8$ and A are as described above].

This reaction may use a reaction solvent such as methylene chloride, THF, or 1,4-dioxane and is carried out at 0° C. to room temperature in the presence of a base, such as triethylamine or pyridine. Preferably, the reaction is carried out at room temperature in acetonitrile and in the presence of silver oxide. When $R_{13}$ in the general formula (9c) is Boc, the acidolysis is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate.

Of the compounds of the general formula (1), those in which $R_5$ is a lower alkoxymethyl group having 1 to 4 carbon atoms or a lower alkylthiomethyl group having 1 to 4 carbon atoms, and $R_4$, $R_6$ and $R_7$ are each a hydrogen atom are represented by the following general formula (1g):

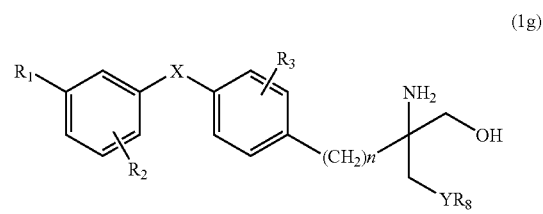

(1g)

[wherein Y represents an oxygen or sulfur atom; and $R_1$, $R_2$, $R_3$, $R_8$, X, and n are as described above]. These compounds can be obtained by the following synthetic pathway:

Synthetic pathway 4

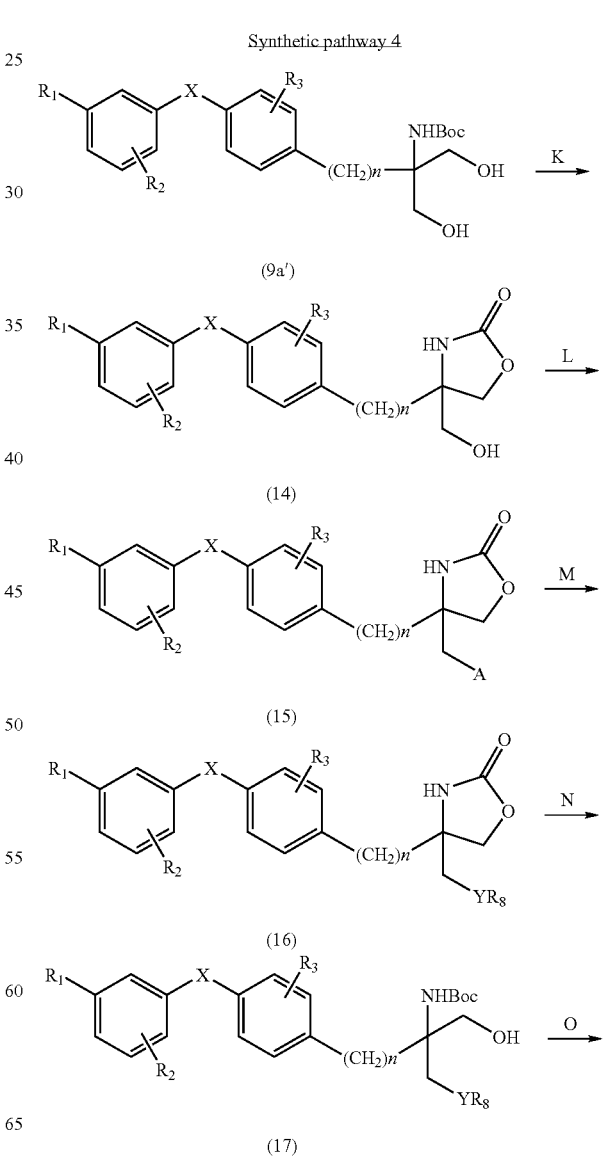

-continued

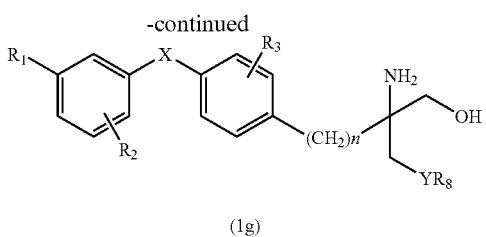

(1g)

In the synthetic pathway 4, the compound represented by the following general formula (14) can be obtained from the compound represented by the following general formula (9a'), which is the general formula (9a) with $R_{10}$ being a hydrogen atom (Step K):

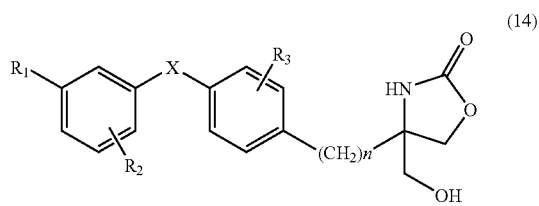

(14)

[wherein $R_1$, $R_2$, $R_3$, X, and n are as described above]; and

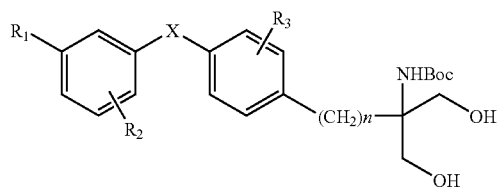

(9a')

[wherein $R_1$, $R_2$, $R_3$, Boc, X, and n are as described above].

This reaction uses a reaction solvent such as THF, 1,4-dioxane, DMF, benzene, or toluene and is carried out at a temperature of 0° C. to refluxing temperature, preferably at room temperature, in the presence of an inorganic base, such as sodium hydride, potassium hydride, sodium alkoxide, or potassium alkoxide. Alternatively, the reaction may be carried out in pyridine solvent while the reaction mixture is refluxed, preferably at 80° C. to 100° C.

In the synthetic pathway 4, the compound represented by the following general formula (15) can be obtained by substituting the hydroxyl group of the compound of the general formula (14) with a halogen atom (Step L):

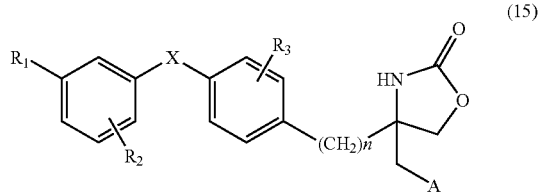

(15)

wherein $R_1$, $R_2$, $R_3$, A, X, and n are as described above.

The reaction uses a reaction solvent such as methylene chloride, THF, or 1,4-dioxane and is carried out at 0° C. to room temperature. Specifically, the compound of the general formula (14) is reacted with carbon tetrachloride, carbon tetrabromide, or iodine in the presence of triphenylphosphine or imidazole. Alternatively, the compound of the general formula (14) may be reacted with para-toluene sulfonyl chloride or methanesulfonyl chloride in a solvent such as methylene chloride, chloroform, or benzene in the presence of an organic base such as pyridine or triethylamine to form a corresponding sulfonic acid ester. The reaction is carried out at 0° C. to 80° C., preferably at room temperature. Subsequently, the resulting sulfonic acid ester is reacted with sodium bromide, potassium bromide, sodium iodide, potassium iodide, potassium fluoride, or sodium fluoride. This reaction uses a reaction solvent such as THF, acetonitrile and, preferably, acetone and is carried out at room temperature to refluxing temperature.

In the synthetic pathway 4, the compound represented by the following general formula (16) can be obtained by reacting the compound of the general formula (15) with the compound represented by the following general formula (18) (Step M):

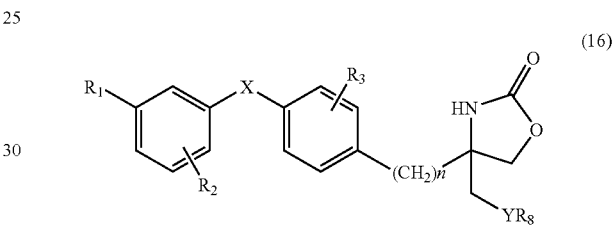

(16)

[wherein $R_1$, $R_2$, $R_3$, $R_8$, X, Y, and n are as described above], and $$R_8—YH \quad (18)$$

[wherein $R_8$ and Y are as described above].

This reaction uses a reaction solvent such as methanol, ethanol, 1,4-dioxane, or DMF and is carried out at 0° C. to room temperature in the presence of an organic base, such as triethylamine or pyridine, or an inorganic base, such as sodium hydride, sodium methoxide, sodium ethoxide, sodium butoxide, or potassium butoxide.

In the reaction pathway 4, the compound represented by the following general formula (17) is obtained by introduction of a Boc group to the compound of the general formula (16), followed by ring-opening of the oxazolidinone ring (Step N):

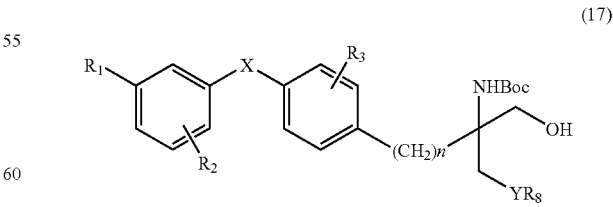

(17)

[wherein $R_1$, $R_2$, $R_3$, $R_8$, X, Y, and n are as described above].

The ring-opening reaction uses a reaction solvent such as THF or 1,4-dioxane, preferably acetonitrile and is carried out under typical Boc-adding conditions. Preferably, the reaction is carried out by first applying Boc$_2$O at room temperature to 80° C. in the presence of dimethylaminopyridine to form a Boc-added form and subsequently opening the oxazolidinone ring at room temperature in methanol solvent in the presence of cesium carbonate.

In the synthetic pathway 4, the compound represented by the general formula (1g) can be obtained by acidolysis of the compound of the general formula (17) (Step O).

This reaction is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate.

Of the compounds of the general formula (1), those in which R$_4$ is a phenyl group and R$_6$ is a hydrogen atom are represented by the following general formula (1h):

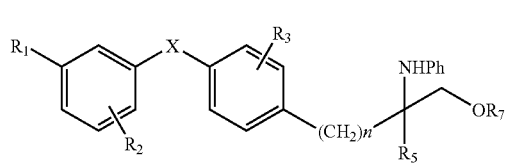

(1h)

[wherein R$_1$, R$_2$, R$_3$, R$_5$, X, and n are as described above]. These compounds can be obtained by reacting the compound represented by the following general formula (1i) with a phenyl bismuth reagent:

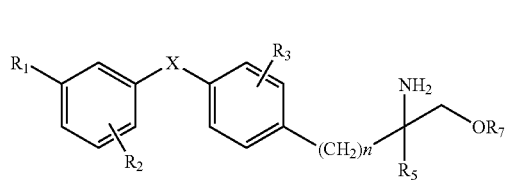

(1i)

[wherein R$_1$, R$_2$, R$_3$, R$_5$, R$_7$, X, and n are as described above].

Preferably, this reaction uses methylene chloride as a reaction solvent and is carried out at room temperature by adding Ph$_3$Bi(OAc)$_2$ and, if necessary, molecular sieves, in the presence of copper acetate.

Of the compounds of the general formula (1), those in which R$_4$ is a hydrogen atom, a lower aliphatic acyl group having 1 to 5 carbon atoms, or a substituted or unsubstituted benzoyl group, R$_5$ is a lower alkenyl group having 2 to 4 carbon atoms, and R$_6$ and R$_7$ are each a hydrogen atom are represented by the following general formula (1j):

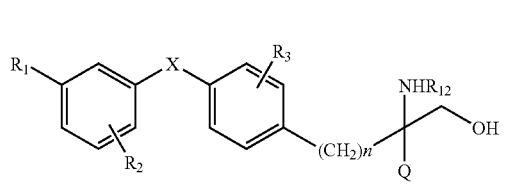

(1j)

[wherein Q is a lower alkenyl group having 2 to 4 carbon atoms, and R$_1$, R$_2$, R$_3$, R$_{12}$, X, and n are as described above].

These compounds can be obtained by first protecting one of the hydroxyl groups of the compound of the general formula (9c), subsequently oxidizing the remaining hydroxyl group to an aldehyde, forming an alkenyl group by the Wittig reaction, and performing deprotection, if necessary.

Specifically, one of the hydroxyl groups is first protected by a common hydroxyl-protecting group, including an acyl-type protecting group, such as acetyl and benzoyl, a silyl-type protecting group, such as t-butyldimethylsilyl and t-butyl-diphenylsilyl, and an alkyl-type protecting group, such as benzyl. DMSO oxidation is then performed to obtain an aldehyde. This is carried out by using an oxidizing agent, including chromium oxide-pyridine complex, such as pyridinium chlorochromate or pyridinium dichromate, a metal oxidizing agent, such as chromium oxide, silver carbonate, or manganese dioxide, or a DMSO activating agent, such as oxalyl chloride, trifluoroacetic anhydride, acetic anhydride, DCC, or sulfur trioxide-pyridine complex. The aldehyde is then subjected to Wittig reaction. The Wittig reaction uses a reaction solvent such as THF, ether, DMSO, or 1,4-dioxane in conjunction with a phosphonium salt having a lower alkyl group such as methyl, ethyl, propyl isopropy, or butyl and is carried out at −78° C. to room temperature in the presence of a base, such as sodium hydride, potassium hydride, sodium butoxide, potassium butoxide, or lithium diisopropylamide. When an acyl-type protecting group is used, the subsequent deprotection of hydroxyl group uses a reaction solvent such as methanol, ethanol, 1,4-dioxane, DMSO, DMF, or THF and is carried out at 0° C. to room temperature in the presence of a base, such as an aqueous solution of sodium hydroxide, potassium hydroxide, or lithium hydroxide. When a silyl-type protecting group is used, THF, DMF or 1,4-dioxane is used as a solvent and the deprotection reaction is carried out by applying potassium fluoride, cesium fluoride, or tetrabutylammonium fluoride at 0° C. to room temperature. For a benzyl protecting group, the deprotection is carried out by a common contact reduction process. For a methoxymethyl protecting group, the deprotection is carried out in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. When R$_{13}$ in the general formula (9c) is a Boc group, it may be removed by carrying out acidolysis in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate.

Of the compounds of the general formula (1), those in which R$_4$ is a hydrogen atom, a lower aliphatic acyl group having 1 to 5 carbon atoms, or a substituted or unsubstituted benzyl group, R$_6$ is a lower alkyl group having 1 to 4 carbon atoms, and R$_7$ is a hydrogen atom are represented by the following general formula (1k):

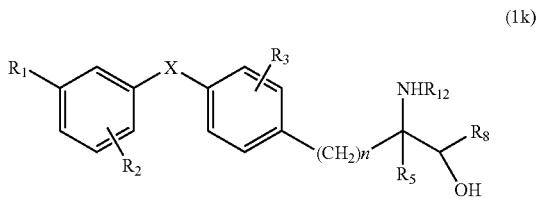

(1k)

[wherein $R_1$, $R_2$, $R_3$, $R_5$, $R_8$, $R_{12}$, X, and n are as described above]. These compounds can be obtained by oxidizing the compound represented by the following general formula (11) to an aldehyde, reacting the aldehyde with an organometal reagent, and performing deprotection, if necessary:

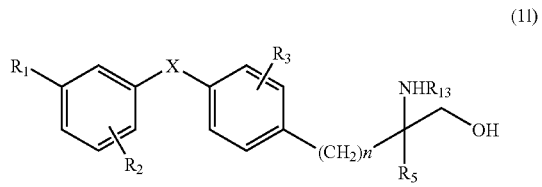

(11)

[wherein $R_1$, $R_2$, $R_3$, $R_5$, $R_8$, $R_{13}$, X, and n are as described above].

The oxidation can be carried out by using any methods commonly used for oxidizing an alcohol to an aldehyde. One example is the DMSO oxidation using an oxiding agent, including a chromium oxide-pyridine complex, such as pyridinium chlorochromate or pyridinium dichromate, a metal oxiding agent, such as chromium oxide, silver carbonate and manganese dioxide, or a DMSO activating agent, such as oxalyl chloride, trifluuoroacetic anhydride, acetic anhydride, DCC and sulfur trioxide-pyridine complex. The resulting aldehyde is reacted with a lower alkyl lithium or a lower alkyl Grignard reagent having methyl, ethyl, propyl, isopropyl, or butyl. The reaction is carried out at 0° C. to room temperature in a reaction solvent such as THF, ether, or 1,4-dioxane. When $R_{13}$ is a Boc group, the deprotection is carried out at 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. When $R_{13}$ is a lower aliphatic acyl group or a substituted or unsubstituted benzoyl group that requires deprotection, the deprotection is carried out at 0° C. to refluxing temperature, preferably at 80° C. to 100° C., in a reaction solvent such as methanol, ethanol, 1,4-dioxane, DMSO, DMF, or THF and in the presence of a base such as an aqueous solution of sodium hydroxide, potassium hydroxide, or lithium hydroxide.

The compound represented by the general formula (1k) can also be obtained by the following alternative synthetic pathway:

Synthetic pathway 5

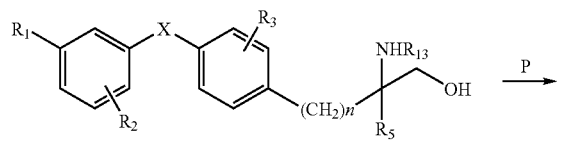

(11)

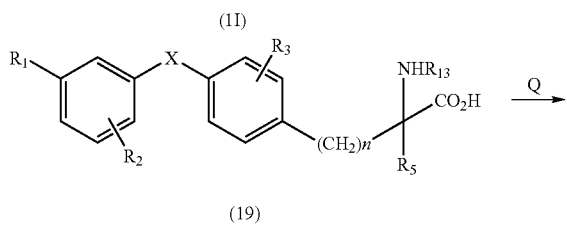

(19)

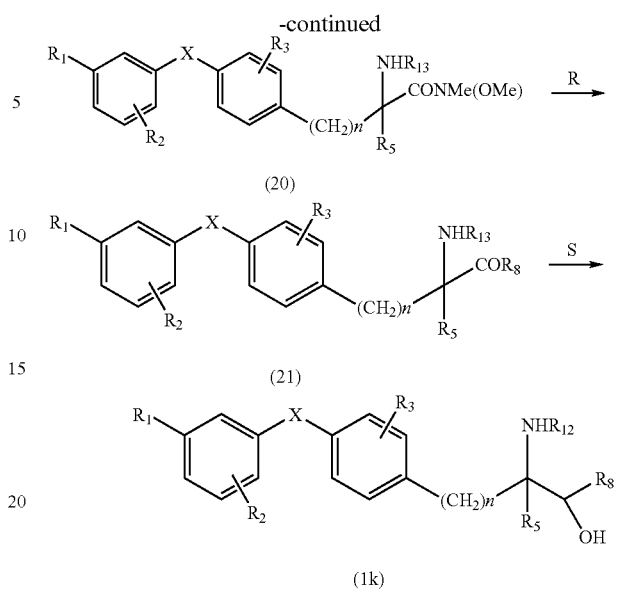

(20)

(21)

(1k)

In the synthetic pathway 5, the compound represented by the following general formula (19) can be obtained by oxidation of the compound of the general formula (11) (Step P):

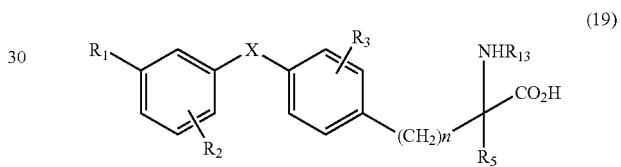

(19)

[wherein $R_1$, $R_2$, $R_3$, $R_5$, $R_{13}$, X, and n are as described above].

This reaction uses an oxidizing agent, such as potassium permanganate, lead tetraacetate, luthenium tetraoxide, or, preferably, chromium oxide-pyridine complex, such as pyridinium chlorochromate or pyridinium dichromate, and is carried out at 0° C. to room temperature in a reaction solvent, such as acetone, DMF, methylene chloride, chloroform, ethyl acetate, or acetic acid.

In the synthetic pathway 5, the compound represented by the following general formula (20) can be obtained by condensation of N,O-dimethylhydroxylamine with the compound of the general formula (19) (Step Q):

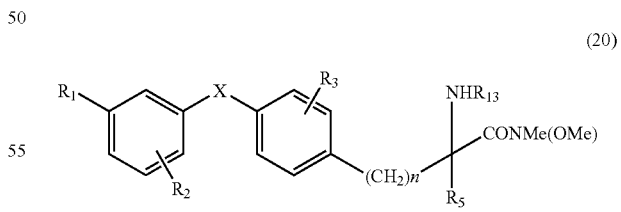

(20)

[wherein $R_1$, $R_2$, $R_3$, $R_5$, $R_{13}$, X, and n are as described above].

This reaction can be carried out by using acid anhydride mixture method or active ester method, each commonly used in forming peptide bonds, and preferably involves a condensation agent. Specifically, the reaction uses a reaction solvent such as THF, DMSO, DMF, or methylene chloride and is carried out at 0° C. to room temperature in the presence of an organic base such as triethylamine or pyridine, along with a condensation agent such as dicyclohexylcarbodiimide (DCC), diisopropylcarbodiimide (DIPC), DPPA, diethylphosphonylcyanide (DEPC), 1-ethyl-3-(3-dimethylaminopropyl)carbodiimide (WSC), with 4-dimethylaminopyridine (DMAP) optionally added as a catalyst.

In the synthetic pathway 5, the compound represented by the following general formula (21) can be obtained by reacting the compound of the general formula (20) with the compound represented by the following general formula (22) (Step R):

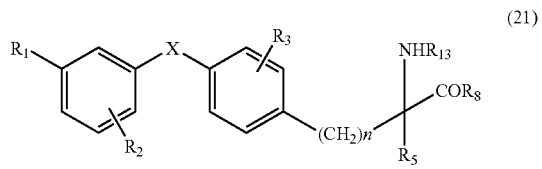
(21)

[wherein $R_1$, $R_2$, $R_3$, $R_5$, $R_8$, $R_{13}$, X, and n are as described above]; and

$R_8$-M      (22)

[wherein M represents Li, MgCl, MgBr, or MgI and $R_8$ is as described above].

The reaction uses a organic solvent such as ether, 1,4-dioxane, or THF and is carried out at −78° C. to room temperature.

In the synthetic pathway 5, the compound represented by the general formula (1k) can be obtained by reducing the compound of the general formula (21), followed, if necessary, by deprotection.

This reaction uses an alkylborane derivative, such as $BH_3$ or 9-BBN, or a metal hydride complex, such as $(iBu)_2AlH$, $NaBH_4$, or $LiAlH_4$, in particular, $LiBH_4$, in a reaction solvent such as THF, 1,4-dioxane, ethanol, or methanol. The reaction is carried out at a temperature of 0° C. to refluxing temperature and, preferably, at room temperature. When $R_{13}$ is a Boc group, the deprotection is carried out at 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. When $R_{13}$ is a lower aliphatic acyl group or a substituted or unsubstituted benzoyl group that requires deprotection, the deprotection is carried out at 0° C. to refluxing temperature, preferably at 80° C. to 100° C., in a reaction solvent such as methanol, ethanol, 1,4-dioxane, DMSO, DMF, or THF and in the presence of a base such as an aqueous solution of sodium hydroxide, potassium hydroxide, or lithium hydroxide.

Of the compounds of the general formula (1), those in which $R_4$ is a lower acyl group having 1 to 5 carbon atoms or a substituted or unsubstituted benzyl group are represented by the following general formula (1m):

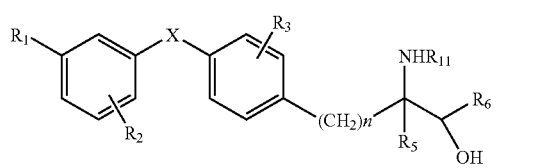
(1m)

[wherein $R_1$, $R_2$, $R_3$, $R_5$, $R_6$, $R_{11}$, X, and n are as described above]. These compounds can be obtained by the condensation of the compound represented by the following general formula (1n) with the compound represented by the following general formula (23):

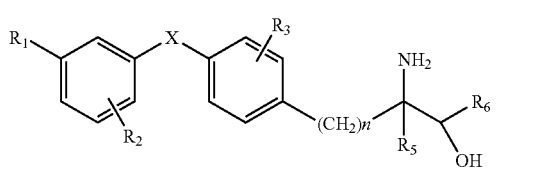
(1n)

[wherein $R_1$, $R_2$, $R_3$, $R_5$, $R_6$, X, and n are as described above]; and

(23)

[wherein $R_{14}$ is a lower alkyl group having 1 to 4 carbon atoms or a substituted or unsubstituted phenyl group; and Z is a halogen atom or a hydroxyl group].

When Z in the general formula (23) is a hydroxyl group, the reaction can be carried out by using acid anhydride mixture method or active ester method, each commonly used in forming peptide bonds, and preferably involves a condensation agent. Specifically, the reaction uses a reaction solvent such as THF, DMSO, DMF, or methylene chloride and is carried out at 0° C. to room temperature in the presence of an organic base such as triethylamine or pyridine, along with a condensation agent such as DCC, DIPC, DPPA, DEPC, or WSC, with DMAP optionally added as a catalyst.

When Z in the general formula (23) is a halogen atom, the reaction uses a reaction solvent such as THF, methylene chloride, or 1,4-dioxane and is carried out at 0° C. to room temperature in the presence of an organic base such as triethylamine or pyridine.

Of the compounds of the general formula (1), those in which $R_4$ is a lower alkyl group having 1 to 4 carbon atoms or a substituted or unsubstituted benzyl group are represented by the following general formula (1o):

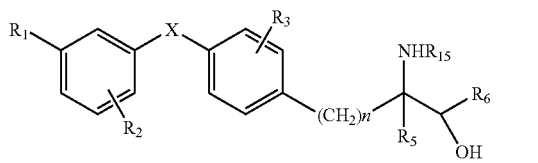
(1o)

[wherein $R_{15}$ is a lower alkyl group having 1 to 4 carbon atoms or a substituted or unsubstituted benzyl group; and $R_1$, $R_2$, $R_3$, $R_5$, $R_6$, X, and n are as described above]. These compounds can be obtained by reducing the compound of the general formula (1m).

This reaction uses a metal hydride complex, such as $BH_3$, $NaBH_4$, or $LiBH_4$, in particular, $LiAlH_4$, along with a reaction solvent such as THF or 1,4-dioxane. The reaction is carried out at a temperature of 0° C. to refluxing temperature.

Of the compounds of the general formula (1), those in which $R_5$ is a hydroxyethyl group, and $R_4$, $R_6$ and $R_7$ are each a hydrogen atom are represented by the following general formula (1p):

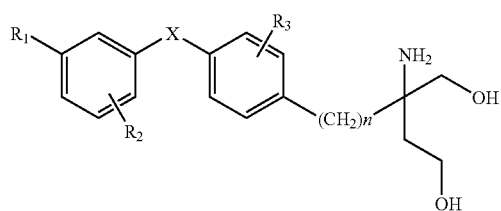

[wherein $R_1$, $R_2$, $R_3$, X, and n are as described above]. These compounds can be obtained by the following synthetic pathway:

[wherein $R_{16}$ is a methanesulfonyl or toluenesulfonyl group; and $R_1$, $R_2$, $R_3$, X, and n are as described above].

This reaction may be solvent-free or may use an organic solvent such as methylene chloride, chloroform, benzene, toluene, or THF and is carried out at 0° C. to room temperature in the presence of an organic base such as triethylamine, diisopropylethylamine, or pyridine.

In the synthetic pathway 6, the compound represented by the following general formula (25) can be obtained by reacting the compound of the general formula (24) with sodium cyanide or potassium cyanide (Step U):

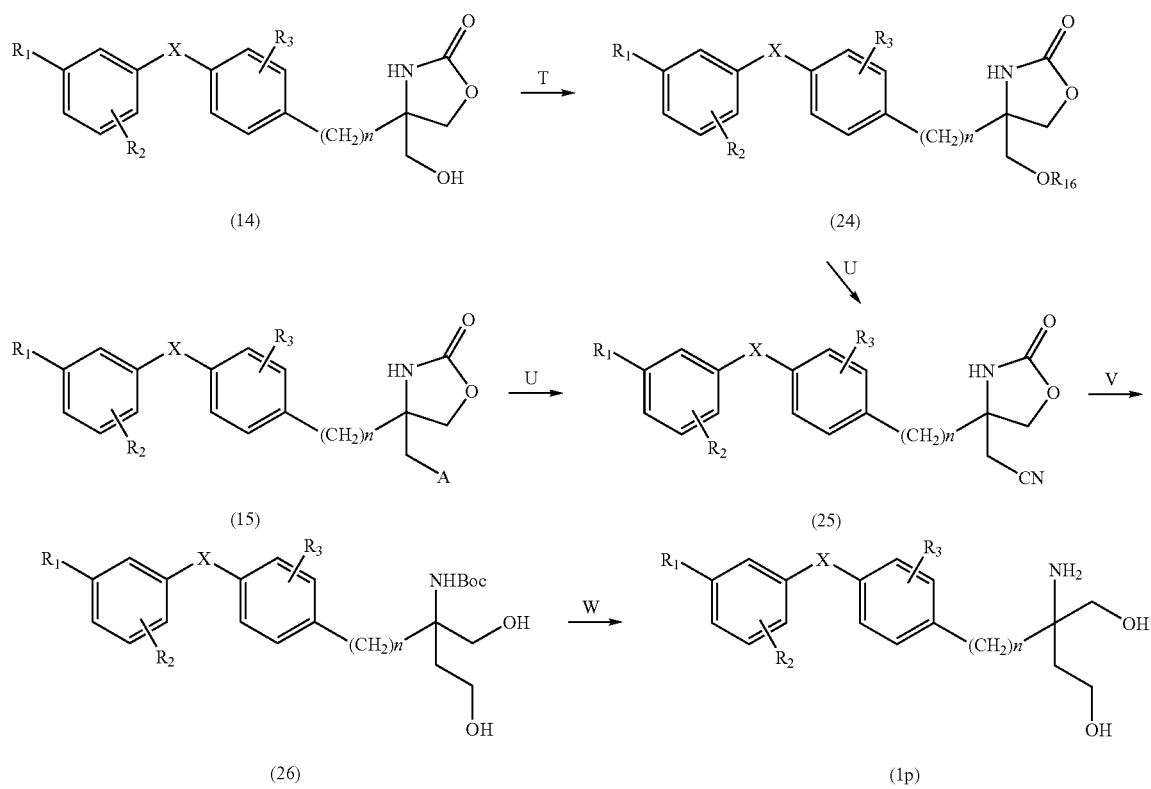

In the synthetic pathway 6, the compound represented by the following general formula (24) can be obtained by reacting the compound of the general formula (14) with methanesulfonyl chloride or p-toluenesulfonyl chloride (Step T):

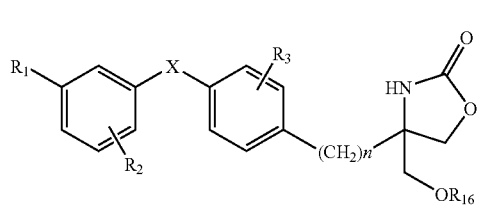

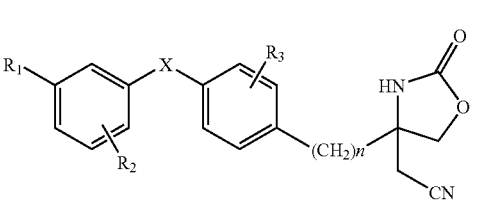

[wherein $R_1$, $R_2$, $R_3$, X, and n are as described above].

This reaction uses a solvent such as 1,4-dioxane, DMSO, or DMF and is carried out at room temperature to 80° C. and, if necessary, in the presence of water.

In the synthetic pathway 6, the compound represented by the following general formula (26) can be obtained either by hydrolysis of the compound of the general formula (25), followed by introduction of a Boc group and reduction, or by introduction of a Boc group to the compound of the general formula (25), followed by ring-opening of the oxazolidinone ring and reduction, as shown in Step N (Step V):

(26)

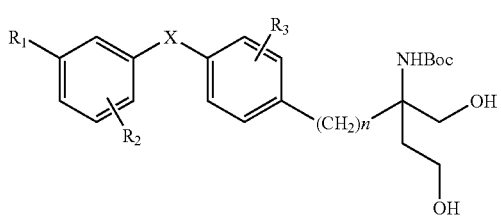

[wherein $R_1$, $R_2$, $R_3$, Boc, X, and n are as described above].

This reaction uses a reaction solvent such as methanol, ethanol, 1,4-dioxane, DMSO, DMF, or THF and is carried out at 0° C. to refluxing temperature, preferably at 80° C. to 100° C., in the presence of a base, such as an aqueous solution of sodium hydroxide, potassium hydroxide, or lithium hydroxide. Subsequently, $Boc_2O$ is applied at room temperature, to carry out a typical process for adding Boc group. The reaction is then carried out at 0° C. to refluxing temperature in the presence of a metal hydride complex, such as $BH_3$, $NaBH_4$, or $LiBH_4$, in particular $LiAlH_4$, in a reaction solvent such as THF or 1,4-dioxane. Alternatively, using a reaction solvent such as THF or 1,4-dioxane, preferably acetonitrile, $Boc_2O$ is applied at room temperature to 80° C., preferably in the presence of dimethylamino pyridine, to obtain a Boc-added form, which is followed by ring-opening of the oxazolidinone ring, carried out at room temperature in the presence of cesium carbonate in methanol as a solvent. The reaction is then carried out at 0° C. to refluxing temperature in the presence of a metal hydride complex, such as $BH_3$, $NaBH_4$, or $LiBH_4$, in particular $LiAlH_4$, in a reaction solvent such as THF or 1,4-dioxane.

In the synthetic pathway 6, the compound represented by the general formula (1p) can be obtained by acidolysis of the compound of the general formula (26) (Step W).

This reaction is carried out at a temperature of 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate.

Of the compounds of the general formula (1), those in which $R_5$ is a hydroxypropyl group, $R_4$ is a hydrogen atom, a lower alkyl group having 1 to 4 carbon atoms, a phenyl, or a substituted or unsubstituted benzyl group, and $R_6$ and $R_7$ are each a hydrogen atom are represented by the following general formula (1q):

(1q)

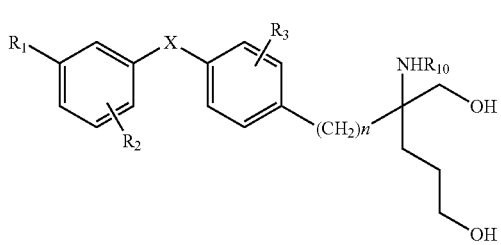

[wherein $R_1$, $R_2$, $R_3$, $R_{10}$, X, and n are as described above]. These compounds can be obtained by the following synthetic pathway:

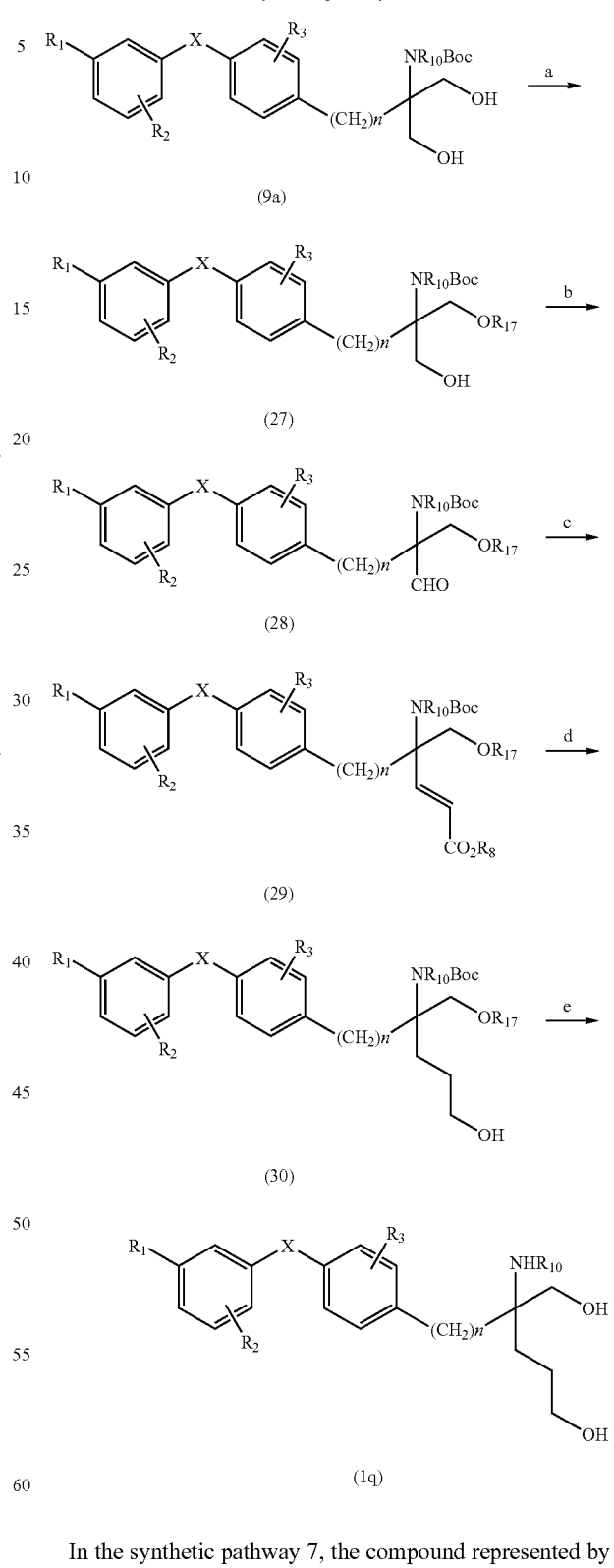

In the synthetic pathway 7, the compound represented by the following general formula (27) can be obtained by reacting the compound of the general formula (9a) with methoxymethyl chloride, t-butyldimethylsilyl chloride, t-butyldiphenylsilyl chloride, or triisopropylsilyl chloride (Step a):

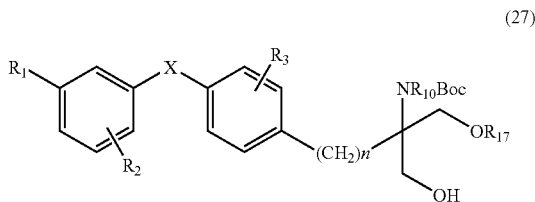

(27)

[wherein $R_{17}$ is a methoxymethyl group, a t-butyldimethylsilyl group, a t-butyldiphenylsilyl group, or a triisopropylsilyl group; and $R_1$, $R_2$, $R_3$, $R_{10}$, Boc, X, and n are as described above].

This reaction uses an organic solvent such as acetonitrile, THF, methylene chloride, or chloroform and is carried out at 0° C. to room temperature in the presence of an organic base such as triethylamine or diisopropylethylamine.

In the synthetic pathway 7, the compound represented by the following general formula (28) can be obtained by oxidation of the compound of the general formula (27) (Step b):

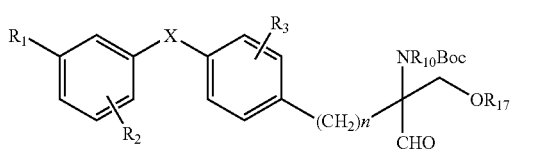

(28)

wherein $R_1$, $R_2$, $R_3$, $R_{10}$, $R_{17}$, Boc, X, and n are as described above.

This reaction is carried out by performing DMSO oxidation using an oxidizing agent, including chromium oxide-pyridine complex, such as pyridinium chlorochromate or pyridinium dichromate, a metal oxidizing agent, such as chromium oxide, silver carbonate, or manganese dioxide, or a DMSO activating agent, such as oxalyl chloride, trifuluoroacetic anhydride, acetic anhydride, DCC and sulfur trioxide-pyridine complex.

In the synthetic pathway 7, the compound represented by the following general formula (29) can be obtained by reacting the compound of the general formula (28) with the compound represented by the following general formula (31) in the presence of a base (Step c):

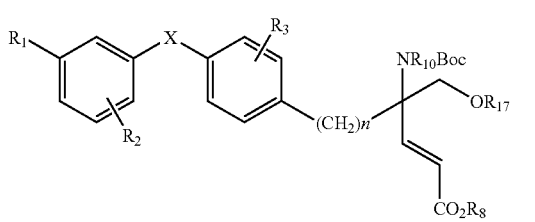

(29)

[wherein $R_1$, $R_2$, $R_3$, $R_8$, $R_8$, $R_{10}$, $R_{10}$, $R_{17}$, Boc, X, and n are as described above]; and

(31)

[wherein $R_8$ is as described above].

This reaction is carried out by first reacting the compound of the general formula (31) with a base such as sodium hydride, potassium hydride, sodium butoxide, or potassium butoxide at 0° C. to room temperature in an organic solvent such as THF, DMSO, or 1,4-dioxane, and subsequently applying the compound of the general formula (29).

In the synthetic pathway 7, the compound represented by the following general formula (30) can be obtained by reducing the compound of the general formula (29) (Step d):

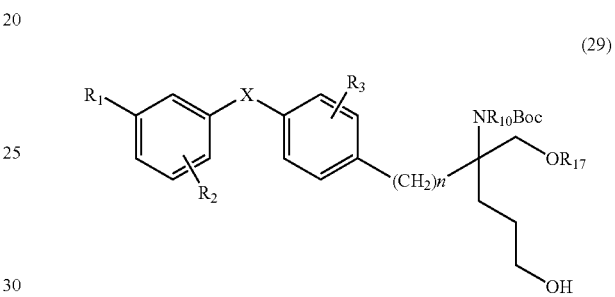

(29)

[wherein $R_1$, $R_2$, $R_3$, $R_{10}$, $R_{17}$, Boc, X, and n are as described above].

This reaction is carried out by first reducing the double bonds at room temperature to 100° C. under a hydrogen pressure of atmospheric or higher pressure in the presence of a reduction catalyst, such as palladium carbon, platinum carbon, platinum oxide, rhodium carbon, or ruthenium carbon, in a solvent such as ethanol, methanol, THF, DMF, or ethyl acetate. Subsequently, the ester bonds are reduced by using an alkylborane derivative, such as $BH_3$ or 9-BBN, or a metal hydride complex, such as $(iBu)_2AlH$, $NaBH_4$, $LiBH_4$, or $LiAlH_4$ in a reaction solvent such as 1,4-dioxane, ethanol, or methanol and, preferably, THF.

In the synthetic pathway 7, the compound represented by the general formula (1q) can be obtained by acidolysis of the compound of the general formula (30) (Step e).

When $R_{17}$ is a silyl protective group, this reaction is carried out by first applying tetrabutylammonium fluoride or potassium fluoride in a THF solvent at 0° C. to room temperature. Subsequently, the acidolysis is carried out at 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. When $R_{17}$ is a methoxymethyl protective group, the compound of the general formula (30) is directly subjected to acidolysis.

Of the compounds of the general formula (1), those in which $R_5$ is a monohalogenated methyl group, and $R_4$, $R_6$, and $R_7$ are each a hydrogen atom are represented by the following general formula (1r):

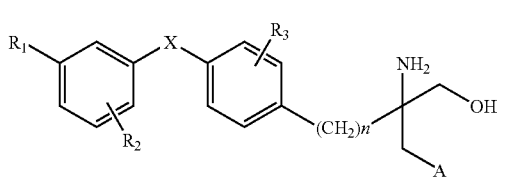

(1r)

[wherein $R_1$, $R_2$, $R_3$, A, X, and n are as described above]. These compounds can be obtained by the following synthetic pathway:

of the compound of the general formula (32) (Step h) or by hydrolysis of the compound of the general formula (15) (Step g).

The acidolysis of the compound of the general formula (32) is carried out at 0° C. to room temperature in an inorganic or organic acid, such as acetic acid, hydrochloric acid, hydrobromic acid, methanesulfonic acid, or trifluoroacetic acid, or in a mixture with an organic solvent, such as methanol, ethanol, THF, 1,4-dioxane, or ethyl acetate. The hydrolysis of the compound of the general formula (15) is carried out at a temperature of 0° C. to refluxing temperature, preferably at 80° C. to 100° C., in the presence of a base, such as aqueous solution of sodium hydroxide, potassium hydroxide, or Synthetic pathway 8

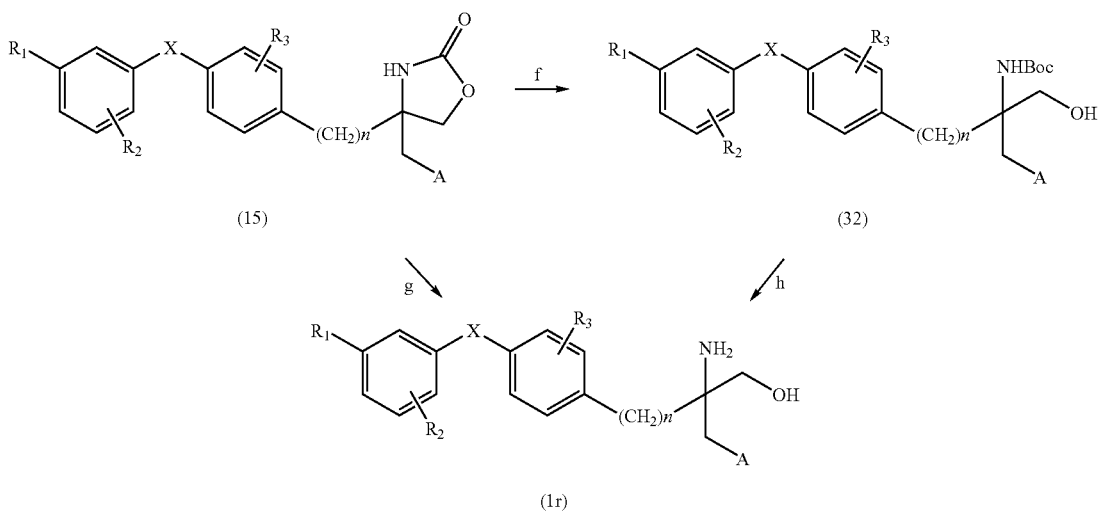

In the synthetic pathway 8, the compound represented by the following general formula (32) can be obtained by the introduction of Boc group to the compound of the general formula (15), followed by ring-opening of the oxazolidinone ring (Step f):

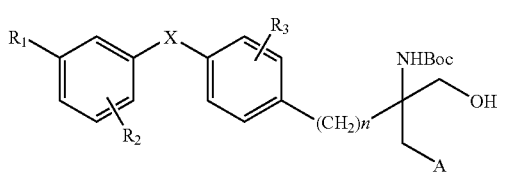

(32)

[wherein $R_1$, $R_2$, $R_3$, A, Boc, X, and n are as described above].

This reaction uses a reaction solvent such as THF, 1,4-dioxane, or, preferably, acetonitrile and is carried out under typical conditions for Boc introduction. Preferably, $Boc_2O$ is applied at room temperature to 80° C. to obtain a Boc-added form, which is followed by ring-opening of the oxazolidinone ring, carried out at room temperature in the presence of cesium carbonate in methanol.

In the synthetic pathway 8, the compound represented by the general formula (1r) can be obtained either by acidolysis lithium hydroxide, and in a reaction solvent such as methanol, ethanol, 1,4-dioxane, DMSO, DMF, or THF.

Of the compounds represented by each general formula, those in which X is SO or $SO_2$ can also be obtained by oxidation of the corresponding compounds in which X is S.

This reaction uses a reaction solvent such as 1,4-dioxane, DMSO, DMF, THF, methylene chloride, or chloroform, along with an oxidizing agent such as potassium permanganate, meta-chloroperbenzoic acid, or aqueous hydrogen peroxide, and is carried out at 0° C. to refluxing temperature and, preferably, at room temperature.

Reference Example 1

2-chloro-4-[(3-trifluoromethyl)phenylthio]benzaldehyde

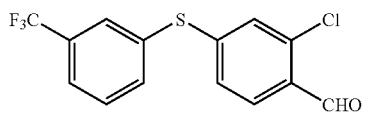

To a DMF solution (20 mL) of 2-chloro-4-fluorobenzaldehyde (1.15 g) and 3-(trifluoromethyl)thiophenol (1.33 g), potassium carbonate (2.76 g) was added and the mixture was stirred at 120° C. for 1 hour while heated. The reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=10:1). This gave the desired product as a pale yellow oil (1.96 g).

Reference Examples 2 through 32

Similarly, different thiophenols and phenols were used to synthesize the different compounds shown in Table 1 below.

TABLE 1

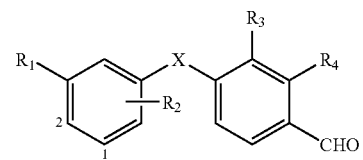

| Reference Examples | R1 | R2 | R3 | R4 | X |
|---|---|---|---|---|---|
| 2 | Cl | 1-Cl | H | Cl | O |
| 3 | t-Bu | 1-H | H | H | O |
| 4 | $CF_3$ | 1-H | H | H | O |
| 5 | $CF_3$ | 1-H | OMe | H | O |
| 6 | $CF_3$ | 1-H | H | OMe | O |
| 7 | $CF_3$ | 1-H | H | $OCH_2Ph$ | O |
| 8 | $CF_3$ | 1-H | $CF_3$ | H | O |
| 9 | $CF_3$ | 1-H | H | $CF_3$ | O |
| 10 | $CF_3$ | 1-$CF_3$ | H | H | O |
| 11 | $CF_3$ | 1-$CF_3$ | H | Cl | O |
| 12 | $CF_3$ | 2-Cl | H | H | O |
| 13 | $CF_3$ | 1-MeO | H | Cl | O |
| 14 | $Ph(CH_2)_2$ | 1-H | H | Cl | O |
| 15 | $Ph(CH_2)_2$ | 1-H | H | $CF_3$ | O |
| 16 | $Ph(CH_2)_2$ | 1-$CF_3$ | H | H | O |
| 17 | $Ph(CH_2)_2$ | 1-$Ph(CH_2)_2$ | H | H | O |
| 18 | $Ph(CH_2)_2$ | 1-$Ph(CH_2)_2$ | H | $CF_3$ | O |
| 19 | $Ph(CH_2)_2$ | 1-$Ph(CH_2)_2$ | H | Cl | O |
| 20 | i-PrO | 1-iPr | H | Cl | O |
| 21 | PhO | 1-H | H | Cl | O |
| 22 | $PhCH_2O$ | 1-H | H | H | O |
| 23 | $PhCH_2O$ | 1-H | H | Br | O |
| 24 | $PhCH_2O$ | 1-H | H | SMe | O |
| 25 | $PhCH_2O$ | 1-H | H | Me | O |
| 26 | $PhCH_2O$ | 1-H | H | Et | O |
| 27 | MeO | 1-$CF_3$ | H | H | O |
| 28 | MeS | 1-H | H | H | O |
| 29 | Cl | 1-Cl | H | H | S |
| 30 | $CF_3$ | 1-$CF_3$ | H | Cl | S |
| 31 | MeO | 1-H | H | Cl | S |

Reference Example 32

Ethyl 2'-chloro-4'-[(3-trifluoromethyl)phenylthio]cinnamate

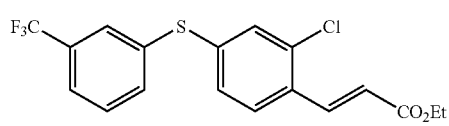

At 0° C. and under a stream of argon gas, 60% sodium hydride (272 mg) was added to a THF solution (30 mL) of diethylphosphono ethyl acetate (1.35 mL). The mixture was stirred for 30 min and a THF solution (15 mL) of the compound of Reference Example 1 (1.96 g) was added dropwise. The mixture was stirred for 2 hours while kept at the same temperature, which was followed by addition of water and extraction with ethyl acetate. The extract was washed sequentially with water and a saturated aqueous solution of sodium chloride, and the organic phase was dried over anhydrous sodium sulfate. The solvent was removed under reduced pressure and the residue was purified on a silica gel column chromatography (hexane:ethyl acetate=10:1). This gave the desired product as a colorless oil (1.72 g).

Reference Examples 33 through 62

Similarly, the compounds of Reference Examples 2 through 31 were used to synthesize the compounds shown in Table 2 below.

TABLE 2

| Reference Examples | R1 | R2 | R3 | R4 | X |
|---|---|---|---|---|---|
| 33 | Cl | 1-Cl | H | Cl | O |
| 34 | t-Bu | 1-H | H | H | O |
| 35 | $CF_3$ | 1-H | H | H | O |
| 36 | $CF_3$ | 1-H | OMe | H | O |
| 37 | $CF_3$ | 1-H | H | OMe | O |
| 38 | $CF_3$ | 1-H | H | $OCH_2Ph$ | O |
| 39 | $CF_3$ | 1-H | $CF_3$ | H | O |
| 40 | $CF_3$ | 1-H | H | $CF_3$ | O |
| 41 | $CF_3$ | 1-$CF_3$ | H | H | O |
| 42 | $CF_3$ | 1-$CF_3$ | H | Cl | O |
| 43 | $CF_3$ | 2-Cl | H | H | O |
| 44 | $CF_3$ | 1-MeO | H | Cl | O |
| 45 | $Ph(CH_2)_2$ | 1-H | H | Cl | O |
| 46 | $Ph(CH_2)_2$ | 1-H | H | $CF_3$ | O |
| 47 | $Ph(CH_2)_2$ | 1-$CF_3$ | H | H | O |
| 48 | $Ph(CH_2)_2$ | 1-$Ph(CH_2)_2$ | H | H | O |
| 49 | $Ph(CH_2)_2$ | 1-$Ph(CH_2)_2$ | H | $CF_3$ | O |
| 50 | $Ph(CH_2)_2$ | 1-$Ph(CH_2)_2$ | H | Cl | O |
| 51 | i-PrO | 1-iPr | H | Cl | O |
| 52 | PhO | 1-H | H | Cl | O |
| 53 | $PhCH_2O$ | 1-H | H | H | O |
| 54 | $PhCH_2O$ | 1-H | H | Br | O |
| 55 | $PhCH_2O$ | 1-H | H | SMe | O |
| 56 | $PhCH_2O$ | 1-H | H | Me | O |
| 57 | $PhCH_2O$ | 1-H | H | Et | O |
| 58 | MeO | 1-$CF_3$ | H | H | O |
| 59 | MeS | 1-H | H | H | O |
| 60 | Cl | 1-Cl | H | H | S |
| 61 | $CF_3$ | 1-$CF_3$ | H | Cl | S |
| 62 | MeO | 1-H | H | Cl | S |

Reference Example 63

Methyl 4'-(3-ethylphenoxy)cinnamate

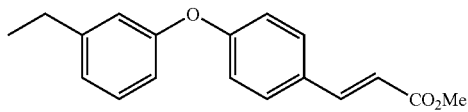

To a DMF solution (50 mL) of 3-ethylphenol (1.13 g) and methyl 4'-fluorocinnamate (834 mg), potassium carbonate (1.92 g) was added and the mixture was stirred at 140° C. for 8 hour while heated. The reaction mixture was poured into water and was extracted with ethyl acetate. The extract was washed sequentially with water and a saturated aqueous solution of sodium chloride and the organic phase was dried over anhydrous sodium sulfate. The solvent was removed under reduced pressure and the resulting residue was purified on a silica gel column chromatography (hexane:ethyl acetate=30:1). This gave the desired product as a yellow oil (540 mg).

Reference Example 64

Ethyl 2'-chloro-4'-(3-trifluoromethylphenylthio)dihydrocinnamate

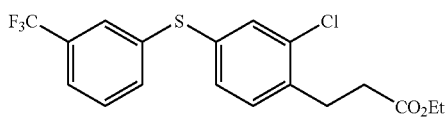

The compound of Reference Example 32 (1.72 g) was dissolved in ethanol (70 mL). While the solution was stirred at 0° C., bismuth chloride (703 mg) was added. Subsequently, sodium borohydride (673 mg) was added in small portions and the mixture was stirred for 1 hour at this temperature and 3 hours at room temperature. Ice water was added and the separated insoluble inorganic residue was removed by filtration through Celite. The filtrate was extracted with ethyl acetate and the extract was washed sequentially with water and a saturated aqueous solution of sodium chloride. The organic phase was then dried over anhydrous sodium sulfate. The solvent was removed under reduced pressure to give the desired product as a colorless oil (1.50 g) (Process A).

Reference Example 65

Methyl 4'-(3-ethylphenoxy)dihydrocinnamate

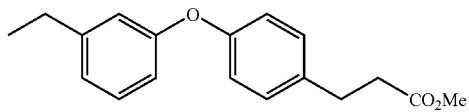

The compound of Reference Example 63 (540 mg) was dissolved in ethanol (20 mL) and 10%-Pd/C (80.0 mg) was added. Under hydrogen, the mixture was stirred at room temperature for 3 hours. The catalyst was removed by filtration and the filtrate was concentrated under reduced pressure to give the desired product as a colorless oil (Process B).

Reference Example 66

Ethyl 2'-benzyloxy-4'-[(3-trifluoromethyl)phenoxy]dihydrocinnamate

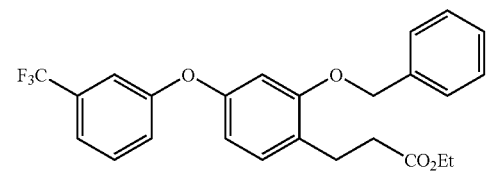

The compound of Reference Example 38 (2.29 g) was dissolved in ethyl acetate (30 mL) and 5%-Pd/C-ethylenediamine complex (230 mg) was added. Under hydrogen, the mixture was stirred at room temperature for 3.5 hours. The catalyst was removed by filtration and the solvent was removed under reduced pressure to give the desired product as a pale yellow oil (2.30 g) (Process C).

Reference Example 67

Methyl 4'-[(3-methylthio)phenoxy]dihydrocinnamate

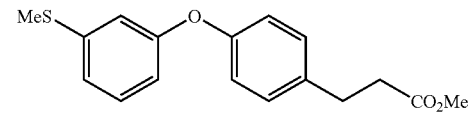

Under argon gas, the compound of Reference Example 59 (4.07 g) was dissolved in methanol (50 mL). While the solution was stirred at 10° C., magnesium (1.00 g) was added. The mixture was stirred for 3 hours while kept at this temperature, and diluted hydrochloric acid was added. The mixture was extracted with ethyl acetate and was washed sequentially with water and a saturated aqueous solution of sodium chloride. The organic phase was then dried over anhydrous sodium sulfate. The solvent was removed under reduced pressure to give the desired product as a colorless oil (3.70 g) (Process D).

Reference Examples 68 through 95

Similarly, the compounds of Reference Examples 33 through 37, 39 through 58, and 60 through 62 were used to synthesize the compounds shown in Table 3 below.

TABLE 3

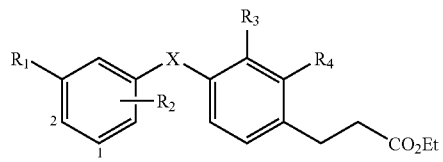

| Reference Examples | R1 | R2 | R3 | R4 | X | Process |
|---|---|---|---|---|---|---|
| 68 | Cl | 1-Cl | H | Cl | O | A |
| 69 | t-Bu | 1-H | H | H | O | B |
| 70 | $CF_3$ | 1-H | H | H | O | B |
| 71 | $CF_3$ | 1-H | OMe | H | O | B |

TABLE 3-continued

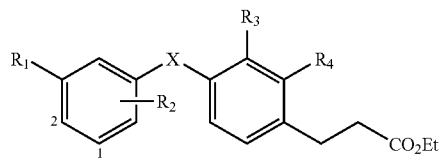

| Reference Examples | R1 | R2 | R3 | R4 | X | Process |
|---|---|---|---|---|---|---|
| 72 | $CF_3$ | 1-H | H | OMe | O | B |
| 73 | $CF_3$ | 1-H | $CF_3$ | H | O | B |
| 74 | $CF_3$ | 1-H | H | $CF_3$ | O | B |
| 75 | $CF_3$ | 1-$CF_3$ | H | H | O | B |
| 76 | $CF_3$ | 1-$CF_3$ | H | Cl | O | B |
| 77 | $CF_3$ | 2-Cl | H | H | O | A |
| 78 | $CF_3$ | 1-MeO | H | Cl | O | B |
| 79 | $Ph(CH_2)_2$ | 1-H | H | Cl | O | A |
| 80 | $Ph(CH_2)_2$ | 1-H | H | $CF_3$ | O | B |
| 81 | $Ph(CH_2)_2$ | 1-$CF_3$ | H | H | O | B |
| 82 | $Ph(CH_2)_2$ | 1-$Ph(CH_2)_2$ | H | H | O | B |
| 83 | $Ph(CH_2)_2$ | 1-$Ph(CH_2)_2$ | H | $CF_3$ | O | B |
| 84 | $Ph(CH_2)_2$ | 1-$Ph(CH_2)_2$ | H | Cl | O | A |
| 85 | i-PrO | 1-iPr | H | Cl | O | C |
| 86 | PhO | 1-H | H | Cl | O | A |
| 87 | $PhCH_2O$ | 1-H | H | H | O | A |
| 88 | $PhCH_2O$ | 1-H | H | Br | O | A |
| 89 | $PhCH_2O$ | 1-H | H | SMe | O | A |
| 90 | $PhCH_2O$ | 1-H | H | Me | O | A |
| 91 | $PhCH_2O$ | 1-H | H | Et | O | A |
| 92 | MeO | 1-$CF_3$ | H | H | O | A |
| 93 | Cl | 1-H | H | H | S | D |
| 94 | $CF_3$ | 1-$CF_3$ | H | Cl | S | A |
| 95 | MeO | 1-H | H | Cl | S | A |

Reference Example 96

Benzyl 4'-[3-benzyloxy-5-(trifluoromethyl)phenoxy] dihydrocinnamate

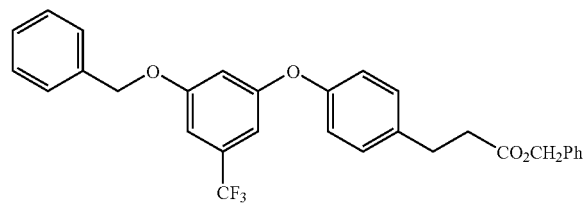

The compound of Reference Example 92 (840 mg) was dissolved in methylene chloride (20 mL). While the solution was stirred at 0° C., a 1 mol/L methylene chloride solution of tribromoboron (3.42 mL) was added dropwise. The reaction mixture was stirred at room temperature overnight. Subsequently, ice water was added, and the mixture was extracted with ethyl acetate and was washed sequentially with water and a saturated aqueous solution of sodium chloride. The organic phase was dried over anhydrous sodium sulfate. The solvent was then removed under reduced pressure to give 4'-(3-trifluoromethyl-5-hydroxyphenoxy)dihydrocinnamate as a pale brown powder (750 mg). The resulting powder was dissolved in DMF (50 mL). To this solution, potassium carbonate (1.04 g) and benzyl bromide (0.602 mL) were added and the mixture was stirred at room temperature for 8 hours. Subsequently, the reaction mixture was poured into ice water, and the mixture was extracted with ethyl acetate and was washed sequentially with water and a saturated aqueous solution of sodium chloride. The organic phase was then dried over anhydrous sodium sulfate. The solvent was removed under reduced pressure to give the desired product as a brown oil.

Reference Example 97

Benzyl 4'-(3-benzyloxyphenylthio)-2'-chlorodihydrocinnamate

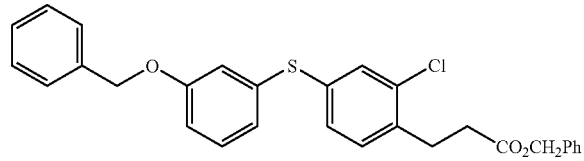

In the same manner as in Reference Example 96, the compound of Reference Example 95 was used to give the desired product as a yellow oil.

Reference Example 98

Ethyl 4'-[3-benzyloxy-5-(trifluoromethyl)phenoxy]-2'-chlorodihydrocinnamate

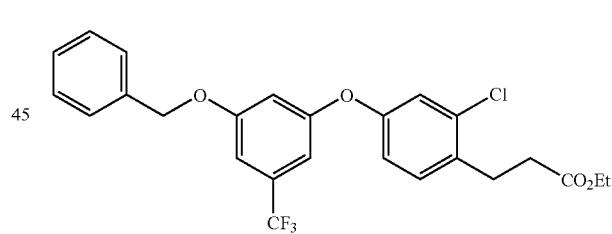

In the same manner as in Reference Example 96, the compound of Reference Example 78 was reacted to give 2'-chloro-4'-(3-trifluoromethyl-5-hydroxyphenoxy)dihydrocinnamate. This product (1.47 g) was dissolved in ethanol (10 mL). While this solution was stirred at 0° C., thionyl chloride (3 mL) was added dropwise. The mixture was stirred for 2 hours while kept at this temperature. Subsequently, the solvent was removed under reduced pressure and the residue was purified on a silica gel column chromatography (hexane:ethyl acetate=10:1 and then 6:1) to give ethyl 2'-chloro-4'-(3-trifluoromethyl-5-hydroxyphenoxy)dihydrocinnamate as a colorless oil (1.38 g). In the same manner as in Reference Example 96, the resulting ester was converted into a benzyl ether using potassium carbonate and benzyl bromide. This gave the desired product as a colorless oil.

Reference Example 99

4'-[(3-benzyloxy)phenylthio]-2'-chlorodihydrocinnamyl alcohol

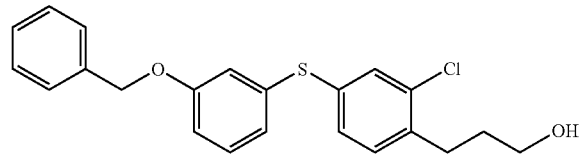

The compound of Reference Example 97 (7.409) was dissolved in THF (100 mL). While this solution was stirred at 0° C., lithium aluminum hydride (500 mg) was added. After 10 min, a 20% aqueous solution of NaOH was added and the separated insoluble inorganic residue was removed by filtration through Celite. The filtrate was extracted with ethyl acetate and the extract was washed sequentially with water and a saturated aqueous solution of sodium chloride. The organic phase was then dried over anhydrous sodium sulfate. The solvent was removed under reduced pressure to give the desired product as a colorless oil (6.37 g).

Reference Examples 100 through 130

In a similar manner to Reference Example 99, the compounds of Reference Examples 68 through 77, 79 through 91, 93 through 94, and 96 and 98 were used to synthesize the compounds shown in Table 4 below.

TABLE 4

| Reference Examples | R1 | R2 | R3 | R4 | X |
|---|---|---|---|---|---|
| 100 | Cl | 1-Cl | H | Cl | O |
| 101 | t-Bu | 1-H | H | H | O |
| 102 | CF$_3$ | 1-H | H | H | O |
| 103 | CF$_3$ | 1-H | OMe | H | O |
| 104 | CF$_3$ | 1-H | H | OMe | O |
| 105 | CF$_3$ | 1-H | CF$_3$ | H | O |
| 106 | CF$_3$ | 1-H | H | CF$_3$ | O |
| 107 | CF$_3$ | 1-CF$_3$ | H | H | O |
| 108 | CF$_3$ | 1-CF$_3$ | H | Cl | O |
| 109 | CF$_3$ | 2-Cl | H | H | O |
| 110 | CF$_3$ | PhCH$_2$O | H | Cl | O |
| 111 | Ph(CH$_2$)$_2$ | 1-H | H | Cl | O |
| 112 | Ph(CH$_2$)$_2$ | 1-H | H | CF$_3$ | O |
| 113 | Ph(CH$_2$)$_2$ | 1-CF$_3$ | H | H | O |
| 114 | CF$_3$ | 1-H | H | PhCH$_2$O | O |
| 115 | CF$_3$ | 1-H | H | Cl | S |
| 116 | Ph(CH$_2$)$_2$ | 1-Ph(CH$_2$)$_2$ | H | H | O |
| 117 | Ph(CH$_2$)$_2$ | 1-Ph(CH$_2$)$_2$ | H | CF$_3$ | O |
| 118 | Ph(CH$_2$)$_2$ | 1-Ph(CH$_2$)$_2$ | H | Cl | O |
| 119 | i-PrO | 1-iPr | H | Cl | O |
| 120 | PhO | 1-H | H | Cl | O |
| 121 | PhCH$_2$O | 1-H | H | H | O |
| 122 | PhCH$_2$O | 1-H | H | Br | O |
| 123 | PhCH$_2$O | 1-H | H | SMe | O |
| 124 | PhCH$_2$O | 1-H | H | Me | O |
| 125 | PhCH$_2$O | 1-H | H | Et | O |
| 126 | PhCH$_2$O | 1-CF$_3$ | H | H | O |
| 127 | Cl | 1-H | H | H | S |
| 128 | CF$_3$ | 1-CF$_3$ | H | Cl | S |
| 129 | Et | 1-H | H | H | O |
| 130 | MeS | 1-H | H | H | O |

Reference Example 131

4'-(3-benzyloxyphenylthio)-2'-chloro-dihydrocinnamyl iodide

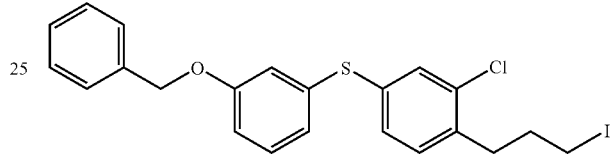

The compound of Reference Example 99 (1.38 g) was dissolved in THF (20 mL). While this solution was stirred at 0° C., imidazole (545 mg), triphenylphosphine (2.10 g), and iodine (2.00 g) were added. The mixture was stirred for 2 hours at this temperature and for the subsequent 1.5 hours at room temperature, and additional imidazole (160 mg), triphenyl phosphine (600 mg), and iodine (500 mg) were added. The mixture was stirred overnight, followed by the addition of water and then sodium thiosulfate. The reaction mixture was then extracted with ethyl acetate and the extract was washed sequentially with water and a saturated aqueous solution of sodium chloride. The organic phase was then dried over anhydrous sodium sulfate. The solvent was removed under reduced pressure and the residue was purified on a silica gel column chromatography (hexane:ethyl acetate=50:1) to give the desired product as a colorless oil (1.55 g).

Reference Examples 132 through 162

In a similar manner to Reference Example 131, the compounds of Reference Examples 100 through 130 were used to synthesize the compounds shown in Table 5 below.

TABLE 5

| Reference Examples | R1 | R2 | R3 | R4 | X |
|---|---|---|---|---|---|
| 132 | Cl | 1-Cl | H | Cl | O |
| 133 | t-Bu | 1-H | H | H | O |
| 134 | CF$_3$ | 1-H | H | H | O |
| 135 | CF$_3$ | 1-H | OMe | H | O |

TABLE 5-continued

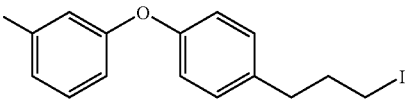

| Reference Examples | R1 | R2 | R3 | R4 | X |
|---|---|---|---|---|---|
| 136 | CF$_3$ | 1-H | H | OMe | O |
| 137 | CF$_3$ | 1-H | CF$_3$ | H | O |
| 138 | CF$_3$ | 1-H | H | CF$_3$ | O |
| 139 | CF$_3$ | 1-CF$_3$ | H | H | O |
| 140 | CF$_3$ | 1-CF$_3$ | H | Cl | O |
| 141 | CF$_3$ | 2-Cl | H | H | O |
| 142 | CF$_3$ | PhCH$_2$O | H | Cl | O |
| 143 | Ph(CH$_2$)$_2$ | 1-H | H | Cl | O |
| 144 | Ph(CH$_2$)$_2$ | 1-H | H | CF$_3$ | O |
| 145 | Ph(CH$_2$)$_2$ | 1-CF$_3$ | H | H | O |
| 146 | CF$_3$ | 1-H | H | PhCH$_2$O | O |
| 147 | CF$_3$ | 1-H | H | Cl | S |
| 148 | Ph(CH$_2$)$_2$ | 1-Ph(CH$_2$)$_2$ | H | H | O |
| 149 | Ph(CH$_2$)$_2$ | 1-Ph(CH$_2$)$_2$ | H | CF$_3$ | O |
| 150 | Ph(CH$_2$)$_2$ | 1-Ph(CH$_2$)$_2$ | H | Cl | O |
| 151 | i-PrO | 1-iPr | H | Cl | O |
| 152 | PhO | 1-H | H | Cl | O |
| 153 | PhCH$_2$O | 1-H | H | H | O |
| 154 | PhCH$_2$O | 1-H | H | Br | O |
| 155 | PhCH$_2$O | 1-H | H | SMe | O |
| 156 | PhCH$_2$O | 1-H | H | Me | O |
| 157 | PhCH$_2$O | 1-H | H | Et | O |
| 158 | PhCH$_2$O | 1-CF$_3$ | H | H | O |
| 159 | Cl | 1-H | H | H | S |
| 160 | CF$_3$ | 1-CF$_3$ | H | Cl | S |
| 161 | Et | 1-H | H | H | O |
| 162 | MeS | 1-H | H | H | O |

Reference Example 163

4-(3,5-dichlorophenoxy)benzylbromide

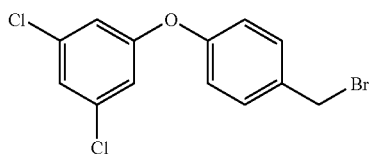

Using 3,5-dichlorophenol and 4-fluorobenzaldehyde, the reaction was carried out in the same manner as in Reference Example 1 to obtain 4-(3,5-dichlorophenoxy)benzaldehyde. Subsequently, the same procedure as in Reference Example 99 was followed using sodium borohydride in place of the lithium aluminum hydride. This gave 4-(3,5-dichlorophenoxy)benzyl alcohol. The resulting alcohol (2.03 g), along with carbon tetrabromide (2.75 g), was dissolved in methylene chloride (30 mL). While this solution was stirred at 0° C., triphenyl phosphine (2.17 g) was added. The mixture was stirred at 0° C. for 1 hour and at room temperature for the subsequent 30 min. The solvent was removed under reduced pressure and the residue was purified on a silica gel column chromatography (hexane:ethyl acetate=20:1) to give the desired product as a colorless oil (3.12 g).

Reference Example 164

4'-benzyloxy-dihydrocinnamyl iodide

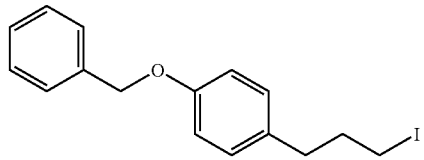

Using 4'-benzyloxydihydrocinnamyl alcohol, the reaction was carried out in the same manner as in Reference Example 131 to obtain the desired product as a yellow powder.

Reference Example 165

1-iodopropyl-4-[(3-methanesulfinyl)phenoxy]benzene

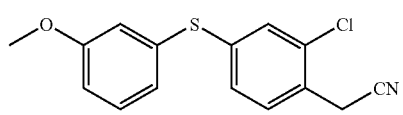

The compound of Reference Example 162 (1.80 g) was dissolved in methylene chloride (30 mL). While this solution was stirred at 0° C., m-chloroperbenzoic acid (770 mg) was added in small portions. The mixture was stirred at this temperature for 1 hour and at room temperature for the subsequent 24 hours. Following addition of water, the mixture was extracted with ethyl acetate and the extract was washed sequentially with a saturated aqueous solution of sodium carbonate and a saturated aqueous solution of sodium chloride. The organic phase was then dried over anhydrous sodium sulfate. The solvent was removed under reduced pressure and the residue was purified on a silica gel column chromatography (hexane:ethyl acetate=2:1 and then 1:2) to give the desired product as a yellow oil (1.29 g).

Reference Example 166

4'-(3-benzyloxyphenylthio)-2'-chlorophenethyl iodide

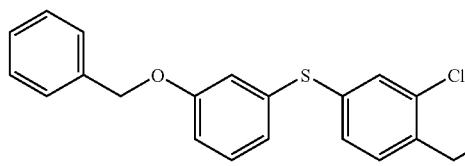

Reference Example 166-1

2'-chloro-4'-(3-methoxyphenylthio)benzylcyanide

The compound of Reference Example 31 was treated in the same manner as in Reference Example 99 to obtain an alcohol. The alcohol (5.64 g) was dissolved in methylene chloride (100 mL) and phosphorus tribromide (2.25 mL) was added dropwise. Following stirring at room temperature for 1 hour, ice water was added and the mixture was extracted with ethyl acetate. The extract was washed sequentially with water and an aqueous solution of sodium chloride, and the organic phase was dried over anhydrous sodium sulfate. The solvent was removed to obtain a pale yellow oil. The oil and potassium cyanide (1.56 g) were dissolved in a mixture of DMSO (25 mL) and water (10 mL) and the solution was stirred at 90° C. for 5 hours. Following addition of water, the mixture was extracted with ethyl acetate and the extract was washed sequentially with water and a saturated aqueous solution of sodium chloride. The organic phase was dried over anhydrous sodium sulfate. The solvent was removed and the residue was purified on a silica gel column chromatography (hexane:ethyl acetate=10:1) to give the desired cyano-product as a pale yellow oil (3.81 g).

Reference Example 166-2

2'-chloro-4'-(3-methoxyphenylthio)phenylethyl acetate

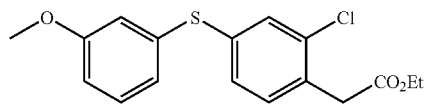

The cyano-product (3.81 g) and potassium hydroxide (3.68 g) were added to a mixture of ethanol (80 mL), and water (10 mL), and the solution was refluxed for 6 hours. Subsequently, the solution was allowed to cool and the insoluble material was removed by filtration. The filtrate was neutralized with diluted hydrochloric acid. This mixture was extracted with ethyl acetate and the extract was washed sequentially with water and a saturated aqueous solution of sodium chloride. The organic phase was then dried over anhydrous sodium sulfate. The solvent was removed and ethanol (50 mL) and thionyl chloride (2 mL) were added to the resulting residue. This mixture was stirred at room temperature for 1 hour and the solvent was removed. The resulting residue was purified on a silica gel column chromatography (hexane:ethyl acetate=10:1) to give the ethyl ester product as a colorless oil (3.89 g).

Reference Example 166-3

4'-(3-benzyloxyphenylthio)-2'-chlorophenethyl iodide

The ethyl ester was reacted in the same manner as in Reference Example 98 to obtain 4'-(3-benzyloxyphenylthio)-2'-chlorophenylethyl acetate. The product was reduced as in Reference Example 99 to obtain an alcohol, which in turn was reacted in the same manner as in Reference Example 131 to give the desired product as a colorless oil.

Reference Example 167

1-(3-benzyloxyphenylthio)-3-chloro-4-iodobutylbenzene

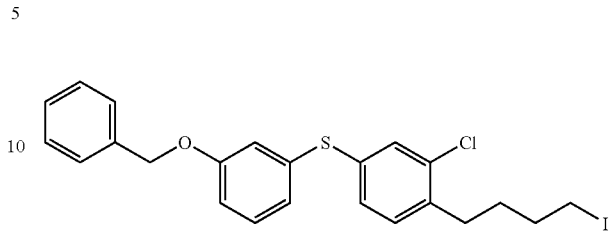

Reference Example 167-1

4-(3-benzyloxyphenylthio)-2-chlorophenethyl aldehyde

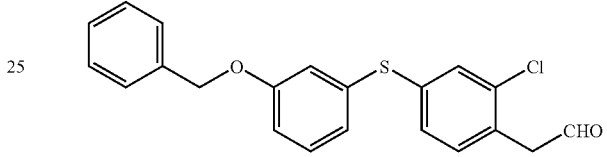

4'-(3-benzyloxyphenylthio)-2'-chlorophenylethyl acetate obtained in Reference Example 166-3 was subjected to alkali-hydrolysis. The resulting product was condensed with N,O-dimethylhydroxylamine to form an amide product, which in turn was reduced in the same manner as in Reference Example 99 to give the desired aldehyde product as a yellow oil.

Reference Example 167-2

4-[(3-benzyloxyphenylthio)-2-chlorophenyl]ethyl butyrate

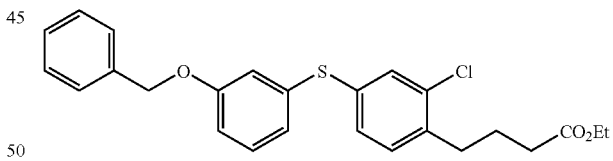

The compound of Reference Example 167-1 was reacted in the same manner as in Reference Example 32 and the unsaturated bonds of the resulting product were reduced in the same manner as in Reference Example 64 to give the desired ethyl butyrate derivative.

Reference Example 167-3

1-(3-benzyloxyphenylthio)-3-chloro-4-iodobutylbenzene

The compound of Reference Example 167-2 was reacted in the same manner as in Reference Example 99 to obtain an alcohol product, which in turn was reacted in the same manner as in Reference Example 131 to give the desired product as a colorless oil.

Example 1

Ethyl 2-t-butoxycarbonylamino-5-[2-chloro-4-(3-trifluoromethylphenylthio)]phenyl-2-ethoxycarbonylpentanoate

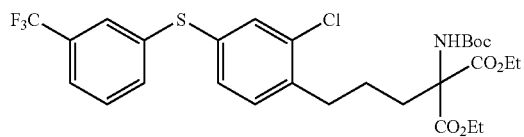

At room temperature and under argon gas, sodium t-butoxide (490 mg) was added to diethyl 2-t-butoxycarbonylaminomalonate (1.3 mL) in a mixture of THF (35 mL) and DMF (4 mL). This mixture was stirred at 80° C. for 20 min and was allowed to cool to room temperature. To the cooled mixture, a THF solution (5 mL) of the compound of Reference Example 147 (1.55 g) was added dropwise. The resulting mixture was refluxed for 5 hours, was poured into ice water, and was extracted with ethyl acetate. The extract was washed sequentially with water and a saturated aqueous solution of sodium chloride. The organic phase was then dried over anhydrous sodium sulfate. The solvent was removed under reduced pressure and the residue was purified on a silica gel column chromatography (hexane:ethyl acetate=5:1) to give the desired product as a colorless oil (1.87 g).

$^1$H-NMR (400 MHz, CDCl$_3$) δ 1.22-1.36 (6H, m), 1.42 (9H, s), 1.45-1.53 (2H, m), 2.37 (2H, br), 2.74 (2H, t, J=7.8 Hz), 4.23 (4H, m), 5.94 (1H, s), 7.16-7.21 (2H, m), 7.36-7.56 (5H, m)

Examples 2 through 36

In a similar manner to Example 1, the compounds of Reference Examples 131 through 146, 148 through 161, and 163, 165, 166 and 167 were used to synthesize the compounds shown in Table 6 below.

TABLE 6

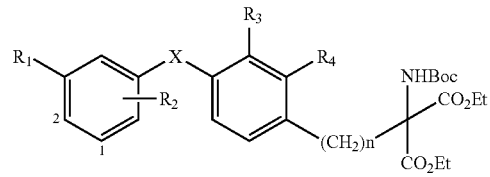

| Examples | R1 | R2 | R3 | R4 | X | n | Characteristics | Yield (%) |
|---|---|---|---|---|---|---|---|---|
| 2 | Cl | 1-Cl | H | Cl | O | 3 | Colorless oil | 74 |
| 3 | t-Bu | 1-H | H | H | O | 3 | Colorless oil | 64 |
| 4 | CF$_3$ | 1-H | H | H | O | 3 | Colorless oil | 100 |
| 5 | CF$_3$ | 1-H | OMe | H | O | 3 | Colorless oil | 100 |
| 6 | CF$_3$ | 1-H | H | OMe | O | 3 | Colorless oil | 100 |
| 7 | CF$_3$ | 1-H | CF$_3$ | H | O | 3 | Colorless oil | 100 |
| 8 | CF$_3$ | 1-H | H | CF$_3$ | O | 3 | Colorless oil | 92 |
| 9 | CF$_3$ | 1-CF$_3$ | H | H | O | 3 | Colorless oil | 47 |
| 10 | CF$_3$ | 1-CF$_3$ | H | Cl | O | 3 | Colorless oil | 89 |
| 11 | CF$_3$ | 1-Cl | H | H | O | 3 | Colorless oil | 94 |
| 12 | CF$_3$ | PhCH$_2$O | H | Cl | O | 3 | Colorless oil | 91 |
| 13 | Ph(CH$_2$)$_2$ | 1-H | H | Cl | O | 3 | Colorless oil | 83 |
| 14 | Ph(CH$_2$)$_2$ | 1-H | H | CF$_3$ | O | 3 | Colorless oil | 90 |
| 15 | Ph(CH$_2$)$_2$ | 1-CF$_3$ | H | H | O | 3 | Colorless oil | 97 |
| 16 | Ph(CH$_2$)$_2$ | 1-Ph(CH$_2$)$_2$ | H | H | O | 3 | Colorless oil | 95 |
| 17 | Ph(CH$_2$)$_2$ | 1-Ph(CH$_2$)$_2$ | H | CF$_3$ | O | 3 | Colorless oil | 100 |
| 18 | Ph(CH$_2$)$_2$ | 1-Ph(CH$_2$)$_2$ | H | Cl | O | 3 | Colorless oil | 98 |
| 19 | i-PrO | 1-iPr | H | Cl | O | 3 | Colorless oil | 100 |
| 20 | PhO | 1-H | H | Cl | O | 3 | Colorless oil | 92 |
| 21 | PhCH$_2$O | 1-H | H | H | O | 3 | Colorless oil | 95 |
| 22 | PhCH$_2$O | 1-H | H | Br | O | 3 | Colorless oil | 100 |
| 23 | PhCH$_2$O | 1-H | H | SMe | O | 3 | Colorless oil | — |
| 24 | PhCH$_2$O | 1-H | H | Me | O | 3 | Colorless oil | 100 |
| 25 | PhCH$_2$O | 1-H | H | Et | O | 3 | Colorless oil | 72 |
| 26 | PhCH$_2$O | 1-H | H | Cl | S | 2 | Pale yellow oil | 100 |
| 27 | PhCH$_2$O | 1-H | H | Cl | S | 3 | Colorless oil | 100 |
| 28 | PhCH$_2$O | 1-H | H | Cl | S | 4 | Colorless oil | 100 |
| 29 | PhCH$_2$O | 1-CF$_3$ | H | H | O | 3 | Colorless oil | 99 |
| 30 | Cl | 1-H | H | H | S | 3 | Colorless oil | 82 |
| 31 | CF$_3$ | 1-CF$_3$ | H | Cl | S | 3 | Colorless oil | 66 |
| 32 | Et | 1-H | H | H | O | 3 | Colorless oil | 100 |
| 33 | SOMe | 1-H | H | H | O | 3 | Colorless oil | 100 |
| 34 | Cl | 1-Cl | H | H | O | 1 | Colorless oil | 56 |
| 35 | CF$_3$ | 1-H | H | PhCH$_2$O | O | 3 | Colorless oil | 100 |
| 36 | PhCH$_2$O | 1-H | H | Cl | O | 3 | Colorless oil | 100 |

—Yield is shown in Table 7 in association with the subsequent step.

Example 37

Ethyl 5-[(4-benzyloxy)phenyl]-2-t-butoxycarbonylamino-2-ethoxycarbonylpentanoate

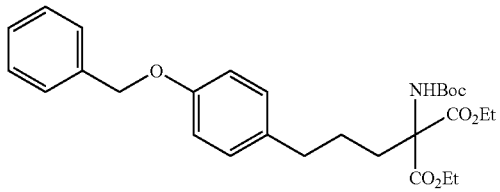

The compound of Reference Example 164 was reacted in the same manner as in Example 1 to give the desired product as a pale yellow oil.

$^1$H-NMR (400 MHz, CDCl$_3$) δ 1.22 (6H, t, J=7.1 Hz), 1.42 (9H, s), 1.44-1.47 (2H, m), 2.31 (2H, br s), 2.57 (2H, t, J=7.6 Hz), 4.11-4.27 (4H, m), 5.03 (2H, s), 5.92 (1H, br s), 6.88 (2H, d, J=8.8 Hz) 7.06 (2H, d, J=8.8 Hz), 7.29-7.43 (5H, m)

Example 38

Ethyl 2-t-butoxycarbonylamino-5-[4-(3,5-dichlorophenoxy)phenyl]-2-ethoxycarbonylpentanoate

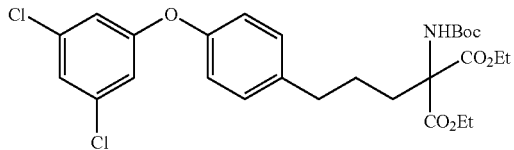

The compound of Example 37 was reduced in the same manner as in Reference Example 65. The resulting phenol product (1.27 g), along with 3,5-dichlorophenylboric acid (1.18 g), was dissolved in methylene chloride (30 mL). While this solution was being stirred, copper acetate (676 mg) and triethylamine (0.86 mL) were added. After 16 hours and a further 8 hours later, the same amount of additional copper acetate was added and the mixture was stirred for the subsequent 40 hours. Subsequently, the insoluble material was removed by filtration. The filtrate was poured into water and the mixture was extracted with ethyl acetate. The extract was washed sequentially with water and a saturated aqueous solution of sodium chloride. The organic phase was then dried over anhydrous magnesium sulfate. The solvent was removed under reduced pressure and the residue was purified on a silica gel column chromatography (hexane:ethyl acetate=20:1) to give the desired product as a pale blue oil (333 mg).

Example 39

2-t-butoxycarbonylamino-5-[2-chloro-4-(3-trifluoromethylphenylthio)phenyl]pentane-1-ol

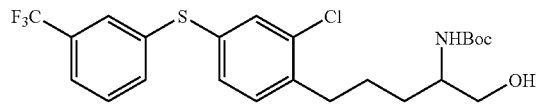

The compound of Example 1 (1.87 g) was dissolved in THF (30 mL). While this solution was stirred at 0° C., lithium borohydride (675 mg) was added. Subsequently, ethanol (5 mL) was added and the mixture was allowed to gradually warm to room temperature. After stirring overnight, ice water was added to the reaction mixture and the organic solvent was removed under reduced pressure. To the resulting residue, a 10% aqueous citric acid was added to adjust the pH to 3. The resulting mixture was extracted with ethyl acetate. The extract was washed sequentially with water and a saturated aqueous solution of sodium chloride. The organic phase was then dried over anhydrous sodium sulfate. The solvent was removed under reduced pressure and the residue was purified on a silica gel column chromatography (hexane:ethyl acetate=1:1) to give the desired product (0.27 g) as a colorless oil.

FABMS: 490 ([M+H]$^+$)

$^1$H-NMR (400 MHz, CDCl$_3$) δ 1.44 (9H, s), 1.63-1.73 (4H, m), 2.72-2.78 (2H, m), 3.57 (1H, br), 3.68-3.70 (2H, m), 4.61 (1H, br s), 7.20-7.22 (2H, m), 7.39-7.55 (5H, m)

Examples 40 through 74

In a similar manner to Example 39, the compounds of Examples 2 through 36 and 38 were used to synthesize the compounds shown in Table 7 below.

TABLE 7

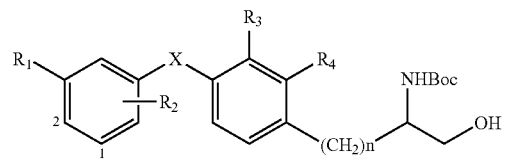

| Examples | R1 | R2 | R3 | R4 | X | n | Characteristics | Yield (%) |
|---|---|---|---|---|---|---|---|---|
| 40 | Cl | 1-Cl | H | Cl | O | 3 | Colorless oil | 12 |
| 41 | t-Bu | 1-H | H | H | O | 3 | Colorless oil | 15 |
| 42 | CF$_3$ | 1-H | H | H | O | 3 | Colorless oil | 17 |
| 43 | CF$_3$ | 1-H | OMe | H | O | 3 | Colorless oil | 5 |
| 44 | CF$_3$ | 1-H | H | OMe | O | 3 | Colorless oil | 17 |
| 45 | CF$_3$ | 1-H | CF$_3$ | H | O | 3 | Colorless oil | 16 |
| 46 | CF$_3$ | 1-H | H | CF$_3$ | O | 3 | Colorless oil | 22 |
| 47 | CF$_3$ | 1-CF$_3$ | H | H | O | 3 | Colorless oil | 14 |
| 48 | CF$_3$ | 1-CF$_3$ | H | Cl | O | 3 | Colorless oil | 19 |
| 49 | CF$_3$ | 1-Cl | H | H | O | 3 | Colorless powder | 29 |
| 50 | CF$_3$ | PhCH$_2$O | H | Cl | O | 3 | Colorless oil | 12 |

TABLE 7-continued

| Examples | R1 | R2 | R3 | R4 | X | n | Characteristics | Yield (%) |
|---|---|---|---|---|---|---|---|---|
| 51 | Ph(CH$_2$)$_2$ | 1-H | H | Cl | O | 3 | Colorless oil | 15 |
| 52 | Ph(CH$_2$)$_2$ | 1-H | H | CF$_3$ | O | 3 | Colorless oil | 18 |
| 53 | Ph(CH$_2$)$_2$ | 1-CF$_3$ | H | H | O | 3 | Colorless oil | 16 |
| 54 | Ph(CH$_2$)$_2$ | 1-Ph(CH$_2$)$_2$ | H | H | O | 3 | Colorless oil | 11 |
| 55 | Ph(CH$_2$)$_2$ | 1-Ph(CH$_2$)$_2$ | H | CF$_3$ | O | 3 | Colorless oil | 13 |
| 56 | Ph(CH$_2$)$_2$ | 1-Ph(CH$_2$)$_2$ | H | Cl | O | 3 | Colorless oil | 10 |
| 57 | i-PrO | 1-iPr | H | Cl | O | 3 | Colorless oil | 7 |
| 58 | PhO | 1-H | H | Cl | O | 3 | Colorless oil | 17 |
| 59 | PhCH$_2$O | 1-H | H | H | O | 3 | Colorless oil | 11 |
| 60 | PhCH$_2$O | 1-H | H | Br | O | 3 | Colorless oil | 11 |
| 61 | PhCH$_2$O | 1-H | H | SMe | O | 3 | Colorless oil | 10 |
| 62 | PhCH$_2$O | 1-H | H | Me | O | 3 | Colorless oil | 11 |
| 63 | PhCH$_2$O | 1-H | H | Et | O | 3 | Colorless oil | 8 |
| 64 | PhCH$_2$O | 1-H | H | Cl | S | 2 | Pale yellow oil | 11 |
| 65 | PhCH$_2$O | 1-H | H | Cl | S | 3 | Colorless oil | 26 |
| 66 | PhCH$_2$O | 1-H | H | Cl | S | 4 | Colorless oil | 15 |
| 67 | PhCH$_2$O | 1-CF$_3$ | H | H | O | 3 | Colorless oil | 10 |
| 68 | Cl | 1-H | H | H | S | 3 | Colorless oil | 31 |
| 69 | CF$_3$ | 1-CF$_3$ | H | Cl | S | 3 | Colorless oil | 13 |
| 70 | Et | 1-H | H | H | O | 3 | Colorless oil | 13 |
| 71 | SOMe | 1-H | H | H | O | 3 | Colorless oil | 27 |
| 72 | Cl | 1-Cl | H | H | O | 1 | Colorless powder | 24 |
| 73 | CF$_3$ | 1-H | H | PhCH$_2$O | O | 3 | Colorless oil | 5 |
| 74 | Cl | 1-Cl | H | H | O | 3 | Colorless oil | 13 |
| 75 | PhCH$_2$O | 1-H | H | Cl | O | 3 | Colorless oil | 19 |

Example 76

2-amino-5-[2-chloro-4-(3-trifluoromethylphenylthio)phenyl]pentane-1-ol hydrochloride

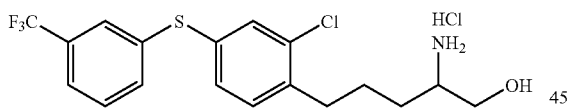

To a methanol solution (5 mL) of the compound of Example 39 (0.27 g), ethyl acetate containing 3 mol/L hydrochloric acid (5 mL) was added and the mixture was stirred in an ice bath. The mixture was allowed to warm to room temperature and was left overnight. Subsequently, the solvent was removed under reduced pressure to give the desired product as a colorless powder (0.22 g).

FABMS: 390 ([M+H]$^+$)

$^1$H-NMR (400 MHz, DMSO-d$_6$) δ 1.52-1.61 (4H, br s), 2.70 (2H, t, J=7.3 Hz), 3.09 (1H, br), 3.38-3.43 (1H, m), 3.55-3.58 (1H, m), 5.28 (1H, t, J=4.9 Hz), 7.34 (1H, dd, J=7.9 Hz, 2.0 Hz), 7.41 (1H, d, J=7.3 Hz), 7.54 (1H, d, J=2.0 Hz), 7.56-7.63 (3H, m), 7.68 (1H, d, J=7.3 Hz), 7.80 (3H, br)

MP=166-168° C.

Example 77-111

In a similar manner to Example 36, the compounds shown in Table 7 were used to synthesize the compounds shown in Table 8 below.

TABLE 8

| Examples | R1 | R2 | R3 | R4 | X | n | Characteristics | Yield (%) | FABMS [M + H]$^+$ | Melting point (° C.) |
|---|---|---|---|---|---|---|---|---|---|---|
| 77 | Cl | 1-Cl | H | Cl | O | 3 | Colorless powder | 87 | 374 | 154-156 |
| 78 | t-Bu | 1-H | H | H | O | 3 | Colorless powder | 98 | 328 | 133-137 |
| 79 | CF$_3$ | 1-H | H | H | O | 3 | Colorless powder | 100 | 340 | 143-145 |

TABLE 8-continued

| Examples | R1 | R2 | R3 | R4 | X | n | Characteristics | Yield (%) | FABMS [M + H]+ | Melting point (° C.) |
|---|---|---|---|---|---|---|---|---|---|---|
| 80 | CF3 | 1-H | OMe | H | O | 3 | Colorless amorphous | 100 | 370 | |
| 81 | CF3 | 1-H | H | OMe | O | 3 | Colorless oil | 88 | 370 | |
| 82 | CF3 | 1-H | CF3 | H | O | 3 | Colorless powder | 91 | 408 | 128-130 |
| 83 | CF3 | 1-H | H | CF3 | O | 3 | Colorless amorphous | 95 | 408 | |
| 84 | CF3 | 1-CF3 | H | H | O | 3 | Colorless powder | 88 | 408 | 122-125 |
| 85 | CF3 | 1-CF3 | H | Cl | O | 3 | Colorless powder | 68 | 442 | 126-128 |
| 86 | CF3 | 1-Cl | H | H | O | 3 | Pale Yellow amorphous | 87 | 374 | |
| 87 | CF3 | PhCH2O | H | Cl | O | 3 | Colorless amorphous | 92 | 480 | |
| 88 | Ph(CH2)2 | 1-H | H | Cl | O | 3 | Pale Yellow amorphous | 87 | 410 | |
| 89 | Ph(CH2)2 | 1-H | H | CF3 | O | 3 | Colorless amorphous | 91 | 444 | |
| 90 | Ph(CH2)2 | 1-CF3 | H | H | O | 3 | Colorless amorphous | 94 | 444 | |
| 91 | Ph(CH2)2 | 1-Ph(CH2)2 | H | H | O | 3 | Colorless oil | 98 | 480 | |
| 92 | Ph(CH2)2 | 1-Ph(CH2)2 | H | CF3 | O | 3 | Colorless oil | 100 | 548 | |
| 93 | Ph(CH2)2 | 1-Ph(CH2)2 | H | Cl | O | 3 | Yellow oil | 95 | 514 | |
| 94 | i-PrO | 1-iPr | H | Cl | O | 3 | Colorless amorphous | 82 | 406 | |
| 95 | PhO | 1-H | H | Cl | O | 3 | Brown amorphous | 89 | 398 | |
| 96 | PhCH2O | 1-H | H | H | O | 3 | Colorless amorphous | 100 | 378 | |
| 97 | PhCH2O | 1-H | H | Br | O | 3 | Colorless amorphous | 92 | 458 | |
| 98 | PhCH2O | 1-H | H | SMe | O | 3 | Yellow oil | 96 | 424 | |
| 99 | PhCH2O | 1-H | H | Me | O | 3 | Yellow amorphous | 89 | 392 | |
| 100 | PhCH2O | 1-H | H | Et | O | 3 | Yellow amorphous | 64 | 406 | |
| 101 | PhCH2O | 1-H | H | Cl | S | 2 | Colorless amorphous | 93 | 414 | |
| 102 | PhCH2O | 1-H | H | Cl | S | 3 | Colorless powder | 100 | 428 | 145-147 |
| 103 | PhCH2O | 1-H | H | Cl | S | 4 | Colorless amorphous | 93 | 442 | |
| 104 | PhCH2O | 1-CF3 | H | H | O | 3 | Colorless amorphous | 93 | 446 | |
| 105 | Cl | 1-H | H | H | S | 3 | Colorless powder | 71 | 322 | 122-124 |
| 106 | CF3 | 1-CF3 | H | Cl | S | 3 | Colorless powder | 92 | 458 | 134-137 |
| 107 | Et | 1-H | H | H | O | 3 | Colorless powder | 91 | 300 | 117-118 |
| 108 | SOMe | 1-H | H | H | O | 3 | Colorless powder | 100 | 334 | 110-112 |
| 109 | Cl | 1-Cl | H | H | O | 1 | Colorless powder | 96 | 312 | 157-160 |
| 110 | CF3 | 1-H | H | PhCH2O | O | 3 | Colorless oil | 100 | 446 | |
| 111 | Cl | 1-Cl | H | H | O | 3 | Colorless powder | 92 | 340 | 136-140 |

Example 112

5-[4-(3-benzyloxyphenoxy)-2-chlorophenyl]-2-t-butoxycarbonylamino-2-methoxymethylpentane-1-ol

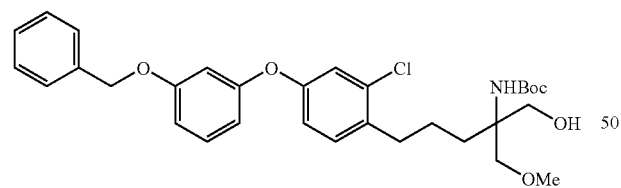

2-[4-(3-benzyloxyphenoxy)-2-chlorophenyl]propyl-2-t-butoxycarbonylamino-1,3-propanediol (720 mg) was dissolved in acetonitrile (20 mL). Ag2O (1.85 g) and MeI (3 mL) were added and the mixture was stirred at room temperature for 7 days. Subsequently, the mixture was filtered through Celite and the filtrate was concentrated and purified on a silica gel column chromatography (hexane:ethyl acetate=3:1). The dimethyl ether product (Example 112, 360 mg) and the monomethyl ether product (Example 113, 310 mg), each a colorless oil, were obtained from the first eluate fraction and the second eluate fraction, respectively.

FABMS: 556 ([M+H]+)

1H-NMR (400 MHz, CDCl3) δ 1.43 (9H, s), 1.48-1.81 (4H, m), 2.68 (2H, t, J=7.8 Hz), 3.33 (1H, d, J=8.8 Hz), 3.36 (3H, s), 3.57 (1H, d, 8.8 Hz), 3.65 (2H, d, J=6.8 Hz), 5.03 (2H, s), 5.10 (1H, br s), 6.59-6.62 (2H, m), 6.74 (1H, dd, J=8.3 Hz, 2.4 Hz), 6.84 (1H, dd, J=8.3 Hz, 2.4 Hz), 7.00 (1H, d, J=2.4 Hz), 7.15 (1H, d, J=8.3 Hz), 7.23 (1H, t, J=8.3 Hz), 7.33-7.42 (5H, m)

Example 113

2-[4-(3-benzyloxyphenoxy)-2-chlorophenyl]propyl-2-t-butoxycarbonylamino-1,3-propanedioldimethyl ether

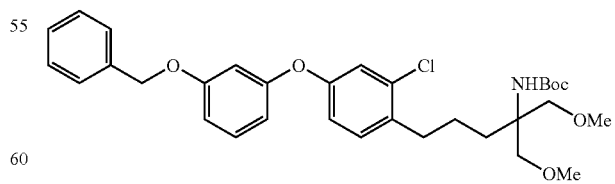

A colorless oil (See Example 112).
FABMS: 570 ([M+H]+)
1H-NMR (400 MHz, CDCl3) δ 1.42 (9H, s), 1.48-1.61 (3H, m), 1.84 (1H, br), 2.67 (2H, t, J=7.8 Hz), 3.34 (6H, s), 3.46 (2H, d, J=8.8 Hz), 3.50 (2H, d, J=8.8 Hz), 4.82 (1H, br s), 5.03

(2H, s), 6.59-6.63 (2H, m), 6.73 (1H, dd, J=8.3 Hz, 2.4 Hz), 6.83 (1H, dd, J=8.3 Hz, 2.4 Hz), 6.99 (1H, d, J=2.4 Hz), 7.15 (1H, d, J=8.3 Hz), 7.23 (1H, t, J=8.3 Hz), 7.32-7.42 (5H, m)

Example 114

2-t-butoxycarbonylamino-2-methoxymethyl-5-[4-(3-trifluoromethylphenoxy)phenyl]pentane-1-ol

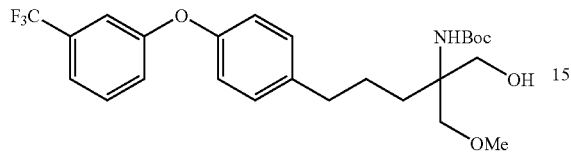

2-t-butoxycarbonylamino-2-[4-(3-trifluoromethylphenoxy)phenyl]propyl-1,3-propanediol was reacted in the same manner as in Example 112 to give the desired products (Example 114 and Example 115), each as a colorless oil.

FABMS: 484 ([M+H]$^+$)

$^1$H-NMR (400 MHz, CDCl$_3$) δ 1.42 (9H, s), 1.48-1.83 (4H, m), 2.57-2.65 (2H, m), 3.33 (1H, d, J=8.8 Hz), 3.37 (3H, s), 3.58 (1H, d, 8.8 Hz), 3.62 (2H, br s), 5.07 (1H, br s), 6.94 (2H, d, J=6.4 Hz), 7.10-7.21 (4H, m), 7.30 (1H, d, J=7.8 Hz), 7.40 (1H, t, J=7.8 Hz)

Example 115

2-t-butoxycarbonylamino-2-[4-(3-trifluoromethylphenoxy)phenyl]propyl-1,3-propanedioldimethyl ether

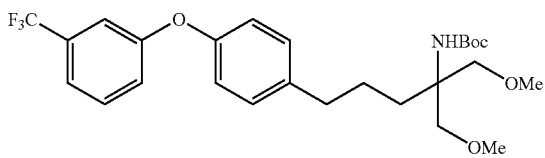

A colorless oil (See Example 114).

FABMS: 498 ([M+H]$^+$)

$^1$H-NMR (400 MHz, CDCl$_3$) δ 1.42 (9H, s), 1.48-1.66 (3H, m), 1.81-1.85 (1H, m), 2.60 (2H, t, J=7.8 Hz), 3.34 (6H, s), 3.46 (2H, d, J=8.8 Hz), 3.49 (2H, d, 8.8 Hz), 4.83 (1H, br s), 6.93 (2H, dd, J=6.4 Hz, 2.0 Hz), 7.12-7.22 (4H, m), 7.31 (1H, d, J=7.8 Hz), 7.41 (1H, d, J=7.8 Hz)

Example 116-119

Using 2-[4-(3-benzyloxyphenylthio)-2-chlorophenyl]propyl-2-t-butoxycarbonylamino-1,3-propanediol and 2-[4-(3-benzyloxyphenylthio)-2-chlorophenyl]ethyl-2-t-butoxycarbonylamino-1,3-propanediol, reactions were carried out in the same manner as in Example 112 to obtain the compounds shown in Table 9 below.

TABLE 9

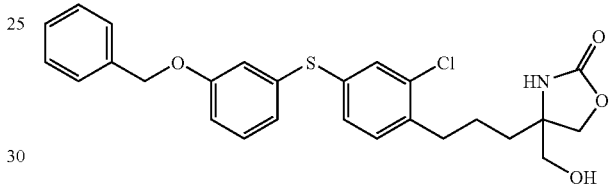

| Examples | R | n | Characteristics | FABMS [M + H]$^+$ |
|---|---|---|---|---|
| 116 | H | 2 | Colorless oil | 558 |
| 117 | Me | 2 | Colorless oil | 572 |
| 118 | H | 3 | Colorless oil | 572 |
| 119 | Me | 3 | Colorless oil | 586 |

Example 120

4-[4-(3-benzyloxyphenylthio)-2-chlorophenyl]propyl-4-hydroxymethyl-2-oxazolidinone

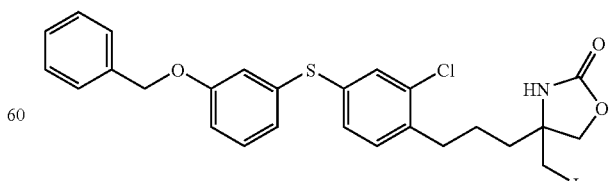

2-[4-(3-benzyloxyphenylthio)-2-chlorophenyl]propyl-2-t-butoxycarbonylamino-1,3-propanediol (3.30 g) was dissolved in THF (80 mL). At 0° C., 60% sodium hydride (600 mg) was added and the mixture was stirred at room temperature for 24 hours. To the resulting reaction mixture, ice water was added and the mixture was extracted with ethyl acetate. The extract was washed sequentially with water and a saturated aqueous solution of sodium hydroxide, and the organic phase was dried over anhydrous sodium sulfate. The solvent was removed and the residue was purified on a silica gel column chromatography (hexane:ethyl acetate=1:1 and then ethyl acetate alone) to give the desired product as a pale yellow oil (2.37 g).

$^1$H-NMR (400 MHz, CDCl$_3$) δ 1.63-1.72 (4H, m), 2.74 (2H, t, J=6.8 Hz), 3.51 (1H, d, J=11.2 Hz), 3.58 (1H, d, J=11.2 Hz), 4.09 (1H, d, J=8.8 Hz), 4.24 (1H, d, J=8.8 Hz), 5.02 (2H, s), 5.28 (1H, br s), 6.87-6.90 (1H, m), 6.94-7.00 (2H, m), 7.09-7.16 (2H, m), 7.22-7.52 (7H, m)

Example 121

4-[4-(3-benzyloxyphenylthio)-2-chlorophenyl]propyl-4-iodomethyl-2-oxazolidinone

To a pyridine solution (30 mL) of the compound of Example 120 (2.37 g), p-toluenesulfonyl chloride (1.33 g) was added and the mixture was stirred at room temperature for 24 hours and at 60° C. for the subsequent 5 hours. Subsequently, water was added and the mixture was extracted with ethyl acetate. The extract was washed sequentially with water, diluted hydrochloric acid, water and then a saturated aqueous solution of sodium chloride. The organic phase was dried over anhydrous sodium sulfate. The solvent was removed and the residue was purified on a silica gel column chromatography (hexane:ethyl acetate=1:1) to give the sulfonate product as a colorless oil (2.14 g). This product (2.14 g) was dissolved in acetone (20 mL), followed by the addition of sodium iodide (2.55 g) and refluxing for 10 hours. Subsequently, water was added and the mixture was extracted with ethyl acetate. The extract was washed with water and a saturated aqueous solution of sodium chloride. The organic phase was then dried over anhydrous sodium sulfate. The solvent was removed and the residue was purified on a silica gel column chromatography (hexane:ethyl acetate=1:1) to give the desired product as a colorless oil (1.47 g).

$^1$H-NMR (400 MHz, CDCl$_3$) δ 1.59-1.65 (2H, m), 1.83-1.89 (2H, m) 2.75 (2H, t, J=7.8 Hz), 3.31 (2H, s), 4.19 (1H, d, J=9.3 Hz), 4.21 (1H, d, J=9.3 Hz), 5.02 (2H, s), 5.13 (1H, br s), 6.88 (1H, dd, J=7.8 Hz, 2.0 Hz), 6.94-7.00 (2H, m), 7.11 (1H, d, J=7.8 Hz), 7.16 (1H, dd, J=7.8 Hz, 2.0 Hz), 7.22-7.41 (7H, m)

Example 122

4-[4-(3-benzyloxyphenylthio)-2-chlorophenyl]propyl-4-methylthiomethyl-2-oxazolidinone

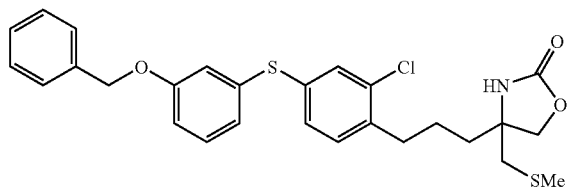

The compound of Example 121 (1.47 g) was dissolved in THF (30 mL), followed by the addition of NaSMe (210 mg) and stirring 2 hours at room temperature. Subsequently, water was added and the mixture was extracted with ethyl acetate. The extract was washed with a saturated aqueous solution of sodium chloride and the organic phase was dried over anhydrous sodium sulfate. The solvent was concentrated under reduced pressure to give the desired product as a colorless oil (1.27 g).

FABMS: 514 ([M+H]$^+$)

$^1$H-NMR (400 MHz, CDCl$_3$) δ 1.62-1.77 (4H, m), 2.17 (3H, s), 2.68 (1H, d, J=13.2 Hz), 2.74 (2H, t, J=7.3 Hz), 2.78 (1H, d, J=13.2 Hz), 4.15 (1H, d, J=9.0 Hz), 4.20 (1H, d, J=9.0 Hz), 5.03 (2H, s), 5.22 (1H, br s), 6.87-6.90 (1H, m), 6.93-6.97 (2H, m), 7.10-7.17 (2H, m), 7.22-7.41 (7H, m)

Example 123

5-[4-(3-benzyloxyphenylthio)-2-chlorophenyl]-2-t-butoxycarbonylamino-2-methylthiomethylpentane-1-ol

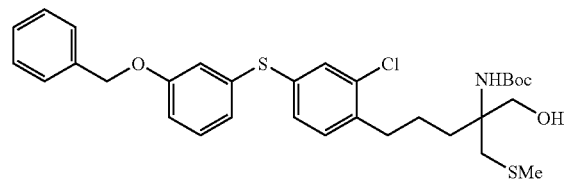

The compound of Example 122 (1.27 g) was dissolved in acetonitrile (20 mL), followed by the addition of Boc$_2$O (1.09 g) and dimethylaminopyridine (100 mg) and stirring at room temperature for 30 min. The solvent was removed under reduced pressure and the residue was purified on a silica gel column chromatography (hexane:ethyl acetate=4:1) to give N-Boc-oxazolidinone product as a colorless oil (1.48 g). This product was dissolved in methanol (20 mL), which was followed by the addition of cesium carbonate (410 mg) and stirring at room temperature overnight. Subsequently, the solvent was removed and the residue was dissolved in ethyl acetate. The solution was washed with hydrochloric acid and then water. The organic phase was dried over anhydrous sodium sulfate. The solvent was removed and the residue was purified on a silica gel column chromatography (hexane:ethyl acetate=2:1) to give the desired product as a colorless oil (1.28 g).

FABMS: 588 ([M+H]$^+$)

$^1$H-NMR (400 MHz, CDCl$_3$) δ 1.43 (9H, s), 1.51-1.66 (3H, m), 1.82-1.85 (1H, m), 2.15 (3H, s), 2.69 (2H, t, J=7.3 Hz), 2.75 (1H, d, J=13.4 Hz), 2.90 (1H, d, J=13.4 Hz), 3.69-3.70 (2H, m), 4.02 (1H, br), 4.99 (1H, br s), 5.02 (2H, s), 6.86-6.94 (3H, m), 7.12-7.17 (2H, m), 7.21-7.41 (7H, m)

Example 124

4-[4-(3-benzyloxyphenylthio)-2-chlorophenyl]propyl-4-fluoromethyl-2-oxazolidinone

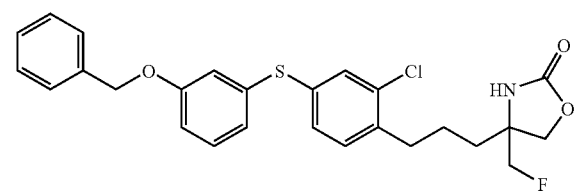

To an acetonitrile solution (10 mL) of the compound of Example 120 (600 mg), triethylamine (0.52 mL) and methanesulfonyl chloride (0.19 mL) were added while the solution was chilled in an ice bath. The mixture was stirred for 10 min. Subsequently, water was added and the solution was separated into an organic phase and an aqueous phase using ethyl acetate and a saturated aqueous solution of sodium chloride. The organic layer was dried over anhydrous sodium sulfate, was concentrated, and was dried in a vacuum pump. This gave 4-[4-(3-benzyloxyphenylthio)-2-chlorophenyl]propyl-4-methanesulfonyloxymethyl-2-oxazolidinone as a yellow oil. The resulting mesylated product was dissolved in THF (6 mL), followed by the addition of a THF solution (6.20 mL) of 1 mol/L tetrabutylammonium fluoride and refluxing for 1 hour. Subsequently, the reaction mixture was allowed to cool to room temperature and was concentrated. The residue was purified on a silica gel column chromatography (hexane:ethyl acetate=1:1) to give the desired product as a colorless amorphous (300 mg).

$^1$H-NMR (400 MHz, CDCl$_3$) δ 1.67-1.70 (4H, m), 2.75 (2H, t, J=7.03), 4.12 (1H, d, J=9.2 Hz), 4.19 (1H, d, J=9.2 Hz), 4.26 (1H, s), 4.38 (1H, s), 5.02 (2H, s), 5.13 (1H, br), 6.88-

6.90 (1H, m), 6.91-6.97 (2H, m), 7.09-7.14 (2H, m), 7.22-7.26 (1H, m), 7.32-7.39 (6H, m)

Example 125

5-[4-(3-benzyloxyphenylthio)-2-chlorophenyl]-2-t-butoxycarbonylamino-2-fluoromethylpentane-1-ol

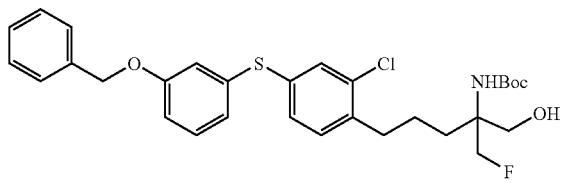

Using the compound of Example 124, the reaction was carried out in the same manner as in Example 123 to give the desired product as a colorless oil.
$^1$NMR (400 MHz, CDCl$_3$) δ 1.64-1.77 (4H, m), 1.47 (9H, s), 2.71 (2H, t, J=7.34), 3.68-3.76 (3H, m), 4.43 (1H, dd, J=9.2 Hz, J=20.2 Hz), 4.55 (1H, dd, J=9.2 Hz, J=20.2 Hz), 4.81 (1H, br), 5.02 (2H, s), 6.86-6.89 (1H, m), 6.92-6.94 (2H, m), 7.11-7.16 (2H, m), 7.21-7.25 (1H, m), 7.30-7.40 (6H, m).

Example 126

Ethyl N-phenyl-2-t-butoxycarbonylamino-5-[4-(3-trifluoromethylphenoxy)phenyl]pentanoate

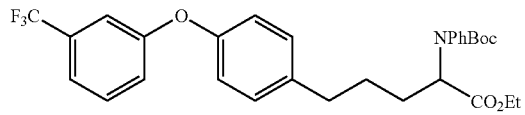

To a THF solution (10 mL) of diethyl 2-phenylaminomalonate (510 mg), Boc$_2$O (480 mg) was added and the mixture was stirred at room temperature for 1 day. To the resulting reaction mixture, NaOtBu (190 mg) and a THF solution (2 mL) of the compound of Reference Example 134 (810 mg) were added and the mixture was refluxed for 8 hours. Subsequently, the mixture was poured into ice water and the mixture was extracted with ethyl acetate. The extract was then washed with a saturated aqueous solution of sodium chloride, and the organic phase was dried over anhydrous sodium sulfate. The solvent was removed and the residue was purified on a silica gel column chromatography (hexane:ethyl acetate=6:1) to give the desired product as a colorless oil (420 mg).
FABMS: 558 ([M+H]$^+$)

Example 127

2-phenylamino-5-[4-(3-trifluoromethylphenoxy)phenyl]pentane-1-ol

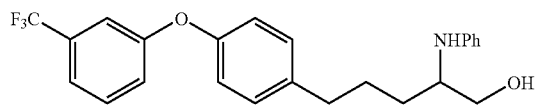

Using the compound of Example 126, the reaction was carried out in the same manner as in Example 39 to give the desired product as a colorless oil.
MS (EI): 415 ([M]$^+$)
$^1$H-NMR (400 MHz, CDCl$_3$) δ 1.56-1.78 (4H, m), 2.62 (2H, t, J=7.8 Hz) 3.51-3.56 (2H, m), 3.73-3.77 (1H, m), 6.66 (2H, d, J=7.8 Hz), 6.73 (1H, t, J=7.8 Hz), 6.91-6.95 (2H, m), 7.11-7.21 (6H, m), 7.31 (1H, d, J=7.8 Hz), 7.41 (1H, t, J=7.8 Hz)

Example 128

5-[4-(3-benzyloxyphenoxy)-2-chlorophenyl]-2-phenylaminopentane-1-ol

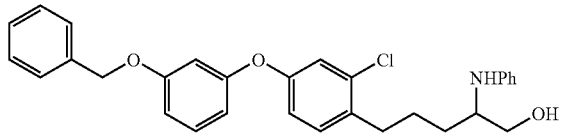

Example 128

2-amino-1-benzoyloxy-5-[4-(3-benzyloxyphenoxy)-2-chlorophenyl]pentane

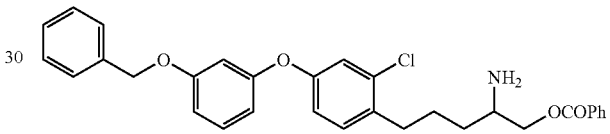

The compound of Example 75 (500 mg) was dissolved in methylene chloride (10 mL). To this solution, pyridine (0.2 mL) and benzoylchloride (0.12 mL) were added and the mixture was stirred at room temperature for 1 hour. Following addition of water, the reaction mixture was extracted with ethyl acetate and the extract was washed sequentially with water and a saturated aqueous solution of sodium chloride. The organic phase was then dried over anhydrous sodium sulfate. The solvent was concentrated and the residue was dissolved in methanol (20 mL). To this solution, ethyl acetate containing 3 mol/L hydrochloric acid (10 mL) was added and the mixture was stirred at room temperature for 1 hour. After concentration, a saturated aqueous solution of sodium bicarbonate was added and the mixture was extracted with ethyl acetate. The organic phase was dried over anhydrous sodium sulfate to give the desired product as a colorless oil (670 mg).

Example 128-2

1-benzoyloxy-5-[4-(3-benzyloxyphenoxy)-2-chlorophenyl]-2-phenylaminopentane

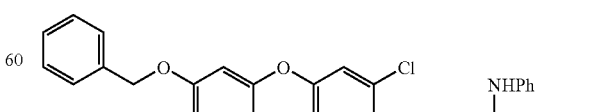

The compound of Example 128-1 (670 mg) was dissolved in methylene chloride (30 mL). To this solution, Ph$_3$Bi(OAc)$_2$ (558 mg) and copper acetate (10 mg) were added and the mixture was stirred at room temperature for 1 day. Subsequently, the solvent was removed and the residue was purified on a silica gel column chromatography (hexane:ethyl acetate=4:1) to give the desired product as a colorless oil (560 mg).

FABMS: 592 ([M+H]$^+$)

Example 128-3

5-[4-(3-benzyloxyphenoxy)-2-chlorophenyl]-2-phenylaminopentane-1-ol

The compound of Example 128-2 (560 mg) was dissolved in ethanol (10 mL). To this solution, a 1 mol/L aqueous solution of sodium hydroxide (5 mL) was added and the mixture was stirred at room temperature for 1 hour. Following addition of water, the mixture was extracted with ethyl acetate and the extract was washed with a saturated aqueous solution of sodium chloride. The organic phase was then dried over anhydrous sodium sulfate. The solvent was concentrated and the residue was purified on a silica gel column chromatography (hexane:ethyl acetate=2:1) to give the desired product as a colorless oil (290 mg).

FABMS: 488 ([M+H]$^+$)

$^1$H-NMR (400 MHz, CDCl$_3$) δ 1.57-1.73 (4H, m), 2.70 (2H, t, J=7.3 Hz), 3.53-3.56 (2H, m), 3.74-3.79 (1H, m), 5.02 (2H, s), 6.57-6.75 (6H, m), 6.82 (1H, dd, J=8.3 Hz, 2.4 Hz), 6.99 (1H, d, J=2.4 Hz), 7.09 (1H, d, J=8.3 Hz), 7.17 (2H, dd, J=8.3 Hz, 7.3 Hz), 7.23 (1H, t, J=8.3 Hz), 7.30-7.42 (5H, m)

Example 129

Methyl 5-[4-(3-benzyloxyphenoxy)-2-chlorophenyl]-2-t-butoxycarbonylaminopentanoate

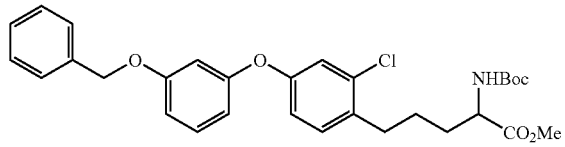

5-[4-(3-benzyloxyphenoxy)-2-chlorophenyl]-2-t-butoxycarbonylaminopentane-1-ol (the compound of Example 75, 4.20 g) was dissolved in DMF (50 mL). To this solution, pyridinium dichromate (9.26 g) was added and the mixture was stirred at room temperature for 17 hours. Following addition of water, the mixture was extracted with ethyl acetate and the extract was washed sequentially with water and a saturated aqueous solution of sodium chloride. The organic phase was then dried over anhydrous sodium sulfate. The solvent was concentrated and the residue was dissolved in DMF (50 mL), followed by the addition of potassium carbonate (2.00 g) and methyl iodide (2 mL) and stirring at room temperature overnight. Subsequently, water was added and the mixture was extracted with ethyl acetate and the extract was washed sequentially with water and a saturated aqueous solution of sodium chloride. The organic phase was then dried over anhydrous sodium sulfate. The solvent was concentrated and the residue was purified on a silica gel column chromatography (hexane:ethyl acetate=4:1) to give the desired methyl ester product as a colorless oil (2.67 g).

$^1$H-NMR (400 MHz, CDCl$_3$) δ 1.44 (9H, s), 1.65-1.88 (4H, m), 2.69-2.71 (2H, m), 3.74 (3H, s), 4.34 (1H, br), 5.00 (1H, br), 5.03 (2H, s), 6.60 (1H, ddd, J=8.0 Hz, 2.2 Hz, 0.7 Hz), 6.63 (1H, t, J=2.4 Hz), 6.75 (1H, ddd, J=8.3 Hz, 2.4 Hz, 0.7 Hz), 6.84 (1H, dd, J=8.3 Hz, 2.4 Hz), 7.00 (1H, d, J=2.4 Hz), 7.13 (1H, d, J=8.3 Hz), 7.24 (1H, t, J=8.0 Hz), 7.30-7.43 (5H, m)

Example 130

6-[4-(3-benzyloxyphenoxy)-2-chlorophenyl]-3-t-butoxycarbonylaminohexane-2-one

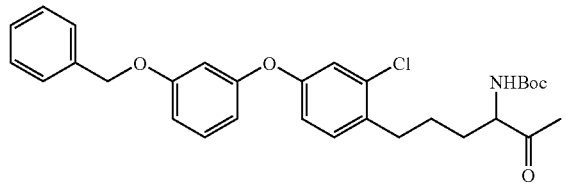

Example 130

N-methoxy-N-methyl-5-[4-(3-benzyloxyphenoxy)-2-chlorophenyl]-2-t-butoxycarbonylaminopentane amide

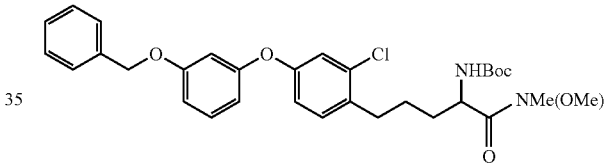

The compound of Example 129 (2.67 g) was dissolved in ethanol (100 mL). To this solution, a 1 mol/L aqueous solution of sodium hydroxide (20 mL) was added and the mixture was stirred at room temperature for 1 hour. Subsequently, hydrochloric acid was added to make the solution acidic and the mixture was extracted with ethyl acetate. The extract was washed sequentially with water and a saturated aqueous solution of sodium chloride, and the organic phase was dried over anhydrous sodium sulfate. The solvent was concentrated under reduced pressure to give the carboxylic acid product as a colorless oil (2.60 g). The resulting carboxylic acid (2.40 g) was dissolved in methylene chloride (50 mL), followed by the addition of MeONHMe.HCl (780 mg), triethylamine (1.1 mL), and WSC (1.53 g) and then stirring at room temperature for 8 hours. Subsequently, water was added and the mixture was extracted with ethyl acetate. The organic phase was then dried over anhydrous sodium sulfate. The solvent was removed and the residue was purified on a silica gel column chromatography (hexane:ethyl acetate=2:1) to give the desired amide as a colorless oil (1.12 g).

$^1$H-NMR (400 MHz, CDCl$_3$) δ 1.43 (9H, s), 1.52-1.78 (4H, m), 2.67-2.77 (2H, m), 3.20 (3H, s), 3.76 (3H, s), 4.73 (1H, br), 5.03 (2H, s), 5.17 (1H, br), 6.59 (1H, dd, J=8.3 Hz, 2.4 Hz), 6.62 (1H, t, J=2.4 Hz), 6.74 (1H, dd, J=8.3 Hz, 2.4 Hz), 6.83 (1H, dd, J=8.3 Hz, 2.4 Hz), 6.99 (1H, d, J=2.4 Hz), 7.14 (1H, d, J=8.3 Hz), 7.23 (1H, t, J=8.3 Hz), 7.28-7.52 (5H, m)

Example 130-2

6-[4-(3-benzyloxyphenoxy)-2-chlorophenyl]-3-t-butoxycarbonylaminohexane-2-one The compound of Example 130-1 (570 mg) was dissolved in THF (15 mL). To this solution, a THF solution (2 mL) of 3 mol/L MeMgBr was added at 0° C. and the mixture was stirred for 3 hours. Following addition of water, the mixture was extracted with ethyl acetate and the extract was washed sequentially with water and a saturated aqueous solution of sodium chloride. The organic phase was then dried over anhydrous sodium sulfate. The solvent was removed and the residue was purified on a silica gel column chromatography (hexane:ethyl acetate=3:1) to give the desired product as a colorless oil (200 mg).

$^1$H-NMR (400 MHz, CDCl$_3$) δ 1.44 (9H, s), 1.53-1.70 (3H, m), 1.93 (1H, br), 2.19 (3H, s), 2.67-2.75 (2H, m), 4.35 (1H, br), 5.03 (2H, s), 5.19 (1H, d, J=7.0 Hz), 6.59 (1H, ddd, J=8.3 Hz, 2.4 Hz, 0.7 Hz), 6.62 (1H, t, J=2.4 Hz), 6.75 (1H, ddd, J=8.3 Hz, 2.4 Hz, 0.7 Hz), 6.84 (1H, dd, J=8.3 Hz, 2.4 Hz), 7.00 (1H, d, J=2.4 Hz), 7.13 (1H, d, J=8.3 Hz), 7.24 (1H, t, J=8.0 Hz), 7.31-7.43 (5H, m)

Example 131

6-[4-(3-benzyloxyphenoxy)-2-chlorophenyl]-3-t-butoxycarbonylaminohexane-2-ol

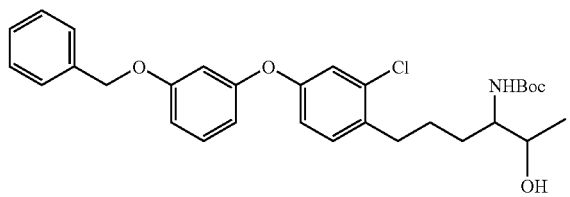

LiBH$_4$ (50 mg) was added to the compound of Example 130 in a mixture of THF (15 mL) and ethanol (3 mL). The mixture was stirred at room temperature for 1 hour. Following addition of water, the mixture was extracted with ethyl acetate and the extract was washed sequentially with water and a saturated aqueous solution of sodium chloride. The organic phase was then dried over anhydrous sodium sulfate. The solvent was concentrated and the residue was purified on a silica gel column chromatography (hexane:ethyl acetate=1:1) to give the desired product as a colorless oil (320 mg).

FABMS: 526 ([M+H]$^+$)

$^1$H-NMR (400 MHz, CDCl$_3$) δ 1.13 (3H, d, J=6.3 Hz), 1.44 (9H, s) 1.64-1.72 (4H, m), 2.64-2.76 (2H, m), 3.67 (1H, br), 3.86 (1H, br) 4.55 (1H, d, J=8.3 Hz), 5.03 (2H, s), 5.19 (1H, d, J=7.0 Hz), 6.60 (1H, dd, J=8.3 Hz, 2.2 Hz), 6.62 (1H, t, J=2.2 Hz), 6.75 (1H, dd, J=8.3 Hz, 2.2 Hz), 6.84 (1H, dd, J=8.3 Hz, 2.4 Hz), 7.00 (1H, d, J=2.4 Hz), 7.14 (1H, d, J=8.3 Hz), 7.24 (1H, t, J=8.0 Hz), 7.29-7.42 (5H, m)

Example 132

3-amino-6-[4-(3-benzyloxyphenoxy)-2-chlorophenyl]hexane-2-ol hydrochloride

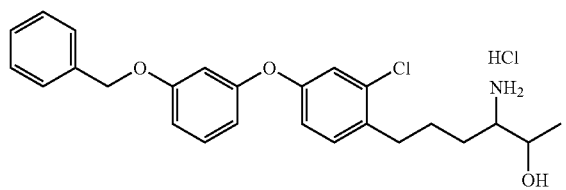

The compound of Example 131 was reacted in the same manner as in Example 76 to give the desired product as a brown amorphous.

FABMS: 426 ([M+H]$^+$)

$^1$H-NMR (400 MHz, DMSO-d$_6$) δ 1.03-1.06 (3H, m), 1.65-1.71 (4H, m) 2.67 (2H, br), 3.03 (1H, br), 3.84-3.87 (1H, m), 5.08 (2H, s), 6.56 (1H, dd, J=8.3 Hz, 2.4 Hz), 6.66 (1H, t, J=2.4 Hz), 6.83 (1H, dd, J=8.3 Hz, 2.4 Hz), 6.94 (1H, dd, J=8.3 Hz, 2.4 Hz), 7.06 (1H, d, J=2.4 Hz), 7.14-7.43 (7H, m), 7.82 (3H, br)

Example 133

5-[4-(3-benzyloxyphenylthio)-2-chlorophenyl]-2-t-butoxycarbonylaminopentanal

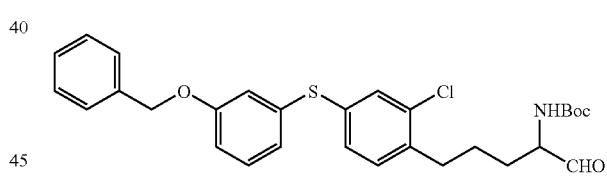

At −78° C., a mixture of DMSO (1.7 mL) and methylene chloride (10 mL) was added to an oxalyl chloride solution (11.0 mL) of methylene chloride (20 mL). To this mixture, a methylene chloride solution (20 mL) of the compound of Example 65 (5.59 g) was added dropwise. After 15 min, triethylamine (7.2 mL) was added and the mixture was stirred at room temperature for 2 hours. Following addition of water, the mixture was extracted with ethyl acetate and the organic phase was dried over anhydrous sodium sulfate. The solvent was concentrated and the residue was purified on a silica gel column chromatography (hexane:ethyl acetate=3:1) to give the desired product as a pale yellow oil (4.75 g).

$^1$H-NMR (400 MHz, CDCl$_3$) δ 1.44 (9H, s), 1.60-1.74 (3H, m), 1.96 (1H, br), 2.72-2.77 (2H, m), 4.28 (1H, br), 5.02 (2H, s), 6.87-6.95 (3H, m), 7.10-7.16 (2H, m), 7.23 (1H, t, J=7.8 Hz), 7.28-7.52 (6H, m), 9.58 (1H, s)

Example 134

6-[4-(3-benzyloxyphenylthio)-2-chlorophenyl]-3-t-butoxycarbonylaminohexane-2-ol

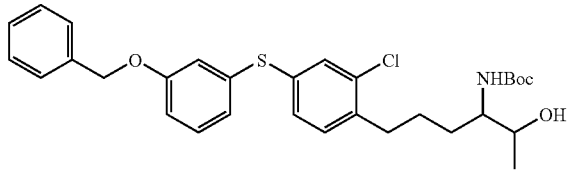

In the same manner as in Example 76, the compound of Example 134 was used to give the desired product as a pale brown oil.

FABMS: 442 ([M+H]$^+$)

$^1$H-NMR (400 MHz, DMSO-d$_6$) δ 1.03 (1H, d, J=6.1 Hz), 1.10 (2H, d, J=6.1 Hz), 1.52-1.65 (4H, m), 2.68 (2H, br s), 2.86-3.02 (1H, m), 3.65-3.84 (1H, m), 5.08 (2H, s), 5.26-5.36 (1H, m), 6.89 (1H, d, J=7.8 Hz), 6.94-7.00 (2H, m), 7.23 (1H, dd, J=7.8 Hz, 1.8 Hz), 7.29-7.41 (8H, m), 7.78-7.82 (3H, br)

Examples 136 through 145

In the same manner as in Example 76, the compounds of 112 through 119, 123 and 125 were used to synthesize the compounds shown in Table 10 below.

TABLE 10

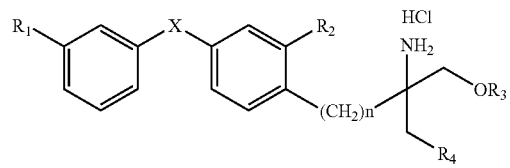

| Examples | R1 | R2 | R3 | R4 | X | n | Characteristics | Yield (%) | FABMS [M + H]$^+$ |
|---|---|---|---|---|---|---|---|---|---|
| 136 | PhCH$_2$O | Cl | H | OMe | O | 3 | Colorless oil | 100 | 456 |
| 137 | PhCH$_2$O | Cl | Me | OMe | O | 3 | Colorless oil | 100 | 470 |
| 138 | CF$_3$ | H | H | OMe | O | 3 | Colorless oil | 92 | 384 |
| 139 | CF$_3$ | H | Me | OMe | O | 3 | Colorless oil | 98 | 398 |
| 140 | PhCH$_2$O | Cl | H | SMe | S | 3 | Colorless amorphous | 100 | 488 |
| 141 | PhCH$_2$O | Cl | H | OMe | S | 2 | Colorless amorphous | 100 | 458 |
| 142 | PhCH$_2$O | Cl | Me | OMe | S | 2 | Colorless amorphous | 92 | 472 |
| 143 | PhCH$_2$O | Cl | H | OMe | S | 3 | Colorless amorphous | 87 | 472 |
| 144 | PhCH$_2$O | Cl | Me | OMe | S | 3 | Colorless amorphous | 90 | 486 |
| 145 | PhCH$_2$O | Cl | H | CH$_2$F | S | 3 | Colorless amorphous | 97 | 460 |

In the same manner as in Example 131, the compound of Example 133 was used to give the desired product as a colorless oil.

FABMS: 542 ([M+H]$^+$)

$^1$H-NMR (400 MHz, CDCl$_3$) δ 1.12 (1H, d, J=6.1 Hz), 1.19 (2H, d, J=6.1 Hz), 1.44 (9H, s), 1.64-1.70 (4H, m), 2.68-2.75 (2H, m), 3.49-3.85 (2H, m), 4.54-4.62 (1H, br), 5.02 (2H, s), 6.86-6.88 (1H, m), 6.91-6.94 (2H, m), 7.14-7.16 (2H, m), 7.22 (1H, t, J=7.8 Hz), 7.26-7.40 (6H, m)

Example 135

3-amino-6-[4-(3-benzyloxyphenylthio)-2-chlorophenyl]hexane-2-ol hydrochloride

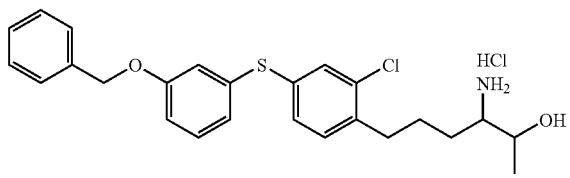

Example 146

4-[4-(3-benzyloxyphenylthio)-2-chlorophenyl]propyl-4-cyanomethyl-2-oxazolidinone

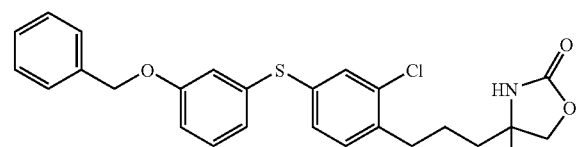

To an ice-chilled acetonitrile solution (8 mL) of the compound of Example 120 (610 mg), triethylamine (0.35 mL) and methanesulfonyl chloride (0.13 mL) were added and the mixture was stirred for 15 min. Subsequently, water was added and the solution was separated into an organic phase and an aqueous phase using ethyl acetate and a saturated aqueous solution of sodium chloride. The organic layer was dried over anhydrous sodium sulfate, was concentrated, and was dried in a vacuum pump. This gave the mesylated product as a yellow oil. This product was dissolved in DMF (2.5 mL), followed by the addition of potassium cyanide (246 mg) and stirring at 70° C. for 2 hours. Subsequently, the reaction mixture was allowed to cool to room temperature and was separated into an organic phase and an aqueous phase using a saturated aqueous solution of sodium bicarbonate and ethyl acetate. The organic layer was dried over anhydrous sodium sulfate and was then concentrated. The residue was purified on a silica gel column chromatography (hexane:ethyl acetate=1:1) to give the desired product as a colorless amorphous (574 mg).

$^1$H-NMR (400 MHz, CDCl$_3$) δ 1.63-1.72 (2H, m), 1.78-1.91 (2H, m) 2.67 (2H, s), 2.73 (2H, t, J=7.3 Hz), 4.21 (2H, s), 5.03 (2H, s), 5.33 (1H, br), 6.89-6.91 (1H, m), 6.95-6.97 (2H, m), 7.09-7.16 (2H, m), 7.22-7.25 (1H, m), 7.27-7.42 (6H, m)

Example 147

3-amino-6-[4-(3-benzyloxyphenylthio)-2-chlorophenyl]-3-hydroxymethylhexanoate hydrochloride

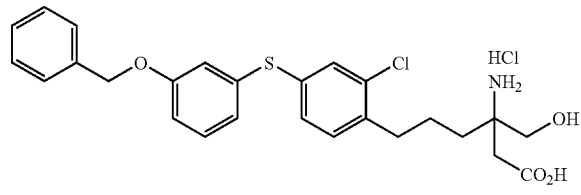

To the compound of Example 146 (196 mg), a 3 mol/L aqueous solution of sodium hydroxide (5 mL) and ethanol (0.5 mL) were added and the mixture was refluxed for 8 hours. While the mixture was stirred in an ice bath, 4 mol/L hydrochloric acid was added to adjust the pH of the mixture to 2 to 1. Using ethyl acetate and water, the mixture was separated into an organic phase and an aqueous phase. The organic layer was dried over anhydrous sodium sulfate, was concentrated, and was dried in a vacuum pump to give the desired product as a pale white solid (201 mg).

$^1$H-NMR (400 MHz, DMSO-d$_6$) δ 1.58-1.71 (4H, m), 2.55 (2H, s), 2.65 (2H, t, J=7.3 Hz), 3.46 (1H, d, J=11.0 Hz), 3.52 (1H, d, J=11.0 Hz), 5.10 (2H s), 5.50 (1H, br), 6.90-6.91 (1H, m), 6.96-7.02 (2H, m), 7.22-7.25 (1H, m), 7.30-7.42 (8H, m), 7.86 (3H, br)

Example 148

3-amino-6-[4-(3-benzyloxyphenylthio)-2-chlorophenyl]-3-hydroxymethylhexanol hydrochloride

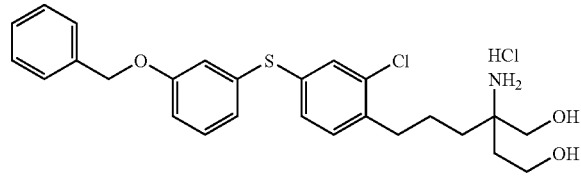

To a dichloromethane solution (8 mL) of the compound of Example 147 (569 mg), triethylamine (303 µL) was added and the mixture was stirred for 5 min. While the mixture was chilled in an ice bath, Boc$_2$O (358 mg) was added and the mixture was stirred for 1 hour. 4N hydrochloric acid was added to adjust the pH of the mixture to 2 to 1. This was followed by the addition of ethyl acetate and a saturated aqueous solution of sodium chloride to separate the mixture into an organic phase and an aqueous phase. The organic layer was dried over anhydrous sodium sulfate, was concentrated, and was dried in a vacuum pump to give a yellow oil. This product was dissolved in DMF (8 mL). To this solution, potassium carbonate (451 mg) and methyl iodide (135 mL) were added and the mixture was stirred at room temperature for 2 hours. The mixture was then extracted with ethyl acetate and the organic layer was dried over anhydrous sodium sulfate and was concentrated. The residue was purified on a silica gel column chromatography (hexane:ethyl acetate=3:1). While chilled in an ice bath, the resultant oil was dissolved in THF (10 mL). To this solution, lithium tetrahydroborate (40.4 mg) and ethanol (1.5 mL) were added and the mixture was stirred in an ice bath for 10 min and at room temperature for the subsequent 1 hour. Following addition of water, 4N hydrochloric acid was added to adjust the pH of the mixture to 2 to 1. Ethyl acetate and water were added to separate the mixture into an organic phase and an aqueous phase. The organic layer was dried over anhydrous sodium sulfate and was concentrated. The residue was purified on a silica gel column chromatography (hexane:ethyl acetate=1:1). Methanol hydrochloride (4 mL) was added to the resultant oil and the mixture was left overnight at room temperature. Subsequently, the solvent was removed to give the desired product as a colorless amorphous (70.0 mg).

$^1$H-NMR (400 MHz, DMSO-d$_6$) δ 1.60 (4H, m), 1.68 (2H, t, J=6.7 Hz), 2.67 (2H, m), 3.41-3.43 (2H, m), 3.50 (2H, t, J=6.7 Hz), 5.10 (2H s), 5.40-5.42 (1H, br), 6.89-6.91 (1H, m), 6.96-7.01 (2H, m), 7.23-7.26 (1H, m), 7.30-7.43 (8H, m), 7.66 (3H, br).

HRMS: 472.1709 (−0.5 mmu)

Example 149

5-[4-(3-benzyloxyphenylthio)-2-chlorophenyl]-2-t-butoxycarbonylamino-2-t-butyldimethylsiloxymethylpentanal

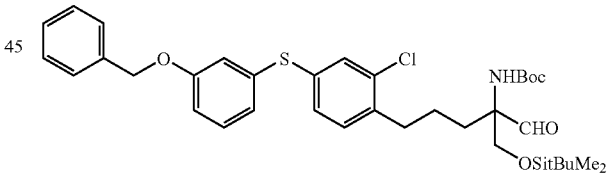

2-[4-(3-benzyloxyphenylthio)-2-chlorophenyl]propyl-2-t-butoxycarbonylamino-1,3-propanediol (19.3 g) was dissolved in DMF (200 mL). To this solution, triethylamine (12.5 mL) and t-BuMe$_2$SiCl (5.12 g) were added and the mixture was stirred at room temperature for 8 hours. Following addition of ice water, the mixture was extracted with ethyl acetate and the extract was washed with water and a saturated aqueous solution of sodium chloride. The organic phase was then dried over anhydrous sodium sulfate. The solvent was removed and the residue was purified on a silica gel column chromatography (hexane:ethyl acetate=10:1) to obtain a monosilyl product (18.0 g) as a colorless oil. This monosilyl product was reacted in the same manner as in Example 133 to give the desired product as a pale yellow oil.

$^1$H-NMR (400 MHz, CDCl$_3$) δ 0.02 (6H, s), 0.84 (9H, s), 1.42 (9H, s) 1.55-1.60 (2H, m), 1.72-1.78 (1H, m), 2.09-2.13

(1H, m), 2.67 (2H, t, J=7.9 Hz), 3.85 (1H, d, J=9.8 Hz), 4.02 (1H, d, J=9.8 Hz), 5.02 (2H, s), 5.31 (1H, br s), 6.86-6.89 (1H, m), 6.91-6.95 (2H, m), 7.08 (1H, d, J=7.9 Hz), 7.13 (1H, dd, J=7.9 Hz, 1.8 Hz), 7.23 (1H, t, J=7.9 Hz), 7.30-7.41 (6H, m), 9.38 (1H, s)

FABMS: 670 ([M+H]$^+$)

Example 150

Ethyl 7-[4-(3-benzyloxyphenylthio)-2-chlorophenyl]-4-t-butoxycarbonylamino-4-t-butyldimethylsiloxymethylheptanoate

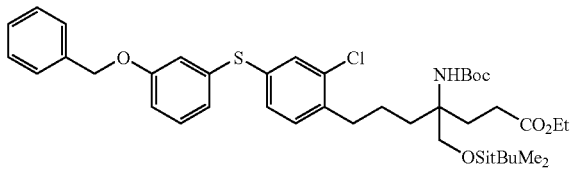

To an ice-chilled THF solution (8 mL) of diethylphosphonoethyl acetate (246 μL), sodium hydride (60%) (50.0 mg) was added and the mixture was stirred for 15 min. A THF solution (7 mL) of the compound of Example 149 (690 mg) was then added and the mixture was stirred for 20 min. Using ethyl acetate and water, the reaction mixture was separated into an organic phase and an aqueous phase. The organic layer was dried over anhydrous sodium sulfate and was concentrated. The residue was purified on a silica gel column chromatography (hexane:ethyl acetate=4:1) to obtain an unsaturated ester as a colorless oil (733 mg). The resultant compound was dissolved in ethyl acetate (8 mL) and 10% palladium carbon (440 mg) was added to the solution. The reaction mixture was then stirred for 4 days under hydrogen atmosphere. Subsequently, palladium carbon was removed by filtration through Celite. The filtrate was concentrated and was dried to give the desired product as a colorless oil (700 mg).

$^1$H-NMR (400 MHz, CDCl$_3$) δ 0.3 (6H, s), 0.87 (9H, s), 1.24 (3H, t, J=7.3 Hz), 1.41 (9H, s), 1.40-1.58 (2H, m), 1.69-1.74 (2H, m), 1.95-1.99 (2H, m), 2.29 (2H, t, J=8.0 Hz), 2.67 (2H, t, J=7.3 Hz), 3.55 (2H, s), 4.12 (2H, q, J=7.3 Hz), 4.51 (1H, br), 5.02 (2H, s), 6.85-6.88 (1H, m), 6.91-6.95 (2H, m), 7.10-7.18 (2H, m), 7.20-7.24 (1H, m), 7.30-7.40 (6H, m).

Example 151

4-amino-7-[4-(3-benzyloxyphenylthio)-2-chlorophenyl]-4-hydroxymethylheptanol hydrochloride

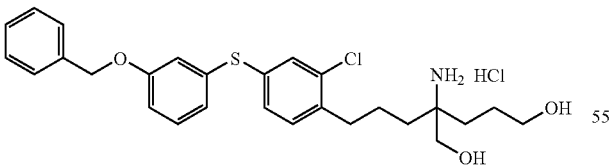

To an ice-chilled THF solution (40 mL) of the compound of Example 150 (690 mg), lithium tetrahydroborate (90.2 mg) and ethanol (5 mL) were added and the mixture was stirred in an ice bath for 1 hour. Subsequently, the mixture was allowed to warm to room temperature and was left overnight. On the next day, lithium tetrahydroborate (90.2 mg) was added twice and the mixture was stirred for 4 hours. Subsequently, water was added and the resulting crystal was removed by filtration. Using ethyl acetate and water, the filtrate was separated into an organic phase and an aqueous phase. The organic layer was dried over anhydrous sodium sulfate and was concentrated. The residue was purified on a silica gel column chromatography (hexane:ethyl acetate=3:1) to obtain a diol product as a colorless oil (552 mg). While chilled in an ice bath, the resulting diol was dissolved in THF (9 mL) and tetrabutylammonium fluoride (1 mol/L-THF, sol.) (945 μL) was added. The resulting mixture was then stirred for 30 min and was left overnight. Subsequently, the reaction mixture was concentrated and the residue was purified on a silica gel column chromatography (hexane:ethyl acetate=1:3) to obtain a colorless oil. Methanol hydrochloride (10 mL) was then added to this product and the mixture was left overnight. The solvent was removed and the residue was dried in a vacuum pump to give the desired product as a colorless solid (363 mg).

$^1$H-NMR (400 MHz, DMSO-d$_6$) δ 1.62-1.82 (8H, m), 2.70 (2H, t, J=7.3 Hz), 3.61-3.67 (4H, m), 4.05 (1H, br), 5.00 (2H, s), 5.30 (1H, br), 6.84-6.87 (1H, m), 6.87-6.94 (2H, m), 7.10-7.23 (3H, m), 7.28-7.39 (6H, m), 7.98 (3H, br).

HRMS: 486.1887 (+1.7 mmu).

Example 152

Ethyl 5-[4-(3-benzyloxyphenylthio)-2-chlorophenyl]-2-ethoxycarbonyl-2-methylpentanoate

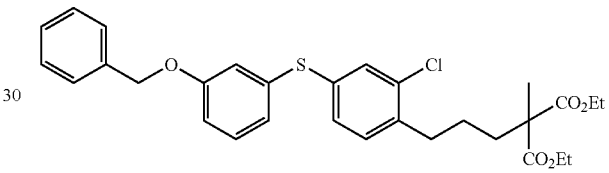

Sodium hydride (242 mg) was dissolved in DMF (5 mL). To this solution, diethylmethylmalonate (0.956 mL) was added and the mixture was stirred for 30 min. A DMF solution (5 mL) of the compound of Reference Example 131 (2.50 g) was then added and the mixture was stirred for 1 hour. Subsequently, the reaction mixture was diluted with water and was extracted with ethyl acetate. The ethyl acetate layer was washed with a saturated aqueous solution of sodium chloride and the organic phase was dried over anhydrous magnesium sulfate and was concentrated. The residue was purified on a silica gel column chromatography (hexane:ethyl acetate=20:1 shifted to 10:1) to give the desired product as a yellow oil (2.74 g).

MS (EI): 540 ([M]$^+$)

$^1$H-NMR (400 MHz, CDCl$_3$) δ 1.23 (6H, t, J=7.3 Hz), 1.40 (3H, s), 1.52-1.60 (2H, m), 1.91-1.95 (2H, m), 2.70 (2H, t, J=7.9 Hz), 4.16 (4H, q, J=7.3 Hz), 5.02 (2H, s), 6.86-6.94 (3H, m), 7.11-7.14 (2H, m), 7.20-7.24 (1H, m), 7.31-7.40 (6H, m)

Example 153

Ethyl 5-[4-(3-benzyloxyphenylthio)-2-chlorophenyl]-2-ethoxycarbonyl-2-ethylpentanoate

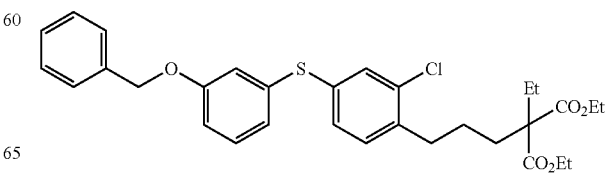

Using diethyl ethylmalonate, the reaction was carried out in the same manner as in Example 152 to give the desired product as a yellow oil.

MS (EI): 554 ([M]$^+$)

$^1$H-NMR (400 MHz, CDCl$_3$) δ 0.80 (3H, t, J=7.3 Hz), 1.22 (6H, t, J=7.3 Hz), 1.45-1.53 (2H, m), 1.89-1.97 (4H, m), 2.70 (2H, t, J=7.3 Hz), 4.16 (4H, q, J=7.3 Hz), 5.02 (2H, s), 6.86-6.94 (3H, m), 7.11-7.16 (2H, m), 7.20-7.24 (1H, m), 7.31-7.40 (6H, m)

Example 154

Ethyl 4-[4-(3-benzyloxyphenylthio)-2-chlorophenyl]-2-ethoxycarbonyl-2-methylbutyrate

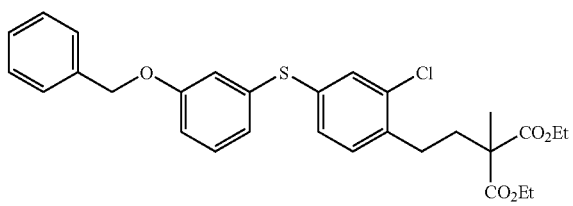

Using the compound of Reference Example 166, the reaction was carried out in the same manner as in Example 152 to give the desired product as a pale yellow oil.

MS (EI): 526 ([M]$^+$)

$^1$H-NMR (400 MHz, CDCl$_3$) δ 1.27 (6H, t, J=7.3 Hz), 1.52 (3H, s), 2.10-2.14 (2H, m), 2.65-2.69 (2H, m), 4.20 (4H, q, J=7.3 Hz), 5.02 (2H, s), 6.86-6.96 (3H, m), 7.15 (2H, s), 7.23 (1H, t, J=8.0 Hz), 7.31-7.41 (6H, m)

Example 155

Ethyl 4-[4-(3-benzyloxyphenylthio)-2-chlorophenyl]-2-ethoxycarbonyl-2-ethylbutyrate

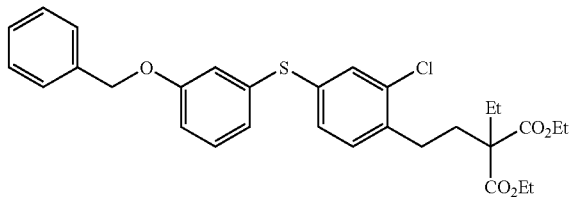

Using the compound of Reference Example 166, the reaction was carried out in the same manner as in Example 153 to give the desired product as a colorless oil.

MS (EI): 540 ([M]$^+$)

$^1$H-NMR (400 MHz, CDCl$_3$) δ 0.82 (3H, t, J=7.3 Hz), 1.17 (6H, t, J=7.3 Hz), 1.93 (2H, q, J=7.3 Hz), 1.98-2.02 (2H, m), 2.45-2.51 (2H, m), 4.13 (4H, q, J=7.3 Hz), 5.10 (2H, s), 6.92-7.01 (3H, m), 7.21 (1H, dd, J=8.0 Hz, 1.9 Hz), 7.30-7.41 (8H, m)

Example 156

5-[4-(3-benzyloxyphenylthio)-2-chlorophenyl]-2-ethoxycarbonyl-2-methylpentanoic acid

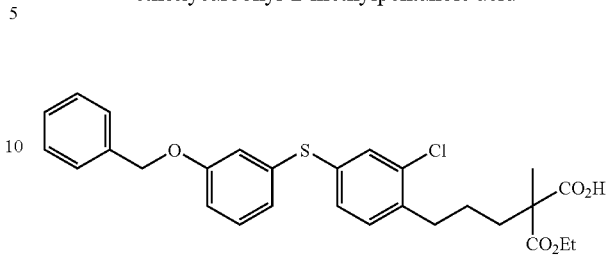

The compound of Example 152 (2.74 g) was dissolved in ethanol (10 mL). To this solution, potassium hydroxide (330 mg) was added and the mixture was stirred at 50° C. overnight. Subsequently, the reaction mixture was diluted with water. 2 mol/L hydrochloric acid was then added and the mixture was extracted with ethyl acetate. The ethyl acetate layer was washed with a saturated aqueous solution of sodium chloride and the organic phase was dried over anhydrous magnesium sulfate and was concentrated. The residue was purified on a silica gel column chromatography (hexane:ethyl acetate=10:1 shifted to 2:1) to give the desired product as a yellow oil (2.38 g).

MS (EI): 512 ([M]$^+$)

$^1$H-NMR (400 MHz, CDCl$_3$) δ 1.26 (3H, t, J=7.3 Hz), 1.47 (3H, s), 1.53-1.62 (2H, m), 1.92-2.03 (2H, m), 2.71 (2H, t, J=7.9 Hz), 4.22 (2H, q, J=7.3 Hz), 5.02 (2H, s), 6.87-6.94 (3H, m), 7.10-7.14 (2H, m), 7.21-7.25 (1H, m), 7.31-7.40 (6H, m)

Example 157

5-[4-(3-benzyloxyphenylthio)-2-chlorophenyl]-2-ethoxycarbonyl-2-ethylpentanoic acid

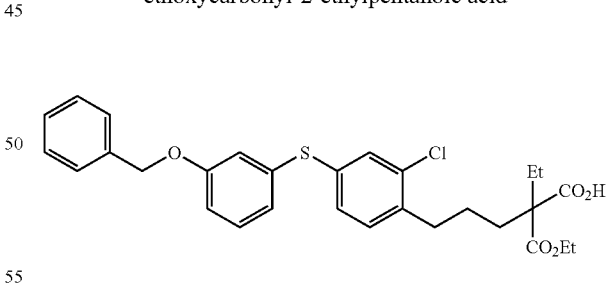

Using the compound of Example 153, the reaction was carried out in the same manner as in Example 156 to give the desired product as a yellow oil.

MS (EI): 526 ([M]$^+$)

$^1$H-NMR (400 MHz, CDCl$_3$) δ 0.84 (3H, t, J=7.3 Hz), 1.28 (3H, t, J=7.3 Hz), 1.42-1.59 (2H, m), 1.85-1.95 (2H, m), 2.00-2.13 (2H, m) 2.66-2.70 (2H, m), 4.23-4.31 (2H, m), 5.02 (2H, s), 6.86-6.94 (3H, m), 7.08-7.15 (2H, m), 7.21-7.25 (1H, m), 7.30-7.40 (6H, m)

Example 158

4-[4-(3-benzyloxyphenylthio)-2-chlorophenyl]-2-ethoxycarbonyl-2-methylbutyric acid

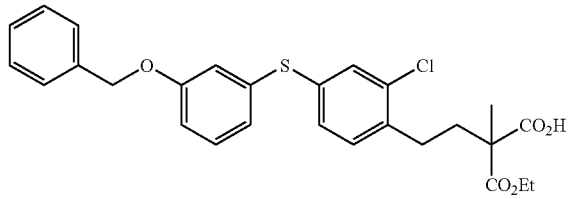

Using the compound of Example 154, the reaction was carried out in the same manner as in Example 156 to give the desired product as a pale yellow oil.

MS (EI): 499 ([M]$^+$)

$^1$H-NMR (400 MHz, CDCl$_3$) δ 1.30 (3H, t, J=7.3 Hz), 1.57 (3H, s), 2.11-2.19 (2H, m), 2.69 (2H, t, J=8.5 Hz), 4.24 (2H, q, J=7.3 Hz), 5.02 (2H, s), 6.87-6.96 (3H, m), 7.14 (2H, s), 7.23 (1H, t, J=8.0 Hz), 7.31-7.40 (6H, m)

Example 159

4-[4-(3-benzyloxyphenylthio)-2-chlorophenyl]-2-ethoxycarbonyl-2-ethylbutyric acid

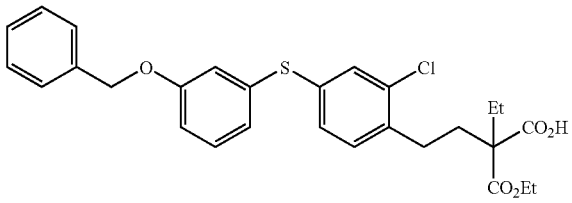

Using the compound of Example 155, the reaction was carried out in the same manner as in Example 156 to give the desired product as a pale yellow oil.

$^1$H-NMR (400 MHz, CDCl$_3$) δ 0.90 (3H, t, J=7.3 Hz), 1.33 (3H, t, J=7.3 Hz), 1.94-1.99 (1H, m), 2.05-2.12 (1H, m), 2.19-2.24 (2H, m), 2.59-2.64 (2H, m), 4.20-4.31 (2H, m), 5.02 (2H, s), 6.87-6.94 (3H, m), 7.09-7.14 (2H, m), 7.23 (1H, t, J=8.0 Hz), 7.29-7.40 (6H, m)

Examples 160 through 162

Diethylpropyl malonate, diethylbutyl malonate or dimethylallyl malonate was reacted in the same manner as in Example 152, which was followed by hydrolysis as described in Example 156 to synthesize the respective compounds shown in Table 11 below.

TABLE 11

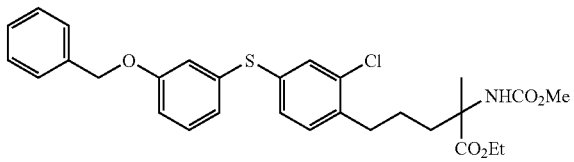

| Examples | R | Characteristics | MS(EI) M$^+$ |
|---|---|---|---|
| 160 | Pr | Yellow oil | 540 |
| 161 | Bu | Yellow oil | 554 |
| 162 | —CH$_2$CH=CH | Yellow oil | — |

Example 163

Ethyl 5-[4-(3-benzyloxyphenylthio)-2-chlorophenyl]-2-methoxycarbonylamino-2-methylpentanoate

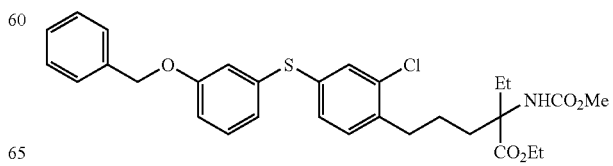

The compound of Example 156 (2.38 g) was dissolved in benzene (20 mL). To this solution, triethylamine (0.711 mL) and DPPA (1.10 mL) were added and the mixture was stirred at room temperature for 10 min, was refluxed, and was further stirred for 1 hour and 30 min. Methanol (3.76 mL) was added over a 30 minute-time period and the mixture was stirred overnight. Subsequently, the reaction mixture was diluted with water and was extracted with ethyl acetate. The ethyl acetate layer was washed with a saturated aqueous solution of sodium chloride, and was then dried over anhydrous magnesium sulfate and was concentrated. The residue was purified on a silica gel column chromatography (hexane:ethyl acetate=20:1 shifted to 5:1) to give the desired product as a yellow oil (2.04 g).

MS (EI): 541 ([M]$^+$)

$^1$H-NMR (400 MHz, CDCl$_3$) δ 1.24 (3H, t, J=7.3 Hz), 1.36-1.40 (1H, m), 1.54 (3H, s), 1.56-1.65 (1H, m), 1.80-1.87 (1H, m), 2.28 (1H, m), 2.65-2.69 (2H, m), 3.63 (3H, s), 4.15-4.22 (2H, m), 5.02 (2H, s), 5.61 (1H, br s), 6.86-6.94 (3H, m), 7.09-7.15 (2H, m), 7.20-7.24 (1H, m), 7.31-7.40 (6H, m)

Example 164

Ethyl 5-[4-(3-benzyloxyphenylthio)-2-chlorophenyl]-2-ethyl-2-methoxycarbonylaminopentanoate Using the compound of Example 157, the reaction was carried out in the same manner as in Example 163 to give the desired product as a yellow oil.

MS (EI): 555 ([M]+)

¹H-NMR (400 MHz, CDCl₃) δ 0.74 (3H, t, J=7.3 Hz), 1.24 (3H, t, J=7.3 Hz), 1.28-1.32 (1H, m), 1.57-1.58 (1H, m), 1.70-1.84 (2H, m) 2.34-2.44 (2H, m), 2.62-2.72 (2H, m), 3.63 (3H, s), 4.16-4.22 (2H, m), 5.02 (2H, s), 5.78 (1H, br s), 6.86-6.94 (3H, m), 7.08-7.15 (2H, m), 7.20-7.24 (1H, m), 7.31-7.40 (6H, m)

Example 165

Ethyl 4-[4-(3-benzyloxyphenylthio)-2-chlorophenyl]-2-t-butoxycarbonylamino-2-methylbutyrate

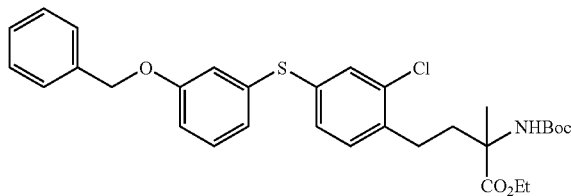

Using t-butanol in place of methanol, the compound of Example 158 was reacted in the same manner as in Example 163 to give the desired product as a pale yellow oil.

MS (FAB+): 569 ([M+H]+)

¹H-NMR (400 MHz, CDCl₃) δ 1.29 (3H, t, J=7.3 Hz), 1.46 (9H, s), 1.58 (3H, s), 2.10 (1H, td, J=13.0 Hz, 4.9 Hz), 2.41 (1H, br), 2.53 (1H, td, J=13.0 Hz, 4.9 Hz), 2.67 (1H, td, J=13.0 Hz, 4.9 Hz), 4.19 (2H, q, J=7.3), 5.02 (2H, s), 5.46 (1H, br s), 6.86-6.94 (3H, m), 7.08-7.15 (2H, m), 7.23 (1H, t, J=8.0 Hz), 7.30-7.40 (6H, m)

Example 166

Ethyl 4-[4-(3-benzyloxyphenylthio)-2-chlorophenyl]-2-ethyl-2-methoxycarbonylaminobutyrate

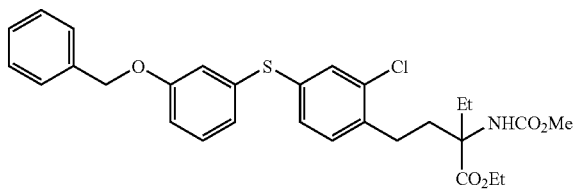

Using the compound of Example 159, the reaction was carried out in the same manner as in Example 163 to give the desired product as a pale yellow oil.

MS (EI): 541 ([M]+)

¹H-NMR (400 MHz, CDCl₃) δ 0.77 (3H, t, J=7.3 Hz), 1.30 (3H, t, J=7.3 Hz), 1.75-1.80 (1H, m), 2.05-2.15 (1H, m), 2.36-2.49 (2H, m), 2.59-2.68 (2H, m), 3.66 (3H, s), 4.11-4.27 (2H, m), 5.02 (2H, s), 5.87 (1H, br), 6.86-6.93 (3H, m), 7.08-7.14 (2H, m), 7.22 (1H, t, J=8.0 Hz), 7.30-7.40 (6H, m)

Examples 167 through 169

Using the compounds shown in Table 11, the reaction was carried out in the same manner as in Example 163 to give the respective compounds shown in Table 12 below.

TABLE 12

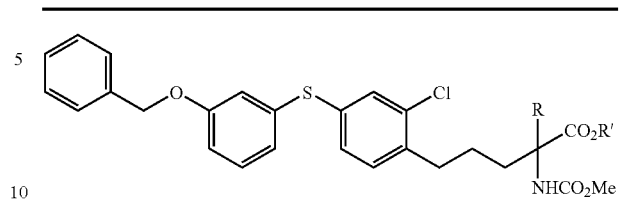

| Examples | R | R' | Characteristics | MS(EI) M+ |
|---|---|---|---|---|
| 167 | Pr | Et | Colorless oil | 569 |
| 168 | Bu | Et | Colorless oil | — |
| 169 | —CH₂CH=CH | Me | Yellow oil | 554* |

*FABMS

Example 169

5-[4-(3-benzyloxyphenylthio)-2-chlorophenyl]-2-methoxycarbonylamino-2-methylpentane-1-ol

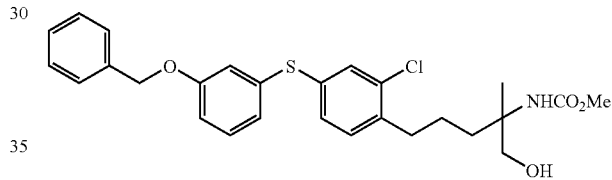

Using the compound of Example 163, the reaction was carried out in the same manner as in Example 39 to give the desired product as a colorless oil.

MS (EI): 499 ([M]+)

¹H-NMR (400 MHz, CDCl₃) δ 1.18 (3H, s), 1.57-1.84 (4H, m), 2.71 (2H, t, J=7.3 Hz), 3.59-3.69 (3H, m), 3.63 (3H, s), 4.71 (1H, br s), 5.02 (2H, s), 6.86-6.94 (3H, m), 7.13-7.17 (2H, m), 7.21-7.25 (1H, m), 7.30-7.41 (6H, m)

Examples 170 and 171

(+)-5-[4-(3-benzyloxyphenylthio)-2-chlorophenyl]-2-methoxycarbonylamino-2-methylpentane-1-ol and
(−)-5-[4-(3-benzyloxyphenylthio)-2-chlorophenyl]-2-methoxycarbonylamino-2-methylpentane-1-ol The compound of Example 169 was optically resolved by HPLC (Chiralcel OD, hexane:isopropanol=70:30, wavelength=UV 254 nm, flow rate=3 mL/min).

A compound with an optical rotation of $[\alpha]^{24.0}_D$ +15° (C=1.0, chloroform) and a compound with an optical rotation of $[\alpha]^{24.7}_D$ −12° (C=1.0, chloroform) were obtained from the first elution fraction and the second elution fraction, respectively.

Example 172

5-[4-(3-benzyloxyphenylthio)-2-chlorophenyl]-2-ethyl-2-methoxycarbonylaminopentane-1-ol

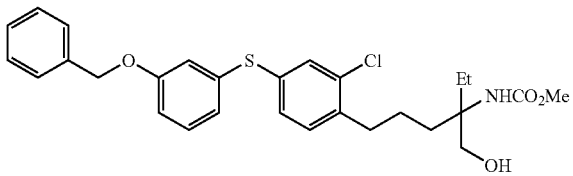

Using the compound of Example 164, the reaction was carried out in the same manner as in Example 39 to give the desired product as a pale yellow oil.

MS (EI): 513 ([M]+)

$^1$H-NMR (400 MHz, CDCl$_3$) δ 0.83 (3H, t, J=7.3 Hz), 1.51-1.73 (6H, m) 2.70 (2H, t, J=7.3 Hz), 3.63 (3H, s), 3.65-3.70 (3H, m), 4.63 (1H, br s), 5.02 (2H, s), 6.86-6.94 (3H, m), 7.12-7.17 (2H, m), 7.20-7.24 (1H, m), 7.30-7.40 (6H, m)

Examples 173 and 174

(+)-5-[4-(3-benzyloxyphenylthio)-2-chlorophenyl]-2-ethyl-2-methoxycarbonylaminopentane-1-ol and
(−)-5-[4-(3-benzyloxyphenylthio)-2-chlorophenyl]-2-ethyl-2-methoxycarbonylaminopentane-1-ol The compound of Example 172 was optically resolved by HPLC (Chiralcel OD, hexane:isopropanol=60:40, wavelength UV 254 nm, flow rate=3 mL/min). A compound with an optical rotation of $[\alpha]^{25.6}_D$ +14° (C=1.0, chloroform) and a compound with an optical rotation of $[\alpha]^{25.6}_D$ −15°(C=1.0, chloroform) were obtained from the first elution fraction and the second elution fraction, respectively.

Example 175

4-[4-(3-benzyloxyphenylthio)-2-chlorophenyl]--t-butoxycarbonylamino-2-methylbutane-1-ol

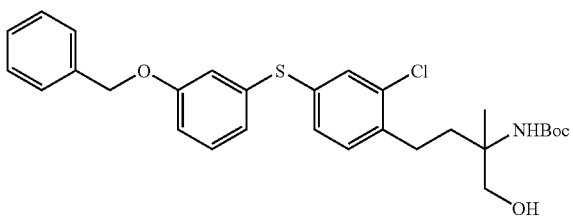

Using the compound of Example 165, the reaction was carried out in the same manner as in Example 39 to give the desired product as a colorless oil.

MS (EI): 527 ([M]+)

$^1$H-NMR (400 MHz, CDCl$_3$) δ 1.25 (3H, s), 1.44 (9H, s), 1.82 (1H, td, J=13.0 Hz, 4.9 Hz), 2.06 (1H, td, J=13.0 Hz, 4.9 Hz), 2.65-2.80 (2H, m), 3.66-3.74 (2H, m), 4.68 (1H, br s), 6.86-6.94 (3H, m), 7.15 (2H, s), 7.23 (1H, t, J=8.0 Hz), 7.32-7.40 (6H, m)

Examples 176 and 177

(+)-4-[4-(3-benzyloxyphenylthio)-2-chlorophenyl]-2-t-butoxycarbonylamino-2-methylbutane-1-ol
および(−)-4-[4-(3-benzyloxyphenylthio)-2-chlorophenyl]-2-t-butoxycarbonylamino-2-methylbutane-1-ol The compound of Example 175 was optically resolved by HPLC (Chiralpak AD, hexane:ethanol=85:15, wavelength=UV 254 nm, flow rate=3 mL/min). A compound with an optical rotation of $[\alpha]^{25.3}_D$ +4.6° (C=1.0, chloroform) and a compound with an optical rotation of $([\alpha]^{25.6}_D$ −2.2° (C=1.0, chloroform) were obtained from the first elution fraction and the second elution fraction, respectively.

Example 178

4-[4-(3-benzyloxyphenylthio)-2-chlorophenyl]-2-ethyl-2-methoxycarbonylamino-butane-1-ol

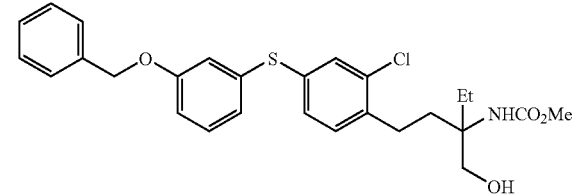

Using the compound of Example 166, the reaction was carried out in the same manner as in Example 39 to give the desired product as a colorless oil.

MS (EI): 499 ([M]+)

$^1$H-NMR (400 MHz, CDCl$_3$) δ 0.94 (3H, t, J=7.3 Hz), 1.69 (2H, q, J=7.3 Hz), 1.80-1.94 (2H, m), 2.62-2.75 (2H, m), 3.65 (3H, s), 3.77 (3H, m), 4.77 (1H, br), 5.02 (2H, s), 6.86-6.95 (3H, m), 7.16 (2H, s), 7.23 (1H, t, J=8.0 Hz), 7.32-7.41 (6H, m)

Examples 179 and 180

(+)-4-[4-(3-benzyloxyphenylthio)-2-chlorophenyl]-2-ethyl-2-methoxycarbonylamino-butane-1-ol and
(−)-4-[4-(3-benzyloxyphenylthio)-2-chlorophenyl]-2-ethyl-2-methoxycarbonylamino-butane-1-ol The compound of Example 178 was optically resolved under similar conditions to Examples 173 and 174. A compound with an optical rotation of $[\alpha]^{25.6}_D$ +11.1°(C=1.0, chloroform) and a compound with an optical rotation of $[\alpha]^{26.1}_D$ −9.67° (C=1.0, chloroform) were obtained from the first elution fraction and the second elution fraction, respectively.

Examples 181 through 183

Using the compounds shown in Table 12, the reaction was carried out in the same manner as in Example 39 to give the respective compounds shown in Table 13 below.

TABLE 13

[Structure: benzyloxyphenyl-thio-chlorophenyl chain with R, OH, NHCO₂Me substituents]

| Examples | R | Characteristics | FABMS [M + H]+ |
|---|---|---|---|
| 181 | Pr | Colorless oil | 528 |
| 182 | Bu | Colorless oil | — |
| 183 | —CH₂CH=CH | Colorless oil | 526 |

Example 184

(+)-2-amino-5-[4-(3-benzyloxyphenylthio)-2-chlorophenyl]-2-methylpentane-1-ol

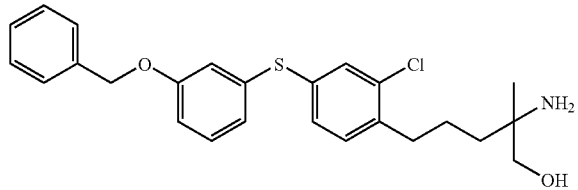

The compound of Example 169 (527 mg) was dissolved in a mixed solvent composed of a 5 mol/L aqueous solution of potassium hydroxide (2 mL), tetrahydrofuran (2 mL), and methanol (3 mL). The mixture was refluxed and was then stirred for 4 days. Subsequently, the reaction mixture was diluted with water and was extracted with ethyl acetate. The ethyl acetate layer was washed with a saturated aqueous solution of sodium chloride and was dried over anhydrous magnesium sulfate and was concentrated. The residue was purified on a silica gel column chromatography (aminated silica gel, ethyl acetate:ethanol=20:1) to give the desired product as a pale yellow oil (311 mg).

MS (FAB+): 442 ([M+H]+)

$^1$H-NMR (400 MHz, CDCl$_3$) δ 1.04 (3H, s), 1.37-1.67 (4H, m), 2.70 (2H, t, J=7.3 Hz), 3.29 (2H, q, J=9.2 Hz), 5.02 (2H, s), 6.86-6.94 (3H, m), 7.12-7.17 (2H, m), 7.21-7.25 (1H, m), 7.31-7.41 (6H, m)

Example 185

(+)-2-amino-5-[4-(3-benzyloxyphenylthio)-2-chlorophenyl]-2-methylpentane-1-ol

Using the compound of Example 170, the reaction was carried out in the same manner as in Example 184 to give the desired product as a pale yellow oil.

Elemental analysis (%): C$_{25}$H$_{28}$ClNO$_2$S.1/3H$_2$O

|  | C | H | N |
|---|---|---|---|
| Calcd: | 67.00 | 6.45 | 3.13 |
| Found: | 67.03 | 6.51 | 3.20 |

$[α]^{25.2}_D$ +2.0° (C=1.0, chloroform)

Example 186

(−)-2-amino-5-[4-(3-benzyloxyphenylthio)-2-chlorophenyl]-2-methylpentane-1-ol

Using the compound of Example 171, the reaction was carried out in the same manner as in Example 184 to give the desired product as a pale yellow oil.

Elemental analysis (%): C$_{25}$H$_{28}$ClNO$_2$S.1/4H$_2$O

|  | C | H | N |
|---|---|---|---|
| Calcd: | 67.23 | 6.44 | 3.14 |
| Found: | 67.19 | 6.44 | 3.15 |

$[α]^{25.5}_D$ −2.6° (C=1.0, chloroform)

Example 187

5-[4-(3-benzyloxyphenylthio)-2-chlorophenyl]-2-butoxycarbonylamino-2-ethylpentane-1-ol

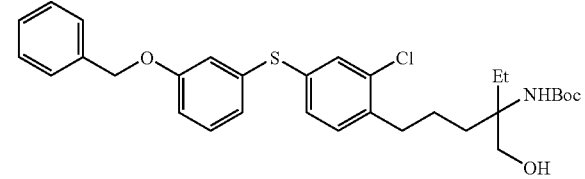

Using t-butanol in place of methanol, the compound of Example 157 was reacted in the same manner as in Example 163, followed by reduction to give the desired product as a colorless oil.

MS (EI): 555 ([M]+)

$^1$H-NMR (400 MHz, CDCl$_3$) δ 0.83 (3H, t, J=7.3 Hz), 1.42 (9H, s) 1.55-1.72 (6H, m), 2.70 (2H, t, J=6.7 Hz), 3.64-3.66 (2H, m), 4.49 (1H, br s), 5.02 (2H, s), 6.82-6.95 (3H, m), 7.12-7.17 (2H, m), 7.20-7.25 (1H, m), 7.30-7.41 (6H, m)

Example 188

(±)-2-amino-5-[4-(3-benzyloxyphenylthio)-2-chlorophenyl]-2-ethylpentane-1-ol hydrochloride

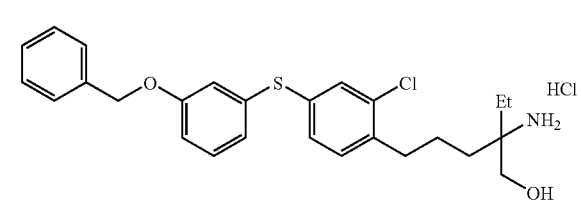

Using the compound of Example 187, the reaction was carried out in the same manner as in Example 76 to give the desired product as a pale yellow amorphous.

MS (HR-FAB+): 456.1789

$^1$H-NMR (400 MHz, CDCl$_3$) δ 0.93 (3H, t, J=7.3 Hz), 1.65-1.75 (6H, m) 2.69 (2H, m), 3.66 (2H, m), 4.21 (1H, br s), 5.00 (2H, s), 6.84-6.94 (3H, m), 7.12-7.23 (3H, m), 7.29-7.39 (6H, m)

Example 189

(+)-2-amino-5-[4-(3-benzyloxyphenylthio)-2-chlorophenyl]-2-ethylpentane-1-ol

Using the compound of Example 173, the reaction was carried out in the same manner as in Example 184 to give the desired product as a pale yellow oil.

MS (HR-FAB+): 456.1753

Elemental analysis (%): $C_{26}H_{30}ClNO_2S \cdot 2/5H_2O$

|        | C     | H    | N    |
|--------|-------|------|------|
| Calcd: | 67.39 | 6.71 | 3.03 |
| Found: | 67.35 | 6.74 | 2.89 |

$[\alpha]^{25.2}_D$ +1.4° (C=1.0, chloroform)

Example 190

(−)-2-amino-5-[4-(3-benzyloxyphenylthio)-2-chlorophenyl]-2-ethylpentane-1-ol

Using the compound of Example 174, the reaction was carried out in the same manner as in Example 184 to give the desired product as a pale yellow oil.

MS (HR-FAB+): 456.1773

Elemental analysis (%): $C_{26}H_{30}ClNO_2S \cdot 2/5H_2O$

|        | C     | H    | N    |
|--------|-------|------|------|
| Calcd: | 67.39 | 6.71 | 3.03 |
| Found: | 67.25 | 6.62 | 2.94 |

$[\alpha]^{25.5}_D$ −2.0° (C=1.0, chloroform)

Example 191

(+)-2-amino-4-[4-(3-benzyloxyphenylthio)-2-chlorophenyl]-2-methylbutane-1-ol hydrochloride

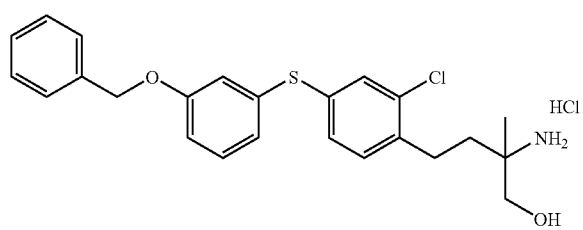

Using the compound of Example 175, the reaction was carried out in the same manner as in Example 76 to give the desired product as a colorless powder.

MS (FAB+): 428 ([M+H]⁺)

¹H-NMR (400 MHz, DMSO-d₆) δ 1.22 (3H, s), 1.72-1.76 (2H, m), 2.70 (2H, t, J=8.5 Hz), 3.39-3.43 (1H, m), 3.47-3.50 (1H, m), 5.10 (2H, s), 5.54 (1H, m), 6.90-7.02 (3H, m), 7.24-7.42 (9H, m), 7.77 (3H, br).

MP=150-153° C. (iPr₂O)

Example 192

(+)-2-amino-4-[4-(3-benzyloxyphenylthio)-2-chlorophenyl]-2-methylbutane-1-ol hydrochloride Using the compound of Example 176, the reaction was carried out in the same manner as in Example 76 to give the desired product as a colorless powder.

MS (FAB+): 428 ([M+H]⁺)

$[\alpha]^{24.9}_D$ +3.8° (C=1.0, methanol)

MP=157-159° C. (iPr₂O)

Example 193

(−)-2-amino-4-[4-(3-benzyloxyphenylthio)-2-chlorophenyl]-2-methylbutane-1-ol hydrochloride Using the compound of Example 177, the reaction was carried out in the same manner as in Example 76 to give the desired product as a colorless powder.

MS (FAB+): 428 ([M+H]⁺)

$[\alpha]^{24.5}_D$ +4.3° (C=1.0, methanol)

MP=155-158° C. (iPr₂O)

Example 194

(±)-2-amino-4-[4-(3-benzyloxyphenylthio)-2-chlorophenyl]-2-ethylbutane-1-ol

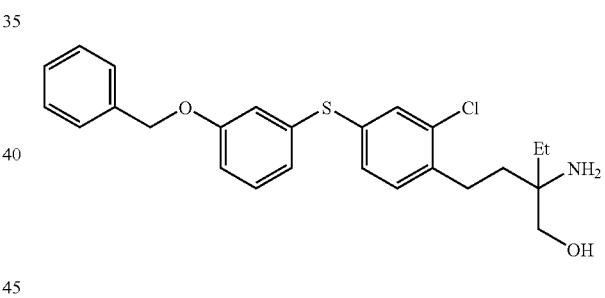

Using the compound of Example 178, the reaction was carried out in the same manner as in Example 184 to give the desired product as a pale yellow oil.

MS (FAB+): 442 ([M+H]⁺)

¹H-NMR (400 MHz, CDCl₃) δ 0.93 (3H, t, J=7.3 Hz), 1.38-1.71 (4H, m) 2.64-2.71 (2H, m), 3.40 (2H, s), 5.02 (2H, s), 6.86-6.93 (3H, m), 7.15 (2H, s), 7.23 (1H, t, J=8.0 Hz), 7.31-7.40 (6H, m)

Example 195

(+)-2-amino-4-[4-(3-benzyloxyphenylthio)-2-chlorophenyl]-2-ethylbutane-1-ol

Using the compound of Example 180, the reaction was carried out in the same manner as in Example 184 to give the desired product as a colorless oil.

MS (FAB+): 442 ([M+H]⁺)

$[\alpha]^{28.5}_D$ +2.7° (C=1.0, chloroform)

Example 196

(−)-2-amino-4-[4-(3-benzyloxyphenylthio)-2-chlorophenyl]-2-ethylbutane-1-ol

Using the compound of Example 179, the reaction was carried out in the same manner as in Example 184 to give the desired product as a colorless oil.
MS (FAB+): 442 ([M+H]$^+$)
[α]$^{28.5}_D$ −3.3° (C=1.0, chloroform)

Examples 197 through 199

The compounds shown in Table 13 were reacted in the same manner as in Example 184 to give the respective compounds shown in Table 14 below.

TABLE 14

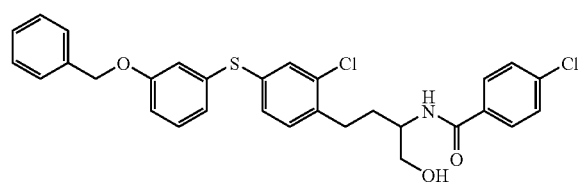

| Examples | R | Characteristics | FABMS [M + H]$^+$ |
|---|---|---|---|
| 197 | Pr | Colorless oil | 470 |
| 198 | Bu | Colorless oil | 484 |
| 199 | —CH$_2$CH=CH | Colorless oil | 468 |

Example 200

4-[4-(3-benzyloxyphenylthio)-2-chlorophenyl]-2-(4-chlorobenzoyl)aminobutanol

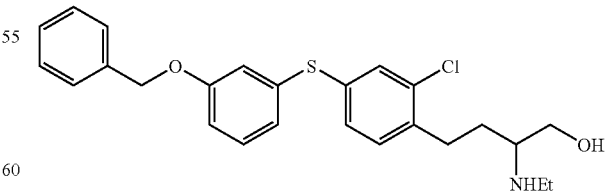

A methylene chloride solution (30 mL) containing the compound of Example 101 (900 mg), p-chlorobenzoic acid (470 mg), WSC (575 mg), and triethylamine (0.84 mL) was stirred at room temperature for 8 hours. Subsequently, water was added and the mixture was extracted with ethyl acetate. The extract was washed sequentially with water, diluted hydrochloric acid, water, a saturated aqueous solution of sodium bicarbonate, and a saturated aqueous solution of sodium chloride. The organic phase was then dried over anhydrous sodium sulfate. The solvent was concentrated and the residue was purified on a silica gel column chromatography (hexane:ethyl acetate=1:1) to obtain the desired product as a colorless oil (800 mg).
FABMS: 552 ([M+H]$^+$)
$^1$H-NMR (400 MHz, CDCl$_3$) δ 1.88-2.00 (2H, m), 2.37 (1H, br), 2.76-2.88 (2H, m), 3.73-3.84 (2H, m), 4.20-4.24 (1H, m), 5.02 (2H, s), 6.33 (1H, d, J=8.0 Hz), 6.88 (1H, dd, J=7.3 Hz, 1.8 Hz), 6.90-6.94 (2H, m), 7.13 (1H, dd, J=8.0 Hz, 1.8 Hz), 7.17 (1H, d, J=8.0 Hz), 7.23 (1H, d, J=8.0 Hz), 7.30-7.39 (6H, m), 7.41 (2H, d, J=8.6 Hz), 7.69 (2H, d, J=8.6 Hz)

Example 201

2-acetylamino-4-[4-(3-benzyloxyphenylthio)-2-chlorophenyl]butane-1-ol

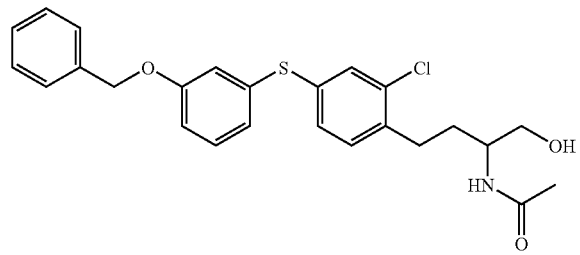

To a methylene chloride solution (80 mL) of the compound of Example 101 (5.55 g), triethylamine (6.86 ml), and acetyl chloride (3.50 ml) were added while the mixture was chilled on an ice bath. The mixture was stirred for 4 hours, followed by the addition of water. The solvent was removed under reduced pressure and the mixture was extracted with ethyl acetate. The extract was washed with a saturated aqueous solution of sodium chloride, and the organic phase was dried over anhydrous sodium sulfate and was concentrated. The residue was purified on a silica gel column chromatography (ethyl acetate) to obtain an N,O-diacetylated product as a colorless powder (4.21 g). This compound (620 mg) was dissolved in ethanol (2.00 mL). To this solution, a 5N aqueous solution of potassium hydroxide (0.25 mL) was added and the mixture was stirred at room temperature for 1 hour. The solvent was removed under reduced pressure and the mixture was extracted with ethyl acetate. The extract was washed with a saturated aqueous solution of sodium chloride, and the organic phase was dried over anhydrous sodium sulfate and was concentrated. This gave the desired product as a colorless powder (552 mg).
FABMS: 456 ([M+H]$^+$)
$^1$H-NMR (400 MHz, CDCl$_3$) δ 1.72-1.89 (2H, m), 2.02 (3H, s), 2.69-2.83 (2H, m), 3.63 (1H, dd, J=11.0 Hz, 5.0 Hz), 3.71 (1H, dd, J=11.0 Hz, 3.0 Hz), 3.98-4.01 (1H, m), 4.20-4.29 (1H, m), 5.02 (2H, s), 5.70 (1H, d, J=7.9), 6.87-6.95 (3H, m), 7.15 (2H, s), 7.23 (1H, t, J=8.4 Hz), 7.31-7.41 (6H, m)
MP=78-81° C. (EtOH)

Example 202

4-[4-(3-benzyloxyphenylthio)-2-chlorophenyl]-2-ethylaminobutane-1-ol

The N,O-diacetylated product (1.00 g) obtained in Example 201 was dissolved in tetrahydrofuran (10 mL). To this solution, lithium aluminum hydride (191 mg) was added while the solution was chilled on an ice bath. The mixture was stirred for 2 hours. Subsequently, a 1 mol/L aqueous solution of potassium hydroxide was added dropwise. This was followed by the addition of water to dilute the mixture. The mixture was then filtrated through Celite and the solvent was concentrated. The residue was purified on a silica gel column chromatography (aminated silica gel, ethyl acetate) to give the desired product as a colorless oil (210 mg).

FABMS: 442 ([M+H]$^+$)

$^1$H-NMR (400 MHz, CDCl$_3$) δ 1.10 (3H, t, J=7.3), 1.63-1.80 (2H, m) 1.82 (1H, br), 2.58-2.75 (5H, m), 3.36 (1H, dd, J=10.5 Hz, 6.4 Hz), 3.67 (1H, dd, J=10.5 Hz, 4.0 Hz), 5.01 (2H, s), 6.86-6.94 (3H, m), 7.14 (2H, s), 7.23 (1H, t, J=7.3 Hz), 7.31-7.40 (6H, m)

Example 203

5-[4-(3-benzyloxyphenylsulfinyl)-2-chlorophenyl]-2-t-butoxycarbonylaminopentane-1-ol

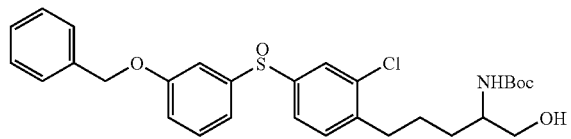

To a methylene chloride solution (20 mL) of the compound of Example 102, m-chlorobenzoic acid (588 mg) was added while the mixture was chilled on an ice bath. The mixture was stirred for 30 min. Following addition of a saturated aqueous solution of sodium bicarbonate, the solvent was removed under reduced pressure and the mixture was extracted with ethyl acetate. The extract was washed with a saturated aqueous solution of sodium chloride, and the organic phase was dried over anhydrous sodium sulfate and was concentrated. The residue was purified on a silica gel column chromatography (ethyl acetate:hexane=2:1) to give the compound of Example 203 as a colorless amorphous (1.04 g) and the compound of Example 204 as a colorless amorphous (180 mg).

FABMS: 544 ([M+H]$^+$)

$^1$H-NMR (400 MHz, CDCl$_3$) δ 1.43 (9H, s), 1.54-1.69 (5H, m), 2.72-2.78 (2H, m), 3.52-3.57 (1H, m), 3.67 (2H, d, J=8.5 Hz), 4.63 (1H, br), 5.10 (1H, s), 7.05 (1H, dd, J=8.6 Hz, 2.0 Hz), 7.19 (1H, d, J=7.9 Hz), 7.26-7.30 (2H, m), 7.31-7.42 (7H, m), 7.60 (1H, d, J=1.2 Hz)

Example 204

5-[4-(3-benzyloxyphenylsulfonyl)-2-chlorophenyl]-2-t-butoxycarbonylaminopentane-1-ol

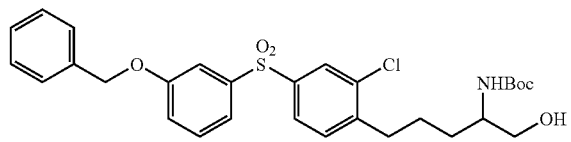

Colorless amorphous (See Example 203).

FABMS: 560 ([M+H]$^+$)

$^1$H-NMR (400 MHz, CDCl$_3$) δ 1.43 (9H, s), 1.54-1.70 (5H, m), 2.73-2.81 (2H, m), 3.53-3.57 (1H, m), 3.67 (2H, d, J=8.5 Hz), 4.62 (1H, br), 5.10 (1H, s), 7.15-7.18 (1H, m), 7.32-7.44 (7H, m), 7.52 (2H, m, J=6.6 Hz, 1.2 Hz), 7.68 (1H, dd, J=8.6 Hz, 1.8 Hz), 7.87 (1H, d, J=1.9 Hz)

Example 205

2-amino-5-[4-(3-benzyloxyphenylsulfinyl)-2-chlorophenyl]pentane-1-ol hydrochloride

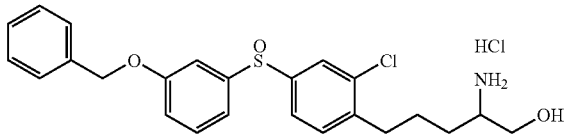

Using the compound of Example 203, the reaction was carried out in the same manner as in Example 76 to give the desired product as a yellow powder.

FABMS: 454 ([M+H]$^+$)

$^1$H-NMR (400 MHz, DMSO-d$_6$) δ 1.51-1.58 (4H, m), 2.69 (2H, t, J=7.3 Hz), 3.06 (1H, br), 3.38-3.44 (1H, m), 3.53-3.58 (1H, m), 5.15 (2H, s), 5.26 (1H, t, J=4.9 Hz), 7.13 (1H, dd, J=8.0 Hz, 2.0 Hz), 7.30-7.51 (9H, m), 7.62 (1H, dd, J=8.0 Hz, 2.0 Hz), 7.76 (1H, d, J=2.0 Hz), 7.84 (3H, br)

MP=114-116° C. (CH$_2$Cl$_2$-iPr$_2$O)

Example 206

2-amino-5-[4-(3-benzyloxyphenylsulfonyl)-2-chlorophenyl]pentane-1-ol hydrochloride

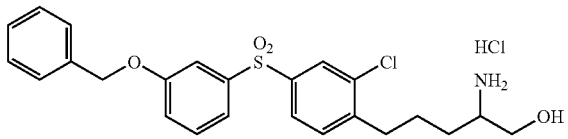

Using the compound of Example 204, the reaction was carried out in the same manner as in Example 76 to give the desired product as a pale yellow powder.

FABMS: 460 ([M+H]$^+$)

$^1$H-NMR (400 MHz, DMSO-d$_6$) δ 1.51-1.63 (4H, m), 2.76 (2H, t, J=7.3 Hz), 3.08 (1H, br), 3.40-3.43 (1H, m), 3.56-3.58 (1H, m), 5.21 (2H, s), 5.27 (1H, t, J=4.9 Hz), 7.34-7.41 (4H, m), 7.46 (2H, d, J=6.7 Hz), 7.55-7.61 (4H, m), 7.80 (3H, br), 7.88 (1H, dd, J=8.6 Hz, 1.8 Hz), 8.00 (1H, d, J=1.8 Hz)

MP=154-156° C. (CH$_2$Cl$_2$-iPr$_2$O).

Example 207 and 208

(+)-5-[4-(3-benzyloxyphenylthio)-2-chlorophenyl]-2-propyl-2-t-butoxycarbonylaminopentane-1-ol and (−)-5-[4-(3-benzyloxyphenylthio)-2-chlorophenyl]-2-propyl-2-t-butoxycarbonylaminopentane-1-ol

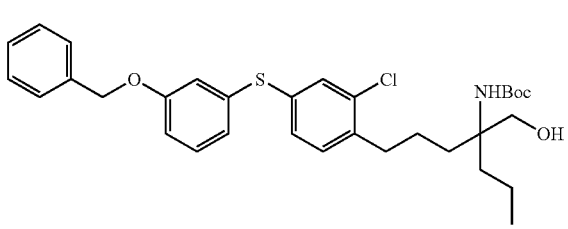

The compound of Example 197 was dissolved in acetonitrile. To this solution, Boc$_2$O was added and the reaction was allowed to proceed at room temperature. The solvent was

Example 209

(+)-2-amino-5-[4-(3-benzyloxyphenylthio)-2-chlorophenyl]-2-propylpentane-1-ol

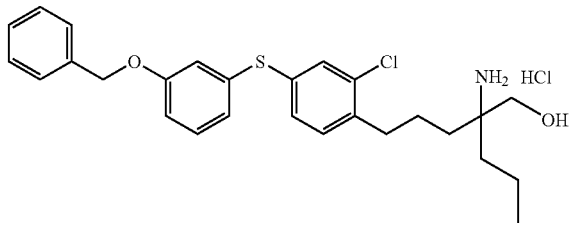

Using the compound of Example 208, the reaction was carried out in the same manner as in Example 76 to give the desired product as a colorless powder.

FABMS: 470 ([M+H]$^+$)

$^1$H-NMR (400 MHz, DMSO-d$_6$) δ 0.83 (3H, t, J=7.3 Hz), 1.02-1.24 (2H, m), 1.16-1.24 (2H, m), 1.40-1.54 (4H, m), 2.66 (2H, br s), 3.37-3.38 (2H, m), 5.08 (2H, s), 5.41-5.43 (1H, m), 6.89 (1H, d, J=7.3 Hz), 6.95-7.00 (2H, m), 7.23 (1H, d, J=7.3 Hz), 7.31-7.41 (8H, m), 7.69-7.83 (3H, br)

MP=55-57° C.

[α]$^{23.4}_D$ +3.9° (C=0.98, MeOH)

Examples 210 and 211

Using dimethylpropargylmalonate or diethylisobutylmalonate, the reaction was carried out in the same manner as in Example 152 to synthesize the respective compounds shown in Table 15 below.

TABLE 15

| Examples | R | R' | Characteristics | MS(EI) M$^+$ |
|---|---|---|---|---|
| 210 | —CH$_2$CCH | Me | Colorless oil | 536 |
| 211 | i-Bu | Et | Colorless oil | 583* |

*FABMS[M + H]$^+$

Example 212

Methyl 5-[4-(3-benzyloxyphenylthio)-2-chlorophenyl]-2-hydroxymethyl-2-propargylpentanoate

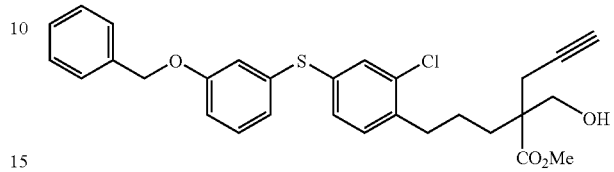

The compound of Example 210 (1.64 g) was dissolved in THF (40 mL). To this solution, LiAl(OtBu)$_3$H (3.889) was added while the solution was chilled on an ice bath. After stirring, the mixture was allowed to warm to room temperature and was further stirred for 2 days. The mixture was again ice-chilled, followed by the addition of diluted hydrochloric acid and filtration to remove the insoluble material. The mixture was then extracted with ethyl acetate and the extract was washed with a saturated aqueous solution of sodium chloride. The organic phase was then dried over anhydrous sodium sulfate, and the solvent was removed and was concentrated. The residue was purified on a silica gel column chromatography (hexane:ethyl acetate=2:1) to give the desired product as a colorless oil (1.12 g).

FABMS: 508 ([M+H]$^+$)

Example 213

Ethyl 5-[4-(3-benzyloxyphenylthio)-2-chlorophenyl]-2-isobutyl-2-hydroxymethylpentanoate

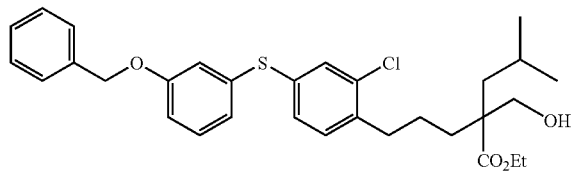

Using the compound of Example 211, the reaction was carried out in the same manner as in Example 212 to give the desired product as a colorless oil.

MS (EI): 540 [M]$^+$ $^1$H-NMR (400 MHz, CDCl$_3$) δ 0.85 (3H, d, J=6.7 Hz), 0.86 (3H, d, J=6.7 Hz), 1.26 (3H, t, J=7.3 Hz), 1.45-1.77 (7H, m), 2.16 (1H, t, J=6.7 Hz), 2.68 (2H, t, J=7.3 Hz), 3.60 (1H, dd, J=11.6 Hz, 6.7 Hz), 3.78 (1H, dd, J=11.6 Hz, 6.7 Hz), 4.11-4.17 (2H, m), 5.02 (2H, s), 6.85-6.94 (3H, m), 7.12-7.17 (2H, m), 7.22 (1H, t, J=7.8 Hz), 7.30-7.40 (6H, m)

Example 214

Methyl 5-[4-(3-benzyloxyphenylthio)-2-chlorophenyl]-2-methoxymethyloxymethyl-2-propargylpentanoate

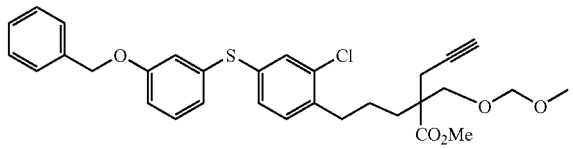

The compound of Example 212 (1.12 g) was dissolved in acetonitrile (30 mL). To this solution, diisopropylamine (0.58 mL) and MOMCl (0.25 mL) were added while the solution was stirred and chilled in an ice bath. The mixture was stirred overnight. Subsequently, water was added and the mixture was extracted with ethyl acetate. The extract was washed with a saturated aqueous solution of sodium chloride and the organic phase was dried over anhydrous magnesium sulfate. The solvent was concentrated and the residue was purified on a silica gel column chromatography (hexane:ethyl acetate=5:1) to give the desired product as a colorless oil (1.12 g).

MS (EI): 552 [M]$^+$ $^1$H-NMR (400 MHz, CDCl$_3$) δ 1.45-1.50 (1H, m), 1.59-1.73 (3H, m) 1.94 (1H, t, J=2.4 Hz), 2.56-2.73 (4H, m), 3.33 (3H, s), 3.57-3.74 (5H, m), 4.59 (2H, s), 5.02 (2H, s), 6.85-6.94 (3H, m), 7.10-7.16 (2H, m), 7.22 (1H, t, J=7.9 Hz), 7.32-7.39 (6H, m)

Example 215

Ethyl 5-[4-(3-benzyloxyphenylthio)-2-chlorophenyl]-2-isobutyl-2-methoxymethyloxymethylpentanoate

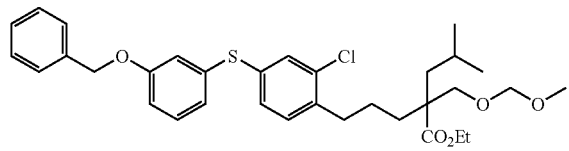

Using the compound of Example 213, the reaction was carried out in the same manner as in Example 214 to give the desired product as a yellow oil.

MS (EI): 584 [M]$^+$ $^1$H-NMR (400 MHz, CDCl$_3$) δ 0.83 (3H, d, J=6.8 Hz), 0.85 (3H, d, J=6.8 Hz), 1.24 (3H, t, J=7.3 Hz), 1.45-1.76 (7H, m), 2.69 (2H, t, J=7.3 Hz), 3.32 (3H, s), 3.57 (1H, d, J=9.8 Hz), 3.65 (1H, d, J=9.8 Hz), 4.08-4.14 (2H, m), 4.57 (2H, s), 5.02 (2H, s), 6.85-6.95 (3H, m), 7.11-7.16 (2H, m), 7.22 (1H, t, J=7.8 Hz), 7.30-7.41 (6H, m)

Example 216

5-[4-(3-benzyloxyphenylthio)-2-chlorophenyl]-2-methoxymethyloxymethyl-2-propargylpentanoic acid

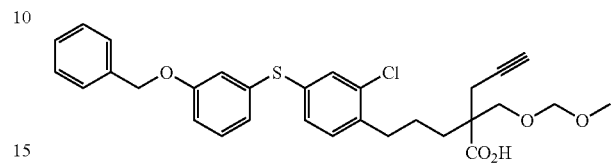

The compound of Example 214 (1.129) was dissolved in a mixed solvent composed of MeOH:THF=1:1 (12 mL). To this solution, a 10% aqueous solution of sodium hydroxide (4 mL) was added and the mixture was refluxed. After 20 hours, the mixture was diluted with water, and hydrochloric acid was added to make the mixture acidic. The mixture was then extracted with ethyl acetate and the extract was washed with a saturated aqueous solution of sodium chloride. The organic phase was then dried over anhydrous magnesium sulfate. The solvent was removed to give the desired product as a yellow oil (1.09 g).

MS (EI): 538 [M]$^+$ $^1$H-NMR (400 MHz, CDCl$_3$) δ 1.53-1.77 (4H, m), 1.96 (1H, t, J=2.4 Hz), 2.59 (1H, dd, J=17.1 Hz, 2.4 Hz), 2.68-2.73 (3H, m), 3.33 (3H, s), 3.69 (1H, d, J=9.8 Hz), 3.73 (1H, d, J=9.8 Hz), 4.60 (2H, s), 5.01 (2H, s), 6.85-6.93 (3H, m), 7.11 (1H, d, J=7.9 Hz), 7.15 (1H, dd, J=7.9 Hz, 1.8 Hz), 7.22 (1H, t, J=7.9 Hz), 7.30-7.40 (6H, m)

Example 217

5-[4-(3-benzyloxyphenylthio)-2-chlorophenyl]-2-isobutyl-2-methoxymethyloxymethylpentanoic acid

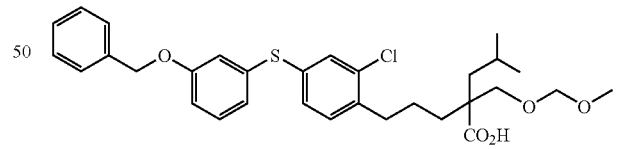

Using the compound of Example 215, the reaction was carried out in the same manner as in Example 216 to give the desired product as a yellow oil.

FABMS: 556 ([M+H]$^+$)

$^1$H-NMR (400 MHz, CDCl$_3$) δ 0.83 (3H, d, J=6.8 Hz), 0.85 (3H, d, J=6.8 Hz), 1.47-1.84 (7H, m), 2.69 (2H, t, J=7.3 Hz), 3.31 (3H, s), 3.56 (1H, d, J=9.2 Hz), 3.65 (1H, d, J=9.2 Hz), 4.58 (2H, s), 5.01 (2H, s), 6.86 (1H, dd, J=8.6 Hz, 2.4 Hz), 6.90-6.94 (2H, m), 7.11-7.16 (2H, m), 7.22 (1H, t, J=7.8 Hz), 7.30-7.40 (6H, m)

Example 218

7-[4-(3-benzyloxyphenylthio)-2-chlorophenyl]-4-methoxycarbonylamino-4-methoxymethyloxymethyl-1-heptin Using the compound of Example 216, the reaction was carried out in the same manner as in Example 163 to give the desired product as a colorless oil.

FABMS: 568 ([M+H]$^+$)

$^1$H-NMR (400 MHz, CDCl$_3$) δ 1.57-1.66 (4H, m), 1.85-1.93 (1H, m), 1.99 (1H, t, J=2.4 Hz), 2.00-2.05 (1H, m), 2.64-2.75 (4H, m), 3.35 (3H, s), 3.61 (3H, s), 3.62 (1H, d, J=9.8 Hz), 3.71 (1H, d, J=9.8 Hz), 4.61 (2H, s), 4.92 (1H, s), 5.01 (2H, s), 6.85-6.94 (3H, m), 7.12-7.17 (2H, m), 7.22 (1H, t, J=7.9 Hz), 7.30-7.40 (6H, m)

Example 219

7-[4-(3-benzyloxyphenylthio)-2-chlorophenyl]-4-methoxycarbonylamino-4-methoxymethyloxymethyl-2-methylheptane Using the compound of Example 217, the reaction was carried out in the same manner as in Example 163 to give the desired product as a yellow oil.

MS (EI): 585 [M]$^+$ $^1$H-NMR (400 MHz, CDCl$_3$) δ 0.91 (3H, d, J=6.8 Hz), 0.92 (3H, d, J=6.8 Hz), 1.58-1.82 (7H, m), 2.68 (2H, t, J=7.3 Hz), 3.34 (3H, s), 3.56 (3H, s), 3.78 (1H, d, J=11.0 Hz), 3.87 (1H, d, J=11.0 Hz), 4.59 (2H, s), 4.70 (1H, s), 5.02 (2H, s), 6.82-6.94 (3H, m), 7.11-7.14 (2H, m), 7.17-7.24 (1H, m), 7.32-7.39 (6H, m)

Example 220

4-amino-7-[4-(3-benzyloxyphenylthio)-2-chlorophenyl]-4-methoxymethyloxymethyl-1-heptin Using the compound of Example 218, the reaction was carried out in the same manner as in Example 184 to give the desired product as a colorless oil.

MS (EI): 509 [M]$^+$ $^1$H-NMR (400 MHz, CDCl$_3$) δ 1.51 (2H, br), 1.56-1.68 (4H, m), 2.01 (1H, t, J=2.4 Hz), 2.32 (1H, dd, J=16.5 Hz, 2.4 Hz), 2.38 (1H, dd, J=16.5 Hz, 2.4 Hz), 2.71 (2H, t, J=7.3 Hz), 3.35 (3H, s), 3.37 (1H, d, J=9.2 Hz), 3.43 (1H, d, J=9.2 Hz), 4.62 (2H, s), 5.02 (2H, s), 6.87 (1H, dd, J=8.6 Hz, 2.4 Hz), 6.91-6.94 (2H, m), 7.15 (2H, s), 7.22 (1H, t, J=7.9 Hz), 7.30-7.41 (6H, m)

Example 221

4-amino-7-[4-(3-benzyloxyphenylthio)-2-chlorophenyl]-4-methoxymethyloxymethyl-2-methylheptane Using the compound of Example 219, the reaction was carried out in the same manner as in Example 184 to give the desired product as a colorless oil

MS (EI): 527 [M]$^+$ $^1$H-NMR (400 MHz, CDCl$_3$) δ 0.93 (3H, d, J=6.8 Hz), 0.94 (3H, d, J=6.8 Hz), 1.24-1.32 (4H, m), 1.48-1.62 (4H, m), 1.68-1.75 (1H, m), 2.69 (2H, t, J=7.3 Hz), 3.27 (1H, d, J=9.2 Hz), 3.32 (1H, d, J=9.2 Hz), 3.35 (3H, s), 4.61 (2H, s), 5.01 (2H, s), 6.86 (1H, dd, J=7.9 Hz, 2.4 Hz), 6.91-6.94 (2H, m), 7.12-7.17 (2H, m), 7.22 (1H, t, J=7.9 Hz), 7.30-7.40 (6H, m)

Example 222

2-amino-5-[4-(3-benzyloxyphenylthio)-2-chlorophenyl]-2-propargylpentane-1-ol hydrochloride Using the compound of Example 220, the reaction was carried out in the same manner as in Example 76 to give the desired product as a colorless amorphous.

FABMS: 466 ([M+H]$^+$)

$^1$H-NMR (400 MHz, DMSO-d$_6$) δ 1.65 (4H, br s), 2.67 (2H, t, J=7.3 Hz), 3.08 (1H, s), 3.46 (2H, br), 5.10 (2H, s), 5.56 (1H, br), 6.91 (1H, d, J=7.9 Hz), 6.96-7.02 (2H, m), 7.24 (1H, dd, J=7.9 Hz, 1.8 Hz) 7.30-7.40 (8H, m), 7.88 (3H, br)

Example 223

2-amino-5-[4-(3-benzyloxyphenylthio)-2-chlorophenyl]-2-isobutylpentane-1-ol hydrochloride

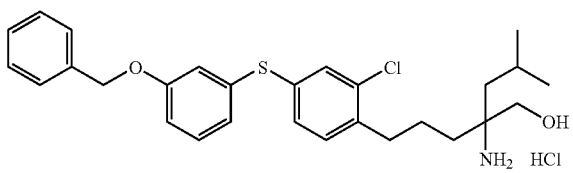

Using the compound of Example 221, the reaction was carried out in the same manner as in Example 76 to give the desired product as a colorless oil.

FABMS: 484 ([M+H]$^+$)

$^1$H-NMR (400 MHz, DMSO-d$_6$) δ 0.84 (3H, d, J=6.7 Hz), 0.86 (3H, d, J=6.7 Hz), 1.07-1.18 (2H, m), 1.29-1.33 (2H, m), 1.48-1.55 (2H, m) 1.62-1.68 (1H, m), 2.62 (2H, t, J=7.3 Hz), 3.07 (1H, d, J=9.8 Hz), 3.11 (1H, d, J=9.8 Hz), 4.44 (1H, br), 5.09 (2H, s), 6.88-7.00 (3H, m), 7.22 (1H, dd, J=7.9 Hz, J=1.8 Hz), 7.29-7.42 (8H, m)

Example 224

5-[4-(3-benzyloxyphenylthio)-2-chlorophenyl]-2-t-butoxycarbonylamino-2-methoxymethyloxymethyl-pentane-1-ol

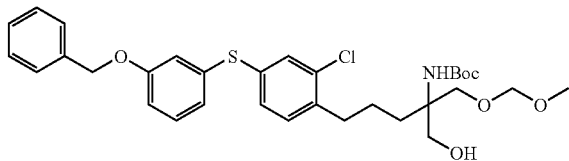

2-[4-(3-benzyloxyphenylthio)-2-chlorophenyl]propyl-2-t-butoxycarbonylamino-1,3-propanediol (5.00 g) was dissolved in MeCN (100 mL). While the solution was chilled in an ice bath, diisopropylethylamine (2.03 mL) and MOMCl (0.88 mL) were added. Subsequently, the mixture was stirred for 16 hours while being allowed to warm to room temperature. Following addition of water, the mixture was extracted with ethyl acetate and the extract was washed with a saturated aqueous solution of sodium chloride. The organic phase was then dried over anhydrous magnesium sulfate. The solvent was concentrated and the residue was purified on a silica gel column chromatography (hexane:ethyl acetate=2:1) to give the desired product as a colorless oil (2.36 g).

FABMS: 602 ([M+H]$^+$)

$^1$H-NMR (400 MHz, CDCl$_3$) δ 1.43 (9H, s), 1.54-1.68 (4H, m), 1.81-1.86 (1H, m), 2.70 (2H, t, J=7.3 Hz), 3.34 (3H, s), 3.46 (1H, d, J=9.8 Hz), 3.63-3.72 (3H, m), 3.99 (1H, br), 4.60 (2H, s), 5.02 (2H, s), 5.07 (1H, br), 6.87 (1H, dd, J=8.6 Hz, 2.4 Hz), 6.91-6.95 (2H, m), 7.11-7.16 (2H, m), 7.22 (1H, t, J=7.9 Hz), 7.30-7.43 (6H, m)

Example 225

5-[4-(3-benzyloxyphenylthio)-2-chlorophenyl]-2-t-butoxycarbonylamino-2-methoxymethyloxymethyl-pentanal

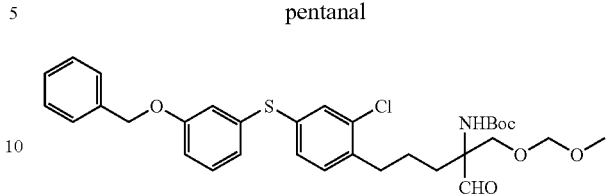

Using the compound of Example 224, the reaction was carried out in the same manner as in Example 133 to give the desired product as a colorless oil.

FABMS: 600 ([M+H]$^+$)

$^1$H-NMR (400 MHz, CDCl$_3$) δ 1.43 (9H, s), 1.54-1.60 (2H, m), 1.77-1.84 (1H, m), 2.00-2.15 (1H, m), 2.68 (2H, t, J=7.3 Hz), 3.30 (3H, s), 3.78 (1H, d, J=9.8 Hz), 3.98 (1H, d, J=9.8 Hz), 4.57 (2H, s), 5.02 (2H, s), 5.39 (1H, br), 6.86-6.95 (3H, m), 7.07-7.14 (2H, m), 7.21-7.39 (7H, m), 9.40 (1H, s)

Example 226

7-[4-(3-benzyloxyphenylthio)-2-chlorophenyl]-4-t-butoxycarbonylamino-4-methoxymethyloxymethyl-3-heptene

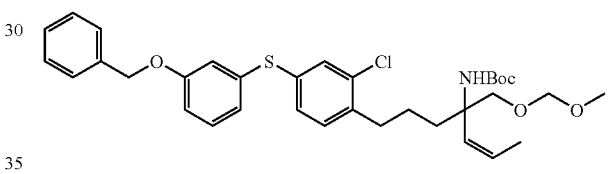

EtPh$_3$PI (906 mg) was dissolved in THF (20 mL). To this solution, LDA (2.20 mL), chilled to −78° C., was added under atmosphere of argon gas and the mixture was stirred for 10 min. Subsequently, the mixture was stirred at 0° C. for 5 min and was then chilled again to −78° C., followed by the dropwise addition of a THF solution (10 mL) of the compound of Example 225 (1.00 g). The mixture was further stirred at −78° C. for 1 hour and at room temperature for 1 hour. Following addition of water, the mixture was extracted with ethyl acetate and the extract was washed with a saturated aqueous solution of sodium chloride. The organic phase was then dried over anhydrous magnesium sulfate. The solvent was removed and the residue was purified on a silica gel column chromatography (hexane:ethyl acetate=4:1) to give the desired product as a yellow oil (172 mg).

FABMS: 612 ([M+H]$^+$)

$^1$H-NMR (400 MHz, CDCl$_3$) δ 1.41 (9H, s), 1.60-1.66 (2H, m), 1.74 (3H, dd, J=7.3 Hz, 1.8 Hz), 1.89-1.93 (2H, m), 2.69 (2H, t, J=8.0 Hz), 3.34 (3H, s), 3.64 (1H, d, J=9.2 Hz), 3.71 (1H, d, J=9.2 Hz), 4.60 (2H, s), 4.83 (1H, br), 5.02 (2H, s), 5.30 (1H, br d, J=12.2 Hz), 5.54-5.57 (1H, m), 6.86 (1H, dd, J=8.0 Hz, 2.4 Hz), 6.91-6.94 (2H, m), 7.11-7.16 (2H, m), 7.22 (1H, t, J=7.9 Hz), 7.30-7.41 (6H, m)

Example 227

3-amino-7-[4-(3-benzyloxyphenylthio)-2-chlorophenyl]-4-hydroxymethyl-3-heptene hydrochloride Using the compound of Example 226, the reaction was carried out in the same manner as in Example 76 to give the desired product as a colorless oil.

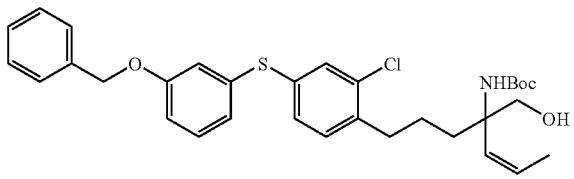

FABMS: 468 ([M+H]$^+$)

$^1$H-NMR (400 MHz, CDCl$_3$) δ 1.61-1.75 (4H, m), 1.77 (3H, dd, J=7.3 Hz, 1.8 Hz), 2.70 (2H, t, J=8.0 Hz), 3.37 (1H, d, J=10.4 Hz), 3.46 (1H, d, J=10.4 Hz), 5.01 (2H, s), 5.19 (1H, dd, J=12.2 Hz, 1.8 Hz), 5.55 (1H, dq, J=12.2 Hz, 7.3 Hz), 6.87 (1H, dd, J=7.8 Hz, 2.4 Hz), 6.91-6.94 (2H, m), 7.12-7.17 (2H, m), 7.22 (1H, t, J=7.9 Hz), 7.31-7.40 (6H, m)

Exemplary Experiment

Inhibitory Effects of Test Compounds on Host vs Graft Reaction in Mice

This experiment was performed according to the method described in *Transplantation* 55(3) (1993): 578-591. Spleens were collected from 7 to 12 week old male BALB/c mice (available from CLEA JAPAN Inc., CHARLES RIVER JAPAN Inc., or JAPAN SLC Inc.). The spleens were placed in an RPMI-1640 medium (SIGMA, GIBCO INDUSTRIES Inc., or IWAKI GLASS Co., Ltd.) and were gently pressed between two slide glasses and then passed through a cell strainer (70 μm, Falcon) to form a cell suspension. The suspension was then centrifuged and the supernatant was discarded. An ammonium chloride-Tris isotonic buffer was added to the suspension to lyse erythrocytes. The cells were then centrifuged three times in RPMI-1640 medium for washing and were resuspended in an RPMI-1640 medium. To this suspension, mitomycin C (KYOWA HAKKO KOGYO Co., Ltd.) was added to a final concentration of 25 μg/mL and the suspension was incubated for 30 minutes at 37° C. in a 5% CO$_2$ atmosphere. The cells were centrifuged three times in RPMI-1640 medium for washing and were resuspended in an RPMI-1640 medium so that the medium would contain 2.5× 10$^8$ cells/mL. This suspension served as a "stimulation cell suspension." Using a 27 G needle, along with a microsyringe (Hamilton), 20 μL (5×10$^6$ cells/mouse) of the stimulation cell suspension was subcutaneously injected into the right hind footpad of 6 to 12 week old male C3H/HeN mice (CLEA JAPAN Inc., CHARLES RIVER JAPAN Inc., or JAPAN SLC Inc.). As a normal control group, a group of mice were injected with RPMI-1640 medium alone. 4 days after the injection, right popliteal lymph nodes were collected and were weighed on a Mettler AT201 electronic scale (METTLER TOLEDO Co., Ltd.). Each animal was intraperitoneally administered a test compound once a day for four consecutive days starting on the day of the injection of the stimulation cells (i.e., total of 4 times). As a control group, a group of the animals were administered the same solvent as that used in the preparation of each test compound. The results are shown in Table 16 below:

TABLE 16

| Example No. | Dose (mg/kg) | Inhibition (%) |
|---|---|---|
| 84 | 10 | 79 |
| 96 | 10 | 73 |
| 101 | 0.3 | 44 |

TABLE 16-continued

| Example No. | Dose (mg/kg) | Inhibition (%) |
|---|---|---|
| 102 | 1 | 46 |
| 127 | 10 | 57 |
| 131 | 0.3 | 57 |
| 135 | 1 | 69 |
| 136 | 3 | 74 |
| 137 | 3 | 70 |
| 138 | 10 | 66 |
| 139 | 10 | 55 |
| 140 | 3 | 60 |
| 143 | 0.3 | 60 |
| 145 | 0.3 | 64 |
| 148 | 0.3 | 71 |
| 151 | 0.03 | 65 |
| 184 | 0.1 | 45 |
| 185 | 0.1 | 88 |
| 188 | 0.1 | 78 |
| 189 | 0.03 | 71 |
| 191 | 0.1 | 41 |
| 192 | 0.1 | 86 |
| 194 | 0.1 | 70 |
| 196 | 0.03 | 63 |
| 197 | 0.03 | 54 |
| 199 | 0.3 | 71 |
| 209 | 0.03 | 71 |
| 222 | 0.3 | 57 |
| 223 | 0.3 | 70 |
| 227 | 0.3 | 58 |

As has been demonstrated by the results, each of the compounds of the present invention represented by the general formula (1) has proven to be effective in the animal model.

INDUSTRIAL APPLICABILITY

As set forth, the present invention has been devised in recognition of the fact that the novel amino alcohol derivatives with a diarylsulfide or diarylether group exhibit strong immunosuppressive effects, the effects particularly significant when one of the aryl groups includes, at its para-position, a carbon chain with an amino alcohol group and the other aryl group includes a substituent at its meta-position. Effective immunosuppressors, the compounds of the present invention have a great potential as a prophylactic or therapeutic agent against rejection in organ or bone marrow transplantation, autoimmune diseases, rheumatoid arthritis, psoriasis, atopic dermatitis, bronchial asthma, pollinosis and various other diseases.

The invention claimed is:

1. An amino alcohol derivative, or an optical isomer, or pharmaceutically acceptable salt thereof, the amino alcohol derivative being represented by the following general formula (1):

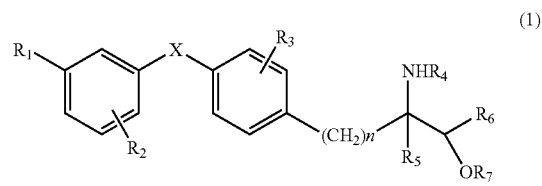

wherein R$_1$ is a halogen atom, a trihalomethyl group, a lower alkyl group having 1 to 4 carbon atoms, an aralkyl group, a lower alkoxy group having 1 to 4 carbon atoms, a substituted or unsubstituted phenoxy group, a substituted or unsubstituted aralkyloxy group, a lower alkylthio group having 1 to 4 carbon atoms, a lower alkylsulfinyl group having 1 to 4 carbon atoms, or a lower alkylsulfonyl group having 1 to 4 carbon atoms; $R_2$ is a hydrogen atom, a halogen atom, a trihalomethyl group, a lower alkyl group having 1 to 4 carbon atoms, an aralkyl group, a lower alkoxy group having 1 to 4 carbon atoms, or a aralkyloxy group; $R_3$ is a hydrogen atom; $R_4$ is a hydrogen atom, a lower alkyl group having 1 to 4 carbon atoms, a phenyl group, a substituted or unsubstituted benzyl group, a lower aliphatic acyl group having 1 to 5 carbon atoms, or a substituted or unsubstituted benzoyl group; $R_5$ is a hydrogen atom, a monohalogenated methyl group, a lower alkyl group having 1 to 4 carbon atoms, a lower alkoxymethyl group having 1 to 4 carbon atoms, a lower alkylthiomethyl group having 1 to 4 carbon atoms, a hydroxyethyl group, a hydroxypropyl group, a phenyl group, an aralkyl group, a lower alkenyl group having 2 to 4 carbon atoms, or a lower alkynyl group having 2 to 4 carbon atoms; $R_6$ and $R_7$ are each independently a hydrogen atom, or a lower alkyl group having 1 to 4 carbon atoms; and X is O, S, SO, or $SO_2$; and n is an integer from 2 to 4.

2. The amino alcohol derivative according to claim 1, an optical isomer, or pharmaceutically acceptable salt thereof, wherein the compound represented by the general formula (1) is represented by the following general formula (1a):

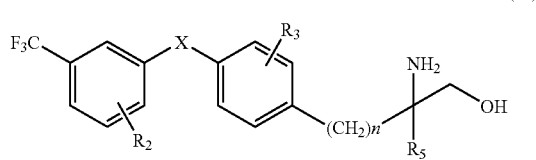

(1a)

wherein Y represents O or S, and $R_2$, $R_3$, $R_5$ and n are as described in claim 1.

3. The amino alcohol derivative according to claim 1, an optical isomer, or pharmaceutically acceptable salt thereof, wherein the compound represented by the general formula (1) is represented by the following general formula (1b):

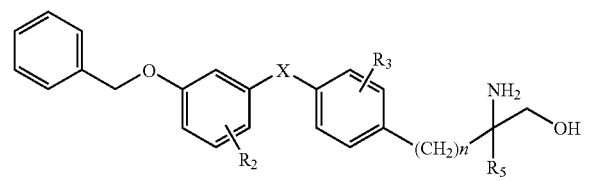

(1b)

wherein Y represents O or S, and $R_2$, $R_3$, $R_5$ and n are as described in claim 1.

4. An immunosuppressive agent containing an inactive ingredient, and as an active ingredient at least one of an amino alcohol derivative, and an optical isomer, and pharmaceutically acceptable salt thereof, the amino alcohol derivative being represented by the following general formula (1):

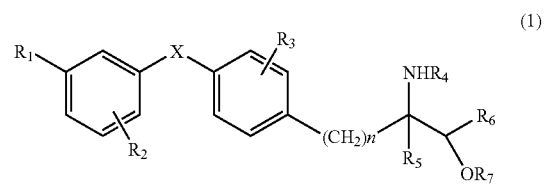

(1)

wherein $R_1$ is a halogen atom, a trihalomethyl group, a lower alkyl group having 1 to 4 carbon atoms, an aralkyl group, a lower alkoxy group having 1 to 4 carbon atoms, a substituted or unsubstituted phenoxy group, a substituted or unsubstituted aralkyloxy group, a lower alkylthio group having 1 to 4 carbon atoms, a lower alkylsulfinyl group having 1 to 4 carbon atoms, or a lower alkylsulfonyl group having 1 to 4 carbon atoms; $R_2$ is a hydrogen atom, a halogen atom, a trihalomethyl group, a lower alkyl group having 1 to 4 carbon atoms, an aralkyl group, a lower alkoxy group having 1 to 4 carbon atoms, or a aralkyloxy group; $R_3$ is a hydrogen atom; $R_4$ is a hydrogen atom, a lower alkyl group having 1 to 4 carbon atoms, a phenyl group, a substituted or unsubstituted benzyl group, a lower aliphatic acyl group having 1 to 5 carbon atoms, or a substituted or unsubstituted benzoyl group; $R_5$ is a hydrogen atom, a monohalogenated methyl group, a lower alkyl group having 1 to 4 carbon atoms, a lower alkoxymethyl group having 1 to 4 carbon atoms, a lower alkylthiomethyl group having 1 to 4 carbon atoms, a hydroxyethyl group, a hydroxypropyl group, a phenyl group, an aralkyl group, a lower alkenyl group having 2 to 4 carbon atoms, or a lower alkynyl group having 2 to 4 carbon atoms; $R_6$ and $R_7$ are each independently a hydrogen atom, or a lower alkyl group having 1 to 4 carbon atoms; and X is O, S, SO, or $SO_2$; and n is an integer from 2 to 4.

5. The immunosuppressive agent according to claim 4, containing as an active ingredient at least one of the amino alcohol derivative, and the optical isomer, and pharmaceutically acceptable salt thereof wherein the compound represented by the general formula (1) is represented by the following general formula (1a):

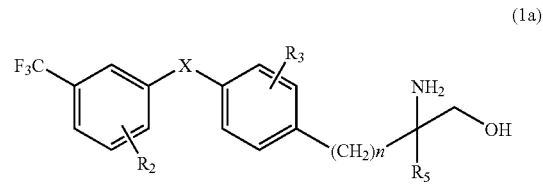

(1a)

wherein Y represents O or S, and $R_2$, $R_3$, $R_5$ and n are as described in claim 4.

6. The immunosuppressive agent according to claim 4, containing as an active ingredient at least one of the amino alcohol derivative, and the optical isomer, and pharmaceutically acceptable salt thereof, wherein the compound represented by the general formula (1) is represented by the following general formula (1b):

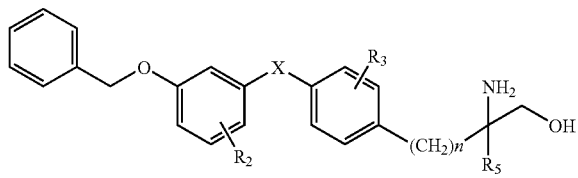

(1b)

wherein Y represents O or S, and $R_2$, $R_3$, $R_5$ and n are as described in claim 4.

7. The immunosuppressive agent according to claim 4, intended for use as a therapeutic agent for autoimmune diseases.

8. The immunosuppressive agent according to claim 4, intended for use as a therapeutic agent for rheumatoid arthritis.

9. The immunosuppressive agent according to claim 4, intended for use as a therapeutic agent for psoriasis or atopic dermatitis.

10. The immunosuppressive agent according to claim 4, intended for use as a therapeutic agent for bronchial asthma or pollinosis.

11. The immunosuppressive agent according to claim 4, intended for use as a therapeutic agent for rejection in organ or bone marrow transplantation.

12. A method of treating autoimmune diseases, rheumatoid arthritis, psoriasis, atopic dermatitis, bronchial asthma, pollinosis, or rejection of organ or bone morrow transplantation, which comprises administering an effective amount of the amino alcohol derivative, optical isomer or pharmaceutically acceptable salt thereof as defined in claim 1 to a patient in need of said treatment.

* * * * *